(12) United States Patent
Sorge

(10) Patent No.: US 6,607,878 B2
(45) Date of Patent: Aug. 19, 2003

(54) COLLECTIONS OF UNIQUELY TAGGED MOLECULES

(75) Inventor: Joseph A. Sorge, Wilson, WY (US)

(73) Assignee: Stratagene, La Jolla, CA (US)

( * ) Notice: Subject to any disclaimer, the term of this patent is extended or adjusted under 35 U.S.C. 154(b) by 0 days.

(21) Appl. No.: 08/944,410

(22) Filed: Oct. 6, 1997

(65) Prior Publication Data

US 2003/0050453 A1 Mar. 13, 2003

(51) Int. Cl.$^7$ .......................... C12Q 1/68; C07H 21/04

(52) U.S. Cl. .......................................... 435/6; 536/23.1

(58) Field of Search .................. 435/6, 7.94; 530/360; 436/501; 536/23.1; 935/78

(56) References Cited

U.S. PATENT DOCUMENTS

| | | | |
|---|---|---|---|
| 5,102,785 A | 4/1992 | Livak et al. | |
| 5,143,854 A | 9/1992 | Pirrung et al. | |
| 5,264,563 A | 11/1993 | Huse | |
| 5,270,170 A | 12/1993 | Schatz et al. | |
| 5,412,087 A | 5/1995 | McGall et al. | |
| 5,427,908 A | 6/1995 | Dower et al. | |
| 5,429,807 A | 7/1995 | Matson et al. | |
| 5,445,934 A | 8/1995 | Fodor et al. | |
| 5,492,806 A | 2/1996 | Drmanac et al. | |
| 5,494,810 A | 2/1996 | Barany et al. | 435/91.52 |
| 5,503,805 A | 4/1996 | Sugarman et al. | |
| 5,510,270 A | 4/1996 | Fodor et al. | |
| 5,523,388 A | 6/1996 | Huse | |
| 5,525,464 A | 6/1996 | Drmanac et al. | |
| 5,541,061 A | 7/1996 | Fodor et al. | |
| 5,547,839 A | 8/1996 | Dower et al. | |
| 5,552,278 A | 9/1996 | Brenner | |
| 5,556,752 A | 9/1996 | Lockhart et al. | |
| 5,565,340 A | 10/1996 | Chenchik et al. | |
| 5,573,905 A | 11/1996 | Lerner et al. | |
| 5,580,717 A | 12/1996 | Dower et al. | |
| 5,830,711 A | 11/1998 | Barany et al. | 435/91.1 |

FOREIGN PATENT DOCUMENTS

| | | |
|---|---|---|
| EP | 0717113 A2 | 6/1996 |
| WO | WO92/10587 | 6/1992 |
| WO | WO92/10588 | 6/1992 |
| WO | WO93/06121 | 4/1993 |
| WO | WO 93 20242 A | 10/1993 |
| WO | WO 95 04160 A | 2/1995 |
| WO | WO95/11995 | 5/1995 |
| WO | WO96/12014 | 4/1996 |
| WO | WO96/12039 | 4/1996 |
| WO | WO 96 41011 A | 4/1996 |
| WO | WO 97 27331 A | 4/1996 |
| WO | WO96/22391 | 7/1996 |
| WO | WO 97 32999 A | 9/1997 |
| WO | WO97/45559 | 12/1997 |
| WO | WO 97 46704 A | 12/1997 |
| WO | WO98/03673 | 1/1998 |

OTHER PUBLICATIONS

Speicher et al., "Karyotyping human chromosomes by combinatorial multi–fluor FISH," Nature Genetics, 12:368–375 (1996).
Baron et al., "Oligonucleotide ligation assay (OLA) for the diagnosis of familial hypercholesterolemia," Nature Biotechnology, 14:1279–82 (1996).
Blondelle et al., "Identification of Inhibitors of Melittin Using Nonsupport–bound Combinatorial Libraries," The Journal of Biological Chemistry, 271:4093–99 (1996).
Diatchenko et al., "Suppression subtractive hybridization: A method for generating differentially regulated or tissue–specific cDNA probes and libraries," Proc. Natl. Acad. Sci. USA, 93:6025–30 (1996).
Jurinke et al., "Analysis of Ligase Chain Reaction Products via Matrix–Assisted Laser Desorption/Ionization Time–of–Flight–Mass Spectrometry," Analytical Biochemistry, 237:174–181 (1996).
Kato, "RNA fingerprinting by molecular indexing," Nucleic Acids Research, 24:394–395 (1996).
Lockhart et al., "Expression monitoring by hybridization to high–density oligonucleotide arrays," Nature Biotechnology, 14:1675–80 (1996).
Shoemaker et al., "Quantitative phenotypic analysis of yeast deletion mutants using a highly parallel molecular bar–coding strategy," Nature Genetics, 14:450–456 (1996).
Suzuki et al., "Restriction landmark cDNA scanning (RLCS): a novel cDNA display system using two–dimensional gel electrophoresis," Nucleic Acids Research, 24:289–294 (1996).
Tabler et al., "Representation of unique sequences in libraries of randomized nucleic acids," Nucleic Acids Research, 24:3437–38 (1996).
Fitzgerald et al., "Biochemical mass spectrometry: worth the weight?" Chemistry & Biology, 3:707–715 (1996).
Köster et al., "A strategy for rapid and efficient DNA sequencing by mass spectrometry," Nature Biotechnology, 14:1123–28 (1996).
Li et al., "High–Resolution MALDI Fourier Transform Mass Spectrometry of Oligonucleotides," Analytical Chemistry, 68:2090–96 (1996).
Borman, "DNA Chips Comes of Age," C&EN, pp. 42–43 (Dec. 9, 1996).
Burbaum et al., "A paradigm for drug discovery employing encoded combinatorial libraries," Proc. Natl. Acad. Sci. USA, 92:6027–31 (1995).

(List continued on next page.)

*Primary Examiner*—Kenneth R. Horlick
(74) *Attorney, Agent, or Firm*—Finnegan, Henderson, Farabow, Garrett & Dunner LLP

(57) ABSTRACT

This invention is directed to methods and kits for creating and analyzing molecules using uniquely identifiable tags. The invention is also directed to methods and kits that use uniquely identifiable tags for sequencing DNA, for determining mutations, including substitutions, deletions, and additions, in sample genes, and monitoring mRNA populations.

88 Claims, 16 Drawing Sheets

OTHER PUBLICATIONS

Southern, "DNA fingerprinting by hybridisation to oligonucleotide arrays," Electrophoresis, 16:1539–42 (1995).

Nicolaou et al., "Radiofrequency Encoded Combinatorial Chemistry," Angew. Chem. Int. Ed. Engl., 34:2289–91 (1995).

Fu et al., "A DNA sequencing strategy that requires only five bases of known terminal sequence for priming," Proc. natl. Acad. Sci. USA, 92:10162–66 (1995).

Rastinejad et al., "Studies of Nucleic Acids and Their Protein Interactions by $^{19}$F NMR," Methods in Enzymology, Academic Press, Inc., 261:560–575 (1995).

Velculescu et al., "Serial analysis of gene expression," Science, 270:484–487 (1995).

Wu et al., "On–line NMR detection of amino acids and peptides in microbore LC," Anal. Chem., 67:3101–07 (1995).

Janda, "Tagged versus untagged libraries: Methods for the generation and screening of combinatorial chemical libraries," Proc. Natl. Acad. Sci. USA, 91:10779–85 (1994).

Gallop et al., "Applications of Combinatorial Technologies to Drug Discovery. 1. Background and Peptide Combinatorial Libraries," Journal of Medicinal Chemistry, 37:1223–51 (1994).

Gordon et al., "Applications of Combinatorial Technologies to Drug Discovery. 2. Combinatorial Organic Synthesis, Library Screening Strategies, and Future Directions," Journal of Medicinal Chemistry, 37:1385–1401 (1994).

Southern et al., "Arrays of complementary oligonucleotides for analysing the hybridisation behaviour of nucleic acids," Nucleic Acids Research, 22:1368–73 (1994).

Pinilla et al., "Versatility of Positional Scanning Synthetic Combinatorial Libraries for the Identification of Individual Compounds," Drug Development Research, 33:133–145 (1994).

Nestler et al., "A General Method for Molecular Tagging of Encoded Combinatorial Libraries," J. Org. Chem., 59:4723–24 (1994).

Desjarlais et al., "Length–encoded multiplex binding site determination: Application to zinc finger proteins," Proc. Natl. Acad. Sci. USA, 91:11099–103 (1994).

Erb et al., "Recursive deconvolution of combinatorial chemical libraries," Proc. Natl. Acad. Sci. USA, 91:11422–26 (1994).

Williams et al., "Studies of oligonucleotide interactions by hybridisation to arrays: the influence of dangling ends on duplex yield," Nucleic Acids Research, 22:1365–67 (1994).

Alper, "Drug Discovery on the Assembly Line," Science, 264:1399–1401 (1994).

Mehta et al., "6–Fluoropyridoxol: a novel probe of cellular pH using $^{19}$F NMR spectroscopy," FEBS Lett., 349:234–238 (1994).

Ohlmeyer et al., "Complex synthetic chemical libraries indexed with molecular tags," Proc. Natl. Acad. Sci. USA, 90:10922–26 (1993).

Needels et al., "Generation and screening of an oligonucleotide–encoded synthetic peptide library," Proc. Natl. Acad. Sci. USA, 90:10700–04 (1993), Mendz et al., "Fluorinated probes to measure carboxylesterase activities using $^{19}$F NMR spectroscopy: application to erythrocytes and Helicobacter pylori," Arch. Biochem. Biophys., 305:252–260 (1993).

Blasko et al., "Stoichiometry and structure of complexes of DNA oligomers with microgonotropens and distamycin by 1H NMR spectroscopy and molecular modeling," Proc. Natl. Acad. Sci. USA, 90:10018–22 (1993).

Brenner et al., "Encoded combinatorial chemistry," Proc. Natl. Acad. Sci. USA, 89:5381–83 (1992).

Ried et al., "Simultaneous visualization of seven different DNA probes by in situ hybridization using combinatorial fluorescence and digital imaging microscopy," Proc. Natl. Acad. Sci. USA, 89:1388–92 (1992).

Katahira et al., "A new model for the bending of DNAs containing the oligo(dA) tracts based on NMR observations," Nucleic Acids Research, 18:613–618 (1990).

Day et al., "Detection of Steroid 21–Hydroxylase Alleles Using Gene–Specific PCR and a Multiplexed Ligation Detection Reaction," Genomics, 29:152–162 (1995).

Ross et al., "High level multiplex genotyping by MALDI–TOF mass spectrometry," Nature Biotechnology, 16:1347–1351 (1998) Church et al., "Multiplex DNA Sequencing," Science 240:185–188 (1988).

Arlinghaus H F et al.: "Multiplexed DNA Sequencing and Diagnostics By Hybridization Wth Enriched Stable Isotope Labels", Analytical Chemistry, vol. 69, No. 8, Apr. 15, 1997, pp. 1510–1517.

PRIMER/TEMPLATE OVERLAPS USUALLY 20 NUCLEOTIDES, BUT SHORTENED HERE TO SIMPLIFY ILLUSTRATIONS

| H | G | F | E | D | C | b | a | | columns in the well |
|---|---|---|---|---|---|---|---|---|---|
| + | + | + | + | + | + | 0 | 0 | 1 | 50 µl 50 µM dNTP +Mg |
| - | - | - | - | - | - | 0 | 0 | 2 | 50 µl 50 µM dNTP -Mg |
| 0 | 0 | 0 | 0 | 0 | 0 | 0 | 0 | 3 | EMPTY (0) |
| + | + | + | + | + | + | 0 | 0 | 4 | 100 µl 50 µM dNTP +Mg |
| - | - | - | - | - | - | 0 | 0 | 5 | 100 µl 50 µM dNTP -Mg |
| 0 | 0 | 0 | 0 | 0 | 0 | 0 | 0 | 6 | EMPTY (0) |
| 0 | 0 | 0 | 0 | 0 | 0 | 0 | 0 | 7 | EMPTY (0) |
| + | + | + | + | + | + | 0 | 0 | 8 | 50 µl 15 µM dNTP +Mg |
| - | - | - | - | - | - | 0 | 0 | 9 | 50 µl 15 µM dNTP -Mg |
| 0 | 0 | 0 | 0 | 0 | 0 | 0 | 0 | 10 | EMPTY (0) |
| + | + | + | + | + | + | 0 | 0 | 11 | 100 µl 15 µM dNTP +Mg |
| - | - | - | - | - | - | 0 | 0 | 12 | 100 µl 15 µM dNTP -Mg |
| 5 | 13 | 5 | 2 | 2 | 4 | | | | PLASMID TEMPLATES (3µl) |
| #384 | #392 | #396 | #389 | #393 | #387 | | | | PRIMERS (2µl) |

"+" AND "+Mg" = Mg WAX BEADS

"-" AND "-Mg" = Mg IN BUFFER BUT NO Mg WAX BEADS

FIG. 14

SELECTION EXPERIMENT BY RECONSTITUTION OF TWO
PUBLIC (+/=) AND ONE PRIVATE REGION (-)

STEPS OF THE RECONSTITUTION AND SELECTION
FRAGMENTS, ADAPTORS, PRIMERS AND SIZES

STEPS I/II.   CUT BY *NaeI* AND LIGATION OF Ad-A
                     Ad-A                  EcoRV        Ad-A
              +++++++GGC--584--GATATC--2815--GCC+++

STEPS III/IV.   CUT BY *EcoRV* AND LIGATION OF Ad-B
       Ad-A             Ad-B    Ad-B            Ad-A
    +++++++GGC--584--GAT===   ======ATC--2815-GCC+++

STEP V.   PREAMPLIFICATION
                        +++
                 +++++++GGC--584--GAT======
                             ===

STEP VI.   SELECTIVE PCR
        #379                     #378
    +++AT               +++GG
  NON-SELECTIVE  +++++++GGC--584--GAT======      (NSP)
  PRIMER(NSP)                    TA===        GC===
                                      #381        #380

FIG. 16

SEQUENCE LISTING

<160> NUMBER OF SEQ ID NOS: 113

<210> SEQ ID NO 1
<211> LENGTH: 20
<212> TYPE: DNA
<213> ORGANISM: Artificial
<220> FEATURE:
<223> OTHER INFORMATION: Synthetic primer

<400> SEQUENCE: 1
cactcactca ctcactcact                                          20

<210> SEQ ID NO 2
<211> LENGTH: 20
<212> TYPE: DNA
<213> ORGANISM: Artificial
<220> FEATURE:
<223> OTHER INFORMATION: Synthetic primer

<400> SEQUENCE: 2
gccaacctac cttcctacct                                          20

<210> SEQ ID NO 3
<211> LENGTH: 20
<212> TYPE: DNA
<213> ORGANISM: Artificial
<220> FEATURE:
<223> OTHER INFORMATION: Synthetic primer

<400> SEQUENCE: 3
ccgaccgtcc acccaaccat                                          20

<210> SEQ ID NO 4
<211> LENGTH: 20
<212> TYPE: DNA
<213> ORGANISM: Artificial
<220> FEATURE:
<223> OTHER INFORMATION: Synthetic primer

<400> SEQUENCE: 4
tctacctttc tttctatcta                                          20

<210> SEQ ID NO 5
<211> LENGTH: 20
<212> TYPE: DNA
<213> ORGANISM: Artificial
<220> FEATURE:
<223> OTHER INFORMATION: Synthetic primer

<400> SEQUENCE: 5
cacacactcg ctcgctcgct                                          20

<210> SEQ ID NO 6
<211> LENGTH: 20
<212> TYPE: DNA
<213> ORGANISM: Artificial
<220> FEATURE:
<223> OTHER INFORMATION: Synthetic primer

<400> SEQUENCE: 6
tccgacactt cattcatccg                                          20

<210> SEQ ID NO 7
<211> LENGTH: 20

```
<212> TYPE: DNA
<213> ORGANISM: Artificial
<220> FEATURE:
<223> OTHER INFORMATION: Synthetic primer

<400> SEQUENCE: 7
gccaaccagc cagcctgcct                                               20

<210> SEQ ID NO 8
<211> LENGTH: 20
<212> TYPE: DNA
<213> ORGANISM: Artificial
<220> FEATURE:
<223> OTHER INFORMATION: Synthetic primer

<400> SEQUENCE: 8
gcttacttac cagcctattt                                               20

<210> SEQ ID NO 9
<211> LENGTH: 20
<212> TYPE: DNA
<213> ORGANISM: Artificial
<220> FEATURE:
<223> OTHER INFORMATION: Synthetic primer

<400> SEQUENCE: 9
cacgcagacc actaatcaat                                               20

<210> SEQ ID NO 10
<211> LENGTH: 20
<212> TYPE: DNA
<213> ORGANISM: Artificial
<220> FEATURE:
<223> OTHER INFORMATION: Synthetic primer

<400> SEQUENCE: 10
tgcattcctg cgtgcgttcg                                               20

<210> SEQ ID NO 11
<211> LENGTH: 20
<212> TYPE: DNA
<213> ORGANISM: Artificial
<220> FEATURE:
<223> OTHER INFORMATION: Synthetic primer

<400> SEQUENCE: 11
ctaccgatcg accgaacgat                                               20

<210> SEQ ID NO 12
<211> LENGTH: 20
<212> TYPE: DNA
<213> ORGANISM: Artificial
<220> FEATURE:
<223> OTHER INFORMATION: Synthetic primer

<400> SEQUENCE: 12
ctatccagct agcaacgtag                                               20

<210> SEQ ID NO 13
<211> LENGTH: 20
<212> TYPE: DNA
<213> ORGANISM: Artificial
<220> FEATURE:
<223> OTHER INFORMATION: Synthetic primer

<400> SEQUENCE: 13
```

```
gctcactgac tgacagactg                                                    20

<210> SEQ ID NO 14
<211> LENGTH: 20
<212> TYPE: DNA
<213> ORGANISM: Artificial
<220> FEATURE:
<223> OTHER INFORMATION: Synthetic primer

<400> SEQUENCE: 14
cactcgagca agccagcgag                                                    20

<210> SEQ ID NO 15
<211> LENGTH: 20
<212> TYPE: DNA
<213> ORGANISM: Artificial
<220> FEATURE:
<223> OTHER INFORMATION: Synthetic primer

<400> SEQUENCE: 15
gacattgctg cgtacatgcg                                                    20

<210> SEQ ID NO 16
<211> LENGTH: 20
<212> TYPE: DNA
<213> ORGANISM: Artificial
<220> FEATURE:
<223> OTHER INFORMATION: Synthetic primer

<400> SEQUENCE: 16
tgcgtgtatc gagctacgta                                                    20

<210> SEQ ID NO 17
<211> LENGTH: 29
<212> TYPE: DNA
<213> ORGANISM: Artificial
<220> FEATURE:
<223> OTHER INFORMATION: Synthetic primer

<400> SEQUENCE: 17
ctgcaggtca gcctaacgtc aaaaagctt                                          29

<210> SEQ ID NO 18
<211> LENGTH: 29
<212> TYPE: DNA
<213> ORGANISM: Artificial
<220> FEATURE:
<223> OTHER INFORMATION: Synthetic primer

<400> SEQUENCE: 18
gacgtccagt cggattgcag tttttcgaa                                          29

<210> SEQ ID NO 19
<211> LENGTH: 31
<212> TYPE: DNA
<213> ORGANISM: Artificial
<220> FEATURE:
<223> OTHER INFORMATION: Synthetic primer

<400> SEQUENCE: 19
ctgcaggtca gcctaacgtc aactcaagct t                                       31

<210> SEQ ID NO 20
<211> LENGTH: 31
<212> TYPE: DNA
<213> ORGANISM: Artificial
```

```
<220> FEATURE:
<223> OTHER INFORMATION: Synthetic primer

<400> SEQUENCE: 20
gacgtccagt cggattgcag ttgagttcga a                              31

<210> SEQ ID NO 21
<211> LENGTH: 33
<212> TYPE: DNA
<213> ORGANISM: Artificial
<220> FEATURE:
<223> OTHER INFORMATION: Synthetic primer

<400> SEQUENCE: 21
ctgcaggtca gcctaacgtc aagtcgaaag ctt                            33

<210> SEQ ID NO 22
<211> LENGTH: 33
<212> TYPE: DNA
<213> ORGANISM: Artificial
<220> FEATURE:
<223> OTHER INFORMATION: Synthetic primer

<400> SEQUENCE: 22
gacgtccagt cggattgcag ttcagctttc gaa                            33

<210> SEQ ID NO 23
<211> LENGTH: 35
<212> TYPE: DNA
<213> ORGANISM: Artificial
<220> FEATURE:
<223> OTHER INFORMATION: Synthetic primer

<400> SEQUENCE: 23
ctgcaggtca gcctaacgtc aattcgacaa agctt                          35

<210> SEQ ID NO 24
<211> LENGTH: 35
<212> TYPE: DNA
<213> ORGANISM: Artificial
<220> FEATURE:
<223> OTHER INFORMATION: Synthetic primer

<400> SEQUENCE: 24
gacgtccagt cggattgcag ttaagctgtt tcgaa                          35

<210> SEQ ID NO 25
<211> LENGTH: 37
<212> TYPE: DNA
<213> ORGANISM: Artificial
<220> FEATURE:
<223> OTHER INFORMATION: Synthetic primer

<400> SEQUENCE: 25
ctgcaggtca gcctaacgtc acatcgacaa gaagctt                        37

<210> SEQ ID NO 26
<211> LENGTH: 37
<212> TYPE: DNA
<213> ORGANISM: Artificial
<220> FEATURE:
<223> OTHER INFORMATION: Synthetic primer

<400> SEQUENCE: 26
gacgtccagt cggattgcag tgtagctgtt cttcgaa                        37
```

<210> SEQ ID NO 27
<211> LENGTH: 53
<212> TYPE: DNA
<213> ORGANISM: Artificial
<220> FEATURE:
<223> OTHER INFORMATION: Synthetic primer

<400> SEQUENCE: 27
ctgcaggtca gcctaacgtc atatcgacaa ggtctgagtc agttctgaag ctt    53

<210> SEQ ID NO 28
<211> LENGTH: 53
<212> TYPE: DNA
<213> ORGANISM: Artificial
<220> FEATURE:
<223> OTHER INFORMATION: Synthetic primer

<400> SEQUENCE: 28
gacgtccagt cggattgcag tatagctgtt ccagactcag tcaagacttc gaa    53

<210> SEQ ID NO 29
<211> LENGTH: 59
<212> TYPE: DNA
<213> ORGANISM: Artificial
<220> FEATURE:
<223> OTHER INFORMATION: Synthetic primer

<400> SEQUENCE: 29
ctgcaggtca gcctaacgtc atttcgacaa ggtctgagtc agttctgagc agtaagctt    59

<210> SEQ ID NO 30
<211> LENGTH: 59
<212> TYPE: DNA
<213> ORGANISM: Artificial
<220> FEATURE:
<223> OTHER INFORMATION: Synthetic primer

<400> SEQUENCE: 30
gacgtccagt cggattgcag taaagctgtt ccagactcag tcaagactcg tcattcgaa    59

<210> SEQ ID NO 31
<211> LENGTH: 17
<212> TYPE: DNA
<213> ORGANISM: Artificial
<220> FEATURE:
<223> OTHER INFORMATION: Synthetic primer

<400> SEQUENCE: 31
gtcagcctaa cgtcaaa    17

<210> SEQ ID NO 32
<211> LENGTH: 17
<212> TYPE: DNA
<213> ORGANISM: Artificial
<220> FEATURE:
<223> OTHER INFORMATION: Synthetic primer

<400> SEQUENCE: 32
gtcagcctaa cgtcaac    17

<210> SEQ ID NO 33
<211> LENGTH: 17
<212> TYPE: DNA
<213> ORGANISM: Artificial
<220> FEATURE:
<223> OTHER INFORMATION: Synthetic primer

<400> SEQUENCE: 33
gtcagcctaa cgtcaag                                              17

<210> SEQ ID NO 34
<211> LENGTH: 17
<212> TYPE: DNA
<213> ORGANISM: Artificial
<220> FEATURE:
<223> OTHER INFORMATION: Synthetic primer

<400> SEQUENCE: 34
gtcagcctaa cgtcaat                                              17

<210> SEQ ID NO 35
<211> LENGTH: 17
<212> TYPE: DNA
<213> ORGANISM: Artificial
<220> FEATURE:
<223> OTHER INFORMATION: Synthetic primer

<400> SEQUENCE: 35
gtcagcctaa cgtcaca                                              17

<210> SEQ ID NO 36
<211> LENGTH: 17
<212> TYPE: DNA
<213> ORGANISM: Artificial
<220> FEATURE:
<223> OTHER INFORMATION: Synthetic primer

<400> SEQUENCE: 36
gtcagcctaa cgtcacc                                              17

<210> SEQ ID NO 37
<211> LENGTH: 17
<212> TYPE: DNA
<213> ORGANISM: Artificial
<220> FEATURE:
<223> OTHER INFORMATION: Synthetic primer

<400> SEQUENCE: 37
gtcagcctaa cgtcacg                                              17

<210> SEQ ID NO 38
<211> LENGTH: 17
<212> TYPE: DNA
<213> ORGANISM: Artificial
<220> FEATURE:
<223> OTHER INFORMATION: Synthetic primer

<400> SEQUENCE: 38
gtcagcctaa cgtcact                                              17

<210> SEQ ID NO 39
<211> LENGTH: 17
<212> TYPE: DNA
<213> ORGANISM: Artificial
<220> FEATURE:
<223> OTHER INFORMATION: Synthetic primer

<400> SEQUENCE: 39
gtcagcctaa cgtcaga                                              17

<210> SEQ ID NO 40

<211> LENGTH: 17
<212> TYPE: DNA
<213> ORGANISM: Artificial
<220> FEATURE:
<223> OTHER INFORMATION: Synthetic primer

<400> SEQUENCE: 40
gtcagcctaa cgtcagc                                                    17

<210> SEQ ID NO 41
<211> LENGTH: 17
<212> TYPE: DNA
<213> ORGANISM: Artificial
<220> FEATURE:
<223> OTHER INFORMATION: Synthetic primer

<400> SEQUENCE: 41
gtcagcctaa cgtcagg                                                    17

<210> SEQ ID NO 42
<211> LENGTH: 17
<212> TYPE: DNA
<213> ORGANISM: Artificial
<220> FEATURE:
<223> OTHER INFORMATION: Synthetic primer

<400> SEQUENCE: 42
gtcagcctaa cgtcagt                                                    17

<210> SEQ ID NO 43
<211> LENGTH: 17
<212> TYPE: DNA
<213> ORGANISM: Artificial
<220> FEATURE:
<223> OTHER INFORMATION: Synthetic primer

<400> SEQUENCE: 43
gtcagcctaa cgtcata                                                    17

<210> SEQ ID NO 44
<211> LENGTH: 17
<212> TYPE: DNA
<213> ORGANISM: Artificial
<220> FEATURE:
<223> OTHER INFORMATION: Synthetic primer

<400> SEQUENCE: 44
gtcagcctaa cgtcatc                                                    17

<210> SEQ ID NO 45
<211> LENGTH: 17
<212> TYPE: DNA
<213> ORGANISM: Artificial
<220> FEATURE:
<223> OTHER INFORMATION: Synthetic primer

<400> SEQUENCE: 45
gtcagcctaa cgtcatg                                                    17

<210> SEQ ID NO 46
<211> LENGTH: 17
<212> TYPE: DNA
<213> ORGANISM: Artificial
<220> FEATURE:
<223> OTHER INFORMATION: Synthetic primer

<400> SEQUENCE: 46
gtcagcctaa cgtcatt                                                17

<210> SEQ ID NO 47
<211> LENGTH: 37
<212> TYPE: DNA
<213> ORGANISM: Artificial
<220> FEATURE:
<223> OTHER INFORMATION: Synthetic primer

<400> SEQUENCE: 47
cagccgaacg accgagcgca gcgcagcgag tcagtga                          37

<210> SEQ ID NO 48
<211> LENGTH: 24
<212> TYPE: DNA
<213> ORGANISM: Artificial
<220> FEATURE:
<223> OTHER INFORMATION: Synthetic primer

<400> SEQUENCE: 48
ggccgattca ttaatgcagc tggc                                        24

<210> SEQ ID NO 49
<211> LENGTH: 46
<212> TYPE: DNA
<213> ORGANISM: Artificial
<220> FEATURE:
<223> OTHER INFORMATION: Synthetic primer

<400> SEQUENCE: 49
cctgcaggtc agcctaacgt cacctcgaca aggtctgagt cagttc                46

<210> SEQ ID NO 50
<211> LENGTH: 46
<212> TYPE: DNA
<213> ORGANISM: Artificial
<220> FEATURE:
<223> OTHER INFORMATION: Synthetic primer

<400> SEQUENCE: 50
cctgcaggtc agcctaacgt cacgtcgaca aggtctgagt cagttc                46

<210> SEQ ID NO 51
<211> LENGTH: 46
<212> TYPE: DNA
<213> ORGANISM: Artificial
<220> FEATURE:
<223> OTHER INFORMATION: Synthetic primer

<400> SEQUENCE: 51
cctgcaggtc agcctaacgt cacttcgaca aggtctgagt cagttc                46

<210> SEQ ID NO 52
<211> LENGTH: 46
<212> TYPE: DNA
<213> ORGANISM: Artificial
<220> FEATURE:
<223> OTHER INFORMATION: Synthetic primer

<400> SEQUENCE: 52
cctgcaggtc agcctaacgt cagatcgaca aggtctgagt cagttc                46

<210> SEQ ID NO 53
<211> LENGTH: 46
<212> TYPE: DNA

```
<213> ORGANISM: Artificial
<220> FEATURE:
<223> OTHER INFORMATION: Synthetic primer

<400> SEQUENCE: 53
cctgcaggtc agcctaacgt cagctcgaca aggtctgagt cagttc            46

<210> SEQ ID NO 54
<211> LENGTH: 46
<212> TYPE: DNA
<213> ORGANISM: Artificial
<220> FEATURE:
<223> OTHER INFORMATION: Synthetic primer

<400> SEQUENCE: 54
cctgcaggtc agcctaacgt caggtcgaca aggtctgagt cagttc            46

<210> SEQ ID NO 55
<211> LENGTH: 46
<212> TYPE: DNA
<213> ORGANISM: Artificial
<220> FEATURE:
<223> OTHER INFORMATION: Synthetic primer

<400> SEQUENCE: 55
cctgcaggtc agcctaacgt cagttcgaca aggtctgagt cagttc            46

<210> SEQ ID NO 56
<211> LENGTH: 46
<212> TYPE: DNA
<213> ORGANISM: Artificial
<220> FEATURE:
<223> OTHER INFORMATION: Synthetic primer

<400> SEQUENCE: 56
cctgcaggtc agcctaacgt catctcgaca aggtctgagt cagttc            46

<210> SEQ ID NO 57
<211> LENGTH: 46
<212> TYPE: DNA
<213> ORGANISM: Artificial
<220> FEATURE:
<223> OTHER INFORMATION: Synthetic primer

<400> SEQUENCE: 57
cctgcaggtc agcctaacgt catgtcgaca aggtctgagt cagttc            46

<210> SEQ ID NO 58
<211> LENGTH: 25
<212> TYPE: DNA
<213> ORGANISM: Artificial
<220> FEATURE:
<223> OTHER INFORMATION: Synthetic primer

<400> SEQUENCE: 58
ccctgcaggt cagcctaacg tcaaa                                   25

<210> SEQ ID NO 59
<211> LENGTH: 25
<212> TYPE: DNA
<213> ORGANISM: Artificial
<220> FEATURE:
<223> OTHER INFORMATION: Synthetic primer

<400> SEQUENCE: 59
ccctgcaggt cagcctaacg tcaac                                   25
```

<210> SEQ ID NO 60
<211> LENGTH: 25
<212> TYPE: DNA
<213> ORGANISM: Artificial
<220> FEATURE:
<223> OTHER INFORMATION: Synthetic primer

<400> SEQUENCE: 60
ccctgcaggt cagcctaacg tcaag          25

<210> SEQ ID NO 61
<211> LENGTH: 25
<212> TYPE: DNA
<213> ORGANISM: Artificial
<220> FEATURE:
<223> OTHER INFORMATION: Synthetic primer

<400> SEQUENCE: 61
ccctgcaggt cagcctaacg tcaat          25

<210> SEQ ID NO 62
<211> LENGTH: 25
<212> TYPE: DNA
<213> ORGANISM: Artificial
<220> FEATURE:
<223> OTHER INFORMATION: Synthetic primer

<400> SEQUENCE: 62
ccctgcaggt cagcctaacg tcaca          25

<210> SEQ ID NO 63
<211> LENGTH: 25
<212> TYPE: DNA
<213> ORGANISM: Artificial
<220> FEATURE:
<223> OTHER INFORMATION: Synthetic primer

<400> SEQUENCE: 63
ccctgcaggt cagcctaacg tcacc          25

<210> SEQ ID NO 64
<211> LENGTH: 25
<212> TYPE: DNA
<213> ORGANISM: Artificial
<220> FEATURE:
<223> OTHER INFORMATION: Synthetic primer

<400> SEQUENCE: 64
ccctgcaggt cagcctaacg tcacg          25

<210> SEQ ID NO 65
<211> LENGTH: 25
<212> TYPE: DNA
<213> ORGANISM: Artificial
<220> FEATURE:
<223> OTHER INFORMATION: Synthetic primer

<400> SEQUENCE: 65
ccctgcaggt cagcctaacg tcact          25

<210> SEQ ID NO 66
<211> LENGTH: 25
<212> TYPE: DNA
<213> ORGANISM: Artificial
<220> FEATURE:

```
<223> OTHER INFORMATION: Synthetic primer

<400> SEQUENCE: 66
ccctgcaggt cagcctaacg tcaga                                25

<210> SEQ ID NO 67
<211> LENGTH: 25
<212> TYPE: DNA
<213> ORGANISM: Artificial
<220> FEATURE:
<223> OTHER INFORMATION: Synthetic primer

<400> SEQUENCE: 67
ccctgcaggt cagcctaacg tcagc                                25

<210> SEQ ID NO 68
<211> LENGTH: 25
<212> TYPE: DNA
<213> ORGANISM: Artificial
<220> FEATURE:
<223> OTHER INFORMATION: Synthetic primer

<400> SEQUENCE: 68
ccctgcaggt cagcctaacg tcagg                                25

<210> SEQ ID NO 69
<211> LENGTH: 25
<212> TYPE: DNA
<213> ORGANISM: Artificial
<220> FEATURE:
<223> OTHER INFORMATION: Synthetic primer

<400> SEQUENCE: 69
ccctgcaggt cagcctaacg tcagt                                25

<210> SEQ ID NO 70
<211> LENGTH: 25
<212> TYPE: DNA
<213> ORGANISM: Artificial
<220> FEATURE:
<223> OTHER INFORMATION: Synthetic primer

<400> SEQUENCE: 70
ccctgcaggt cagcctaacg tcata                                25

<210> SEQ ID NO 71
<211> LENGTH: 25
<212> TYPE: DNA
<213> ORGANISM: Artificial
<220> FEATURE:
<223> OTHER INFORMATION: Synthetic primer

<400> SEQUENCE: 71
ccctgcaggt cagcctaacg tcatc                                25

<210> SEQ ID NO 72
<211> LENGTH: 25
<212> TYPE: DNA
<213> ORGANISM: Artificial
<220> FEATURE:
<223> OTHER INFORMATION: Synthetic primer

<400> SEQUENCE: 72
ccctgcaggt cagcctaacg tcatg                                25
```

```
<210> SEQ ID NO 73
<211> LENGTH: 25
<212> TYPE: DNA
<213> ORGANISM: Artificial
<220> FEATURE:
<223> OTHER INFORMATION: Synthetic primer

<400> SEQUENCE: 73
ccctgcaggt cagcctaacg tcatt                                          25

<210> SEQ ID NO 74
<211> LENGTH: 17
<212> TYPE: DNA
<213> ORGANISM: Artificial
<220> FEATURE:
<223> OTHER INFORMATION: Synthetic primer

<400> SEQUENCE: 74
gtcagcctaa cgttata                                                   17

<210> SEQ ID NO 75
<211> LENGTH: 17
<212> TYPE: DNA
<213> ORGANISM: Artificial
<220> FEATURE:
<223> OTHER INFORMATION: Synthetic primer

<400> SEQUENCE: 75
gtcagcctaa cgttcta                                                   17

<210> SEQ ID NO 76
<211> LENGTH: 17
<212> TYPE: DNA
<213> ORGANISM: Artificial
<220> FEATURE:
<223> OTHER INFORMATION: Synthetic primer

<400> SEQUENCE: 76
gtcagcctaa cgttacg                                                   17

<210> SEQ ID NO 77
<211> LENGTH: 17
<212> TYPE: DNA
<213> ORGANISM: Artificial
<220> FEATURE:
<223> OTHER INFORMATION: Synthetic primer

<400> SEQUENCE: 77
gtcagcctaa cgttccg                                                   17

<210> SEQ ID NO 78
<211> LENGTH: 44
<212> TYPE: DNA
<213> ORGANISM: Artificial
<220> FEATURE:
<223> OTHER INFORMATION: Synthetic primer

<400> SEQUENCE: 78
tgtaagcgtg aagacgacag aaagggcgtg gtgcggaggg cggt                    44

<210> SEQ ID NO 79
<211> LENGTH: 11
<212> TYPE: DNA
<213> ORGANISM: Artificial
<220> FEATURE:
<223> OTHER INFORMATION: Synthetic primer
```

```
<400> SEQUENCE: 79
accgccctcc g                                                          11

<210> SEQ ID NO 80
<211> LENGTH: 42
<212> TYPE: DNA
<213> ORGANISM: Artificial
<220> FEATURE:
<223> OTHER INFORMATION: Synthetic primer

<400> SEQUENCE: 80
ctctggcatc aactcggact atctcttcgt catctcacca ag                        42

<210> SEQ ID NO 81
<211> LENGTH: 13
<212> TYPE: DNA
<213> ORGANISM: Artificial
<220> FEATURE:
<223> OTHER INFORMATION: Synthetic primer

<400> SEQUENCE: 81
cttggtgaga tga                                                        13

<210> SEQ ID NO 82
<211> LENGTH: 21
<212> TYPE: DNA
<213> ORGANISM: Artificial
<220> FEATURE:
<223> OTHER INFORMATION: Synthetic primer

<400> SEQUENCE: 82
tgtaagcgtg aagacgacag a                                               21

<210> SEQ ID NO 83
<211> LENGTH: 21
<212> TYPE: DNA
<213> ORGANISM: Artificial
<220> FEATURE:
<223> OTHER INFORMATION: Synthetic primer

<400> SEQUENCE: 83
ctctggcatc aactcggact a                                               21

<210> SEQ ID NO 84
<211> LENGTH: 17
<212> TYPE: DNA
<213> ORGANISM: Artificial
<220> FEATURE:
<223> OTHER INFORMATION: Synthetic primer

<400> SEQUENCE: 84
ggtggcggga ggcgtgg                                                    17

<210> SEQ ID NO 85
<211> LENGTH: 17
<212> TYPE: DNA
<213> ORGANISM: Artificial
<220> FEATURE:
<223> OTHER INFORMATION: Synthetic primer

<400> SEQUENCE: 85
tatggcggga ggcgtgg                                                    17

<210> SEQ ID NO 86
<211> LENGTH: 17
```

<212> TYPE: DNA
<213> ORGANISM: Artificial
<220> FEATURE:
<223> OTHER INFORMATION: Synthetic primer

<400> SEQUENCE: 86
gggaaccact ctactgc                                              17

<210> SEQ ID NO 87
<211> LENGTH: 17
<212> TYPE: DNA
<213> ORGANISM: Artificial
<220> FEATURE:
<223> OTHER INFORMATION: Synthetic primer

<400> SEQUENCE: 87
tagaaccact ctactgc                                              17

<210> SEQ ID NO 88
<211> LENGTH: 17
<212> TYPE: DNA
<213> ORGANISM: Artificial
<220> FEATURE:
<223> OTHER INFORMATION: Synthetic primer

<400> SEQUENCE: 88
gtcagccgaa cgtcaaa                                              17

<210> SEQ ID NO 89
<211> LENGTH: 17
<212> TYPE: DNA
<213> ORGANISM: Artificial
<220> FEATURE:
<223> OTHER INFORMATION: Synthetic primer

<400> SEQUENCE: 89
gtcagccgga cgtcaaa                                              17

<210> SEQ ID NO 90
<211> LENGTH: 17
<212> TYPE: DNA
<213> ORGANISM: Artificial
<220> FEATURE:
<223> OTHER INFORMATION: Synthetic primer

<400> SEQUENCE: 90
gtcagcagga cgtcaaa                                              17

<210> SEQ ID NO 91
<211> LENGTH: 17
<212> TYPE: DNA
<213> ORGANISM: Artificial
<220> FEATURE:
<223> OTHER INFORMATION: Synthetic primer

<400> SEQUENCE: 91
gtcagaagga cgtcaaa                                              17

<210> SEQ ID NO 92
<211> LENGTH: 17
<212> TYPE: DNA
<213> ORGANISM: Artificial
<220> FEATURE:
<223> OTHER INFORMATION: Synthetic primer

<400> SEQUENCE: 92

-continued

```
gtcagaaggc cgtcaaa                                            17

<210> SEQ ID NO 93
<211> LENGTH: 17
<212> TYPE: DNA
<213> ORGANISM: Artificial
<220> FEATURE:
<223> OTHER INFORMATION: Synthetic primer

<400> SEQUENCE: 93
gtcagaatcc cgtcaaa                                            17

<210> SEQ ID NO 94
<211> LENGTH: 17
<212> TYPE: DNA
<213> ORGANISM: Artificial
<220> FEATURE:
<223> OTHER INFORMATION: Synthetic primer

<400> SEQUENCE: 94
gtcctaatcc agtcaaa                                            17

<210> SEQ ID NO 95
<211> LENGTH: 19
<212> TYPE: DNA
<213> ORGANISM: Artificial
<220> FEATURE:
<223> OTHER INFORMATION: Synthetic primer

<400> SEQUENCE: 95
agaattacgt gtaccaggg                                          19

<210> SEQ ID NO 96
<211> LENGTH: 18
<212> TYPE: DNA
<213> ORGANISM: Artificial
<220> FEATURE:
<223> OTHER INFORMATION: Synthetic primer

<400> SEQUENCE: 96
gaattacgtg taccagtt                                           18

<210> SEQ ID NO 97
<211> LENGTH: 19
<212> TYPE: DNA
<213> ORGANISM: Artificial
<220> FEATURE:
<223> OTHER INFORMATION: Synthetic primer

<400> SEQUENCE: 97
tgcagggtca tgggcccgc                                          19

<210> SEQ ID NO 98
<211> LENGTH: 11
<212> TYPE: DNA
<213> ORGANISM: Artificial
<220> FEATURE:
<223> OTHER INFORMATION: Synthetic primer

<400> SEQUENCE: 98
ggactattca c                                                  11

<210> SEQ ID NO 99
<211> LENGTH: 41
<212> TYPE: DNA
<213> ORGANISM: Artificial
```

<220> FEATURE:
<223> OTHER INFORMATION: Synthetic primer

<400> SEQUENCE: 99
ggactattca caccgaggta cggattacct gacgttaacg t                41

<210> SEQ ID NO 100
<211> LENGTH: 41
<212> TYPE: DNA
<213> ORGANISM: Artificial
<220> FEATURE:
<223> OTHER INFORMATION: Synthetic primer

<400> SEQUENCE: 100
acgttaacgt caggtaatcc gtacctcggt gtgaatagtc c                41

<210> SEQ ID NO 101
<211> LENGTH: 22
<212> TYPE: DNA
<213> ORGANISM: Artificial
<220> FEATURE:
<223> OTHER INFORMATION: Synthetic primer

<400> SEQUENCE: 101
cttcgagatc caacgttaac gt                                     22

<210> SEQ ID NO 102
<211> LENGTH: 12
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (11)..(11)
<223> OTHER INFORMATION: n = degenerate position

<400> SEQUENCE: 102
ggactattca na                                                12

<210> SEQ ID NO 103
<211> LENGTH: 53
<212> TYPE: DNA
<213> ORGANISM: Artificial
<220> FEATURE:
<223> OTHER INFORMATION: Synthetic primer

<400> SEQUENCE: 103
ggactattca caccgaggta cggattacct gacgttaacg ttggatctcg aag    53

<210> SEQ ID NO 104
<211> LENGTH: 53
<212> TYPE: DNA
<213> ORGANISM: Artificial
<220> FEATURE:
<223> OTHER INFORMATION: Synthetic primer

<400> SEQUENCE: 104
cttcgagatc caacgttaac gtcaggtaat ccgtacctcg gtgtgaatag tcc    53

<210> SEQ ID NO 105
<211> LENGTH: 21
<212> TYPE: DNA
<213> ORGANISM: Artificial
<220> FEATURE:
<223> OTHER INFORMATION: Synthetic primer

<400> SEQUENCE: 105
cggatctcaa agcttcgaga t                                                 21

<210> SEQ ID NO 106
<211> LENGTH: 65
<212> TYPE: DNA
<213> ORGANISM: Artificial
<220> FEATURE:
<223> OTHER INFORMATION: Synthetic primer

<400> SEQUENCE: 106
ggactattca caccgaggta cggattacct gacgttaacg ttggatctcg aagctttgag       60
atccg                                                                   65

<210> SEQ ID NO 107
<211> LENGTH: 65
<212> TYPE: DNA
<213> ORGANISM: Artificial
<220> FEATURE:
<223> OTHER INFORMATION: Synthetic primer

<400> SEQUENCE: 107
cggatctcaa agcttcgaga tccaacgtta acgtcaggta atccgtacct cggtgtgaat       60
agtcc                                                                   65

<210> SEQ ID NO 108
<211> LENGTH: 30
<212> TYPE: DNA
<213> ORGANISM: Artificial
<220> FEATURE:
<223> OTHER INFORMATION: Synthetic primer

<400> SEQUENCE: 108
ccacaatgcc cacatacagt ggactgcacc                                        30

<210> SEQ ID NO 109
<211> LENGTH: 30
<212> TYPE: DNA
<213> ORGANISM: Artificial
<220> FEATURE:
<223> OTHER INFORMATION: Synthetic primer

<400> SEQUENCE: 109
ggtgcagtcc actgtatgtg ggcattgtgg                                        30

<210> SEQ ID NO 110
<211> LENGTH: 24
<212> TYPE: DNA
<213> ORGANISM: Artificial
<220> FEATURE:
<223> OTHER INFORMATION: Synthetic primer

<400> SEQUENCE: 110
ccacaatgcc cacatacagt ggac                                              24

<210> SEQ ID NO 111
<211> LENGTH: 21
<212> TYPE: DNA
<213> ORGANISM: Artificial
<220> FEATURE:
<223> OTHER INFORMATION: Synthetic primer

<400> SEQUENCE: 111
cactgtatgt gggcattgtg g                                                 21

```
<210> SEQ ID NO 112
<211> LENGTH: 24
<212> TYPE: DNA
<213> ORGANISM: Artificial
<220> FEATURE:
<223> OTHER INFORMATION: Synthetic primer

<400> SEQUENCE: 112
ccacaatgcc cacatacatg cacc                                              24

<210> SEQ ID NO 113
<211> LENGTH: 24
<212> TYPE: DNA
<213> ORGANISM: Artificial
<220> FEATURE:
<223> OTHER INFORMATION: Synthetic primer

<400> SEQUENCE: 113
ggtgcatgta tgtgggcatt gtgg                                              24
```

COLLECTIONS OF UNIQUELY TAGGED MOLECULES

BACKGROUND AND SUMMARY OF THE INVENTION

This invention is directed to methods and kits for creating and analyzing molecules using uniquely identifiable tags. The invention is also directed to methods and kits that use uniquely identifiable tags for sequencing DNA, for determining mutations, including substitutions, deletions, and additions, in sample genes, and monitoring mRNA populations.

Biologists and chemists have long sought methods to identify a given molecule in a collection of thousands or millions or more of different molecular species. In large mixtures of many different molecules, it is challenging to identify any one molecule or molecular species rapidly. It is often even more difficult to identify several hundred or thousand non-identical or dissimilar species within a collection of many thousands or millions or more of different molecular species. It would be beneficial to functionally tag or "bar code" large numbers of molecular species for rapid, simultaneous identification.

To this end, the idea of using molecules to identify other molecules has emerged. As one example, it is now possible to use combinatorial synthesis techniques to develop large or extremely large collections of different but similar molecular species.

Combinatorial chemistry methods permit the synthesis of large numbers of different molecules in a mixture. In standard "pool and split" combinatorial methods, each molecule in the mixture is associated with a tag or series of tags helpful in determining the identity of the molecule to which the tag is attached. See, for example, Ohlmeyer, M. H. J., et al., "Complex Synthetic Chemical Libraries Indexed With Molecular Tags" Proc. Natl. Acad. Sci. 90:10922–10926, 1993; Pinilla, C., et al., "Versatility of Positional Scanning Synthetic Combinational Libraries for the Identification of Individual Compounds" Drug Devel. Res. 33:133–145, 1994; Gallop, M. A., et al. "Applications for Combinational Technologies to Drug Discovery. *1. Background and Peptide Combinational Libraries." J. Med. Chem. 37:1233–1251, 1994; Gordon, E. M., et al., "Applications of Combinational Technologies to Drug Discovery. 2. Combinational Organic Synthesis, Library Screening Strategies, and Future Directions." J. Med. Chem. 37:1385–1401, 1994; Janda, K. D., "Tagged Versus Untagged Libraries: Methods for the Generation and Screening of Combinational Chemical Libraries." Proc. Natl. Acad. Sci. 91:10779–10785, 1994; Dower, W. J., et al., PCT/US92/07815, WO 93/06121 "Method of Synthesizing Diverse Collections of Oligomers"; Matson, R. S. et al., U.S. Pat. No. 5,429,807, "Method and Apparatus for Creating Biopolymer Arrays on a Solid Support Surface"; Southern, E. M., et al., "Arrays of Complementary Oligonucleotides for Analyzing the Hybridization Behavior of Nucleic Acids." Nucl. Acids. Res. 22:1368–1373, 1994; Southern, E. M., "DNA Fingerprinting by Hybridization to Oligonucleotide Arrays." Electrophoresis 16:1539–1542, 1995; Drmanac, R. T. and Crkvenjakov, R. B., "Method of Determining an Ordered Sequence of Subfragments of a Nucleic Acid Fragment by Hybridization of a Oligonucleotide Probes" U.S. Pat. No. 5,492,806; Drmanac, R. T. and Crkvenjakov, R. B., "Method of Sequencing by Hybridization of Oligonucleotide Probes" U.S. Pat. No. 5,525,464; McGall, G. H., et al., "Spatially-Addressable Immobilization of Oligonucleotides and Other Biological Polymers on Surfaces" U.S. Pat. No. 5,412,087; Dower, W. J. and Fodor, S. P. A., "Sequencing of Surface Immobilized Polymers Utilizing Microfluorescence Detection" U.S. Pat. No. 5,547,839; Fodor, S. P. A., et al., "Array of Oligonucleotides on a Solid Substrate" U.S. Pat. No. 5,445,934; and Fodor, S. P. A., "Synthesis and Screening of Immobilized Oligonucleotide Arrays" U.S. Pat. No. 5,510,270. Typically, a combinatorial synthesis will proceed in "stages" with two or more reaction vessels per stage. The purpose of each reaction vessel is to add a unique chemical moiety to a growing collection of chemical compounds.

Each moiety is also associated with a uniquely identifiable "tag." The tag is typically attached to the same solid support to which the growing chemical compounds are attached. Thus, attachment of a tag to a solid support (typically a bead) conveys the information about the bead concerning the particular reaction vessel through which the bead has passed during the synthesis. In pool and split strategies, after the tags are attached in a particular stage, all of the reaction vessel contents are pooled, mixed, and divided and dispersed into new reaction vessels in the next stage. Each moiety added in each new reaction vessel will also be associated with a unique tag added to the beads. Thus, the collection of tag molecules on each bead conveys the "synthetic pathway" though which the particular bead was placed.

In standard screening of combinatorial chemistry libraries, information regarding the order of addition of the tags and the linkage of tags to one another is not needed. Combinatorial chemical libraries are typically screened in the hopes of finding a few members giving the strongest positive signals in the screening assay. The screens are typically performed in separate reaction wells, where one or a few members of the combinatorial library (one or a few beads) is placed in each well. If a particular member scores positively, the composition of the compound can be determined by looking at the tags that are attached to the bead to which the compound is (or was) attached. If one is examining the tags attached to only a single bead, then the synthetic pathway can be identified.

For example, suppose that in the construction of a particular combinatorial chemical library that there are four parallel chemical steps in each synthetic stage, and that there are four synthetic stages each linked by a pool and split step. If there are 16 uniquely identifiable tag molecules available, then each bead will have four tag molecules associated with it (corresponding to the four stages of chemical synthesis). Each tag molecule becomes a marker for each of the 16 reaction vessels. Any particular bead will have traveled through four of the reaction vessels during the procedure, and the four tag molecules that become associated with the bead will reveal the "synthetic pathway" of the bead provided that each bead is examined separately.

There are instances, however, in which it would be desirable to examine 100 positive beads together. If each bead contains four types of tag molecules and all of the tags are released from the beads and examined together, it will not be possible to determine the 100 different pathways that were used. Since there are only 16 different tag types, many pathways will use the same tag types in some but not all of their synthetic steps.

Thus, a primary difficulty in using such techniques lies in screening all of the species for those containing the desired activities or properties and then analyzing the molecular makeup of such species. To this end it has been proposed to use unique combinations of nucleotides to identify protein sequences that are constructed with combinatorial synthesis techniques. Brenner, S. & R. A. Lerner, "Encoded Combinatorial Chemistry," *Proc. Natl. Acad. Sci.* USA 89:5381–83 (June 1992). The Brenner method decodes the unique combinations of nucleotides by actually sequencing the nucleotide tags. Although this method may permit one to determine the identity of a large number of molecules in a combinatorial library, the method still requires the physical separation of the linked tags (oligonucleotides) themselves for individual analysis (by PCR and cloning followed by DNA sequencing). Thus, the method fails to identify a large subset of molecules simultaneously. It merely shifts the need from physical separation and isolation of the beads to physical separation and isolation (cloning) of amplicons. In addition, the Brenner method would not permit the use of tags as a substitute for traditional DNA sequencing methods, since the analysis of the tags relies on traditional DNA sequencing methods.

It has also been proposed that microelectronic devices can be used to identify particular species being built through combinatorial synthesis techniques. Nicolaou, K. C. et al., "Radiofrequency Encoded Combinatorial Chemistry," Angew. *Chem. Int. Ed. Eng.* 34:2289–91 (1995). These techniques, however, require the physical separation of the linked tags from one another prior to the decoding of the information the tags have encoded about the target molecules. Thus, these methods are not very useful to identify simultaneously a large subset of target molecules. A method that allows the simultaneous identification or analysis of large subsets of target molecules contained within a very large collection of similar or dissimilar molecules would greatly enhance the power, usefulness, speed, and/or ease of such identification or analysis.

Nucleic acids represent a particularly interesting collection of target molecules with which to apply the invention. Nucleic acids typically are found in nature as collections or sequences of nucleotides. DNA and RNA exist as linear sequences of nucleotides, and such sequences are typically found with other such sequences to make populations of nucleic acid sequences. For example, total cellular RNA comprises many types of RNA, including ribosomal, messenger, nuclear, and transfer RNA. Each such type comprises a collection of sequences. There are many different transfer RNA (tRNA) molecules corresponding to the various amino acids. There are many different messenger RNA (mRNA) molecules corresponding to the various genes of a species. DNA is also found as mixtures of nucleotide sequences. DNA from plants and animals is typically found as mixtures of chromosomes, which are linear sequences of nucleotides.

It is often difficult to study large collections of nucleic acid sequences because it is usually not easy to identify one nucleic acid molecule from another. It would be advantageous to be able to identify hundreds or more of non-homologous nucleic acid molecules simultaneously within collections of thousands or millions of nucleic acid molecules.

Different nucleic acid sequences can be different in molecular weight, and they sometimes can be resolved by electrophoresis, chromatography, or mass spectroscopy. However, different nucleic acid sequences are not always different in length or molecular weight. Different nucleic acid sequences are, by definition, different in the linear order of their nucleotides.

Probes can be created to distinguish one nucleotide sequence from many others. Such probes are known to be of protein, nucleic acid, or other synthetic chemical composition. For example, DNA and RNA binding proteins can recognize and bind to a specific sequence in a nucleic acid molecule. However, the number of such binding proteins is somewhat limited. Restriction enzymes can cleave nucleic acid molecules into fragments; yet this usually involves destruction of the molecules themselves, and nucleic acid molecules will not always have different "restriction maps" for a given set of restriction enzymes. Moreover, restriction mapping the naturally occurring restriction sites in a large set of different nucleic acid molecules simultaneously can be very difficult, if not impossible, due to redundancies in the map patterns.

Nucleic acids can be tagged with hapten molecules that can be recognized by antibody molecules. However, the number of available hapten/antibody sets is limited. Nucleic acid molecules can be tagged with fluorescent dyes. The number of known fluorescent dyes with non-overlapping visible emission spectra, however, is fairly small. Nucleic acid molecules can be tagged with radioactive markers, but the number of known independently distinguishable radioisotopes that can be functionally incorporated into nucleic acids is also small. Nucleic acids can be tagged with enzymes, but the number of known independently distinguishable enzymes that can be functionally incorporated into nucleic acids is also small. Any one of these detection strategies, acting independently, can be limited. As discussed below, an aspect of the present invention is to combine strategies to encode more information about the target nucleic acid sequences.

Two different techniques have been developed to try to screen target DNA populations by using complementary nucleic acid probe hybridization to form a specific duplex under conditions where non-complementary sequences usually will not form a duplex. For any given target nucleic acid, a nucleic acid probe molecule complementary to all or some of the target DNA can usually be synthesized chemically. If the sequence of the target is unknown, a large number of different nucleic acid probes can be synthesized. However, one must have a method to identify the nucleic acid probes being used to identify the nucleic acid targets. One of the two approaches has been to "bin" the different probes into different wells (test tubes) and to determine if a particular member of the target population can bind specifically to the probe molecule. This tedious method requires dispensing thousands of different probes into thousands of different bins and then testing the target nucleic acid population in each of the thousands of bins.

The second approach is an extension of the bin method, and uses a two-dimensional grid in place of the bins. See, e.g., Southern, E. M., et al., "Arrays of Complementary Oligonucleotides for Analyzing the Hybridization Behavior of Nucleic Acids." *Nucl. Acids. Res.* 22:1368–1373, 1994; Southern, E. M., "DNA Fingerprinting by Hybridization to Oligonucleotide Arrays." Electrophoresis 16:1539–1542, 1995; Drmanac, R. T. and Crkvenjakov, R. B., "Method of Determining an Ordered Sequence of Subfragments of a Nucleic Acid Fragment by Hybridization of a Oligonucleotide Probes" U.S. Pat. No. 5,492,806; Drmanac, R. T. and Crkvenjakov, R. B., "Method of Sequencing by Hybridization of Oligonucleotide Probes" U.S. Pat. No. 5,525,464; U.S. Pat. No. 5,412,087; and U.S. Pat. No. 5,445,934. In the gridding method, a relatively large number of nucleic acid probe molecules are synthesized on a two-dimensional solid support such that the coordinates or physical location (address) of the sample conveys its sequence identity. Since the probes are permanently attached to the solid support they can be exposed to the target nucleic acids simultaneously without the need for physical separation. Such gridding methods make it possible to display hundreds of thousands of probes to a target sample simultaneously.

The gridding method suffers from several limitations, however. If the probes are chemically synthesized, they are typically 20 nucleotides or shorter in length. It is not always trivial, however, to find conditions where only the desired short probe duplex will form without undesired duplexes forming. For example, nucleic acids that are rich in adenines and thymidines (A:T rich) do not form duplexes that are as stable as nucleic acids that are rich in guanines and cytosines (G:C rich) under the same reaction conditions. If the hybridization temperature is too high, certain A:T rich sequences will melt whereas G:C rich sequences will remain hybridized. However, if the temperature is lowered for A:T rich binding, certain G:C rich duplexes having some mismatched base pairs can form. Therefore, it is sometimes difficult to create a large collection of short, sequence-specific probes that will operate well together under a single set of conditions.

Longer probes can be created from biological sources or in vitro amplification strategies. These probes often do not suffer from the A:T/G:C content problem of some shorter probes, since the base content of sequences tends to average out over longer stretches. However, long probe grids are more expensive to make and, under their current configurations, often are not able to detect small changes (such as mutations) in the target nucleic acid sample. While short probes may detect such mutations by hybridization, they can only do so well if the particular mutations were anticipated, and the matrix was designed to detect them.

There are other limitations to two-dimensional grid analysis. The concentration of a probe available for interaction is limited by the amount of the probe that can be attached to the solid support. In addition, the target nucleic acids must diffuse to the probe since the bound probe cannot diffuse to the target nucleic acids. These factors diminish reaction rates and signal strength for such two-dimensional formats. These limitations may be obviated in a liquid phase hybridization system. In a liquid phase hybridization system, the concentration of the probe would not be limited by the solid support, both the target nucleic acids and the probes can diffuse toward each other, and signal amplification through cycling reactions could occur.

The present inventor is not aware of any current practical method to carry out and identify such multiple simultaneous hybridization reactions in liquid phase using a large collection of probes and targets. The lack of a rapid and effective way to specifically tag a large number of probes for subsequent identification hampers one from determining which probes successfully hybridize to target nucleic acid. The problems are compounded if a large collection of long probes is desired.

The present invention overcomes many of the limitations discussed above. Specifically, this invention permits the simultaneous identification of a large subset of target molecules out of a very large collection of similar or dissimilar molecular species. The present invention can be used to create tagged molecules that identify any collection of molecular species. For example, collections of peptides, antibodies, nucleic acids, or other chemical structures could be identified by tagged molecules using the methods described herein.

According to certain embodiments, the present invention provides an advantageous method to "bar code" collections of probes or analytes for use in a liquid phase hybridization reaction. In addition, certain embodiments of this invention provide tagged probes that are able to detect small changes or mutations in the target specimen. Certain embodiments of the present invention also permit such probes or analytes to detect the levels of a large number of different target species within a population of target species.

Specifically, in particular embodiments, this invention permits more rapid sequencing of large amounts of DNA than traditional DNA sequencing techniques. In other embodiments, this invention provides rapid identification of mutations, including substitutions, insertions, and/or deletions in target nucleic acid populations. The use of these embodiments to target genes, such as cancer or cystic fibrosis genes, would be useful in permitting a greater understanding of these disease states as well as identifying specific mutations present in any given individual. In other embodiments, this invention allows rapid monitoring of relative expression levels of a large population of mRNA molecules. This information would be valuable for assessing physiologic or disease states. For example, one can assess the dynamics of different cell types or cell states by analyzing relative mRNA concentrations. In yet other embodiments, the invention permits simultaneous and quick identification of many molecules produced in a combinatorial synthesis library without prior separation of the molecules or their tags.

In carrying out embodiments of the present invention, liquid phase detection can involve either short or long tagged nucleic acid probes or tags. According to embodiments that use the tags for identifying combinatorial synthesis molecules, the present invention employs unique molecular weights or unique lengths of the nucleic acid tags such that any number of molecules can be identified simultaneously and accurately without prior separation of each of the tags and/or molecules. Each weight or length will encode not only the identity of the building blocks used to make each molecule in the library, but also the order of synthesis used to make the molecule.

According to other embodiments, the invention provides methods of changing the genetic code of different nucleic acid sequences to another unique code for each unique sequence. The other unique code is designed such that it allows one to simultaneously and accurately determine the nucleic acid sequence without prior separation of the different nucleic acid sequences. The unique code is also called a tag.

In certain preferred embodiments, the unique code or tag can encode anywhere up to $4^{20}$ different sequences, which allows one to determine simultaneously any possible combination of sequences for up to 20 nucleotide stretches. Certain embodiments may also include encoding longer sequences.

According to certain embodiments, the unique tags are created using pool and split combinatorial synthesis methods. In contrast to traditional combinatorial synthesis, which creates random libraries of molecules, however, these embodiments use combinatorial synthesis to create specific tags. In other words, the combinatorial synthesis is used to translate the genetic code of different sequences in a sample into a different unique code that facilitates rapid identification of the nucleic acid sequences in the sample in a subsequent decoding step. That subsequent decoding step does not require separation of the different sequences before performing the decoding step, nor does it require one to separately determine each nucleotide of a sequence a single base at a time.

According to certain embodiments, the combinatorial split and pool tag synthesis employs nucleic acid amplification techniques, such as PCR. These techniques are used to selectively amplify particular tags being created based on a particular nucleic acid sequence in the sample. In other words, the amplification procedure allows one to create the new code on the tags in view of specific sequences being amplified in the sample.

In certain embodiments, the present invention employs a variety of different types of tags associated with a single probe or tagged nucleic acid. Thus, for example, a DNA probe can be used to encode the sequence of a target DNA fragment by a combination of tags including (but not limited to): differing base lengths of all or a portion of the probe; fluorescent dyes of different emission wavelengths; biotinylated (or other affinity molecules) attached to dideoxy nucleotides added to the probe by conventional primer extension reactions; and the pooling of probes with identical nucleotides at identical positions. Other different tags that can be used in combination with the tags above and/or each other include (but are not limited to): molecular weight of all or a portion of a nucleic acid tag or probe; specific order of bases of all or a portion of a tag or probe in general; specific sequences within a tag or probe recognized by binding proteins, restriction enzymes, or other proteins or chemical species; and specific sequences within a tag or probe that can be detected by mass spectroscopy or NMR. Other tagging molecules include (but are not limited to): hapten molecules; molecules identified by their size; fluorescent dyes; radioactive markers; enzymes; affinity reagents; radiofrequency microelectronic devices; atoms that create identifiable NMR spectra; binding energy or "melting temperature" when hybridized with other molecules; dissociation of duplexes formed with other molecules in response to an electric or magnetic field; and ionic residues that are charged or uncharged at various pH's. Another possible tag is segregation into discrete pools. In general, any property or item that is capable of being differentially detected can be used as a tag. In this manner, a variety of tags used in combination with a combinatorial labeling system can be used to exponentially expand the amount of information that can be encoded on a nucleic acid probe.

According to certain other embodiments, tags or probes that have already been prepared are provided in a kit that allows one to determine mutations, including substitutions, additions, deletions, or other changes in a known wild type nucleic acid sequence. These tags also employ an encoding scheme that changes the genetic code into another code that permits one to analyze short fragments of nucleic acid sequences without requiring one to sequence each nucleotide a single base at a time. The kits will permit the end-user to run one stage of primer extension in parallel with wild type test nucleic acid and with test nucleic acid and, then, to compare the products from those reactions on gels. That comparison will show specific differences between the wild type nucleic acid sequence and the test nucleic acid sequence. Those specific differences will allow the end-user to identify not only the identity of the specific changes (the identity of the changed nucleotide if it is a substitution or the identity of an added or deleted nucleotide), but also the location of the base changes in the nucleic acid sequence.

The tags or probes can be prepared using the techniques discussed above for the DNA sequencing procedures.

According to certain other embodiments, methods and kits are provided that allow the rapid analysis of mRNA or cDNA populations, which can reveal the relative concentrations of members of the populations. Again, the methods and kits utilize an encoding method that translates the genetic code into another unique code that permits simultaneous analysis of specific nucleic acid sequence fragments within a population of many different nucleic acid fragments. The tags or probes used in these embodiments can be prepared using the techniques discussed above for the DNA sequencing procedures.

BRIEF DESCRIPTION OF THE DRAWING FIGURES

FIG. 14 shows the arrangement of the 96-well PCR plate described in Example 7.

Figure 1:
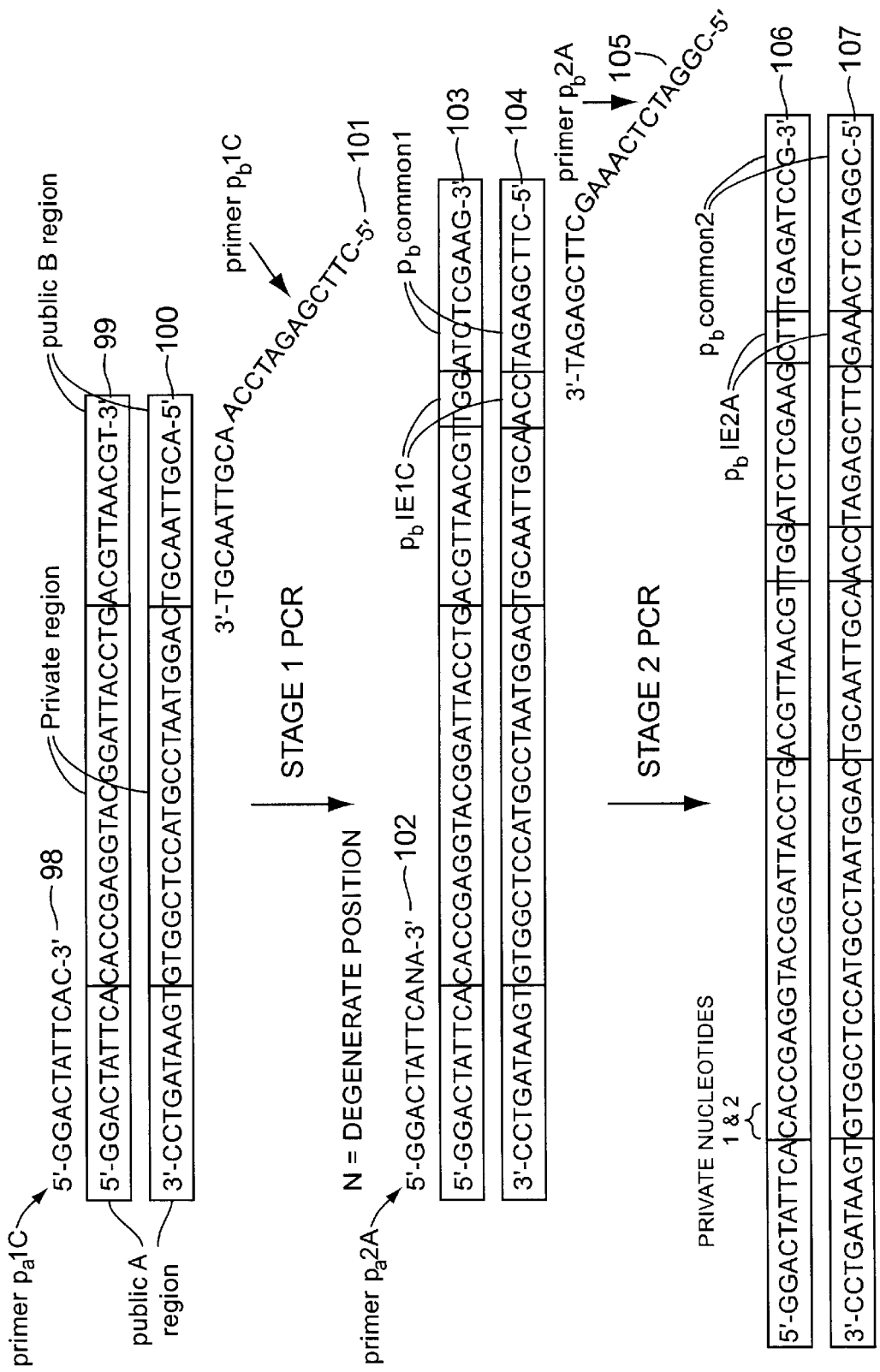
FIG. 1 shows a scheme for encoding information about a nucleic acid sequence with nucleotide tags using PCR.

FIG. 16 schematically represents the experiments conducted in Example 8.

DESCRIPTION OF THE PREFERRED EMBODIMENTS

Glossary of Terms

Encode/encoding: These terms are used herein in their general sense of converting information from one form into another instead of being limited only to their more specialized sense used with respect to DNA that encodes particular proteins.

Target: A molecule whose identity is sought or whose properties are to be analyzed in some way through application of this invention.

Read/Reading: Selectively or specifically processing information about a target.

Probe: A molecule that physically binds to a target or target subpopulation in a discriminating way. The probe reads the target or target subpopulation with specificity. In other words, the probe binds to a target or target subpopulation and discriminates whether there is sufficient binding above a threshold. In certain embodiments, PCR is used to amplify a DNA target. The probe is the primer sequence that selectively or specifically binds to the target sequence and discriminates whether there is sufficient binding for amplification to proceed. In certain embodiments, ligase chain reaction is used to amplify a DNA target. The probe in such embodiments selectively or specifically recognizes a substrate that is suitable for ligation and discriminates whether there is sufficient binding for amplification to proceed.

Tag: An atom, molecule, and/or physical or functional property used to encode information about a target or probe. Typically, a tag is associated with a probe, in a manner such that information about the target or target subpopulation that the probe is specifically reading is encoded. In certain embodiments, a tag may be physically attached to a probe. The tag is used to subsequently identify probes that have successfully bound to a target or target subpopulation to thus identify the identity of the appropriate target or target subpopulation.

Type IIS enzyme: An enzyme that cleaves at a position removed from the Type IIS enzyme recognition site. Examples of such enzymes are Bin 1, Bsa I, Eam 11041, Fok I, Mbo II, Mnl I. The following review article discusses Type IIS enzymes: Szybalski, W., S. C. Kim, N. Hasan and A. J. Podhajska "Class-IIS restriction enzymes-a review" (1991) Gene 100: 13–26.

Variable Position: A variable position on a molecule is a position that may be different from a counterpart position on another molecule. Examples of variable positions include, but are not limited to: amino acid residues of a peptide, polypeptide, or protein sequence; nucleotides of a nucleic acid sequence; or chemical substitutients on a chemical moiety (for example, a chemical ring structure optionally may have oxygen, sulfur, or nitrogen bonded to a particular position on that ring (the oxygen, sulfur, or nitrogen would be the variable position)).

Throughout this specification, many documents are cited. All of those documents are hereby specifically incorporated by reference.

Certain preferred embodiments of this invention use nucleic acids as probes because of the ease with which they can be made and manipulated, including, but not limited to, the ease with which they can be synthesized using combinatorial chemistry techniques, the ease with which they can be amplified, the ease with which they can be created in liquid phase and used in liquid phase to identify the target, and the ease with which they can be tagged or can themselves serve as tags in order to encode information about the target. Nucleic acids are preferred probes also due to the flexibility with which they can be applied to different targeting situations. Nucleic acids also are preferred in view of the variety of ways with which they can serve as tags.

More specifically, the use of nucleic acids as tags permits the use of DNA amplification techniques to encode information about either a target nucleic acid directly or a probe to be used in identifying and/or analyzing a target nucleic acid. Conventional DNA amplification techniques require the use of two different primers, one for each strand of a double-stranded DNA molecule to be amplified. It is possible to associate primers with each other such that one that specifically recognizes ("reads") one or more nucleotides in the target, or probe, or analyte nucleic acid sequence to permit amplification to occur while the same or other primer "encodes" or "reports" the read nucleotide(s) by adding specific tags to the amplified DNA. If target nucleic acids have been read, after all of the desired information is encoded, then the tags are decoded by appropriate means. In the case of probes, after all of the desired information is encoded, the probes are used to hybridize with target nucleic acids and then the tags are decoded by appropriate means, thereby indirectly providing information about the target nucleic acids.

Thus, preferred embodiments of this invention place the DNA sequence to be encoded (hereafter called the "private" sequences) between two primer binding regions or sites of known sequence (hereafter called "public" sequence). The portion of the DNA that contains the primer binding site that allows primers to read the unknown target nucleotides is arbitrarily called "region A," and the primers themselves are referred to as "pa". The portion of the DNA that contains the primer binding site that permits the encoding or recording of the identity of the unknown as nucleotides is called "region B," and the primers that bind to region B are themselves referred to as "pb".

It should be noted that in certain embodiments a single region can serve as the basis for identifying particular nucleotides in the private sequence and permitting the encoding of their identity. In this case, that region is arbitrarily referred to as A, and region B does not need to function other than by permitting DNA amplification to occur. It should be clear to one skilled in the art that sequence information can be encoded in pa primers as well as pb primers. For example, 16 different pa primers could bear 16 different 3' dinucleotides corresponding to private nucleotides 1 and 2. Each of these 16 primers could also contain independently distinguishable 5' ends. PCR products created from such primers could be mixed and then placed in second stage PCR reactions. The second stage pa primers (pa2 primers) could comprise unique dinucleotides at their 3' ends corresponding to private nucleotides 3 and 4, comprise degenerate or ambivalent positions corresponding with private nucleotides 1 and 2, and comprise unique 5' sequences that encode information with respect to private nucleotides 1 to 4. Degenerate primers would have sixteen different dinucleotides corresponding to private nucleotide positions 1 and 2 and sixteen different dinucleotides corresponding to positions 3 and 4. Thus, 256 (16×16) different pa2 primers would be needed. If the positions corresponding to private nucleotides 1 and 2 in the pa2 primers are ambivalent, one would only need 16 different pa2 primers for the sixteen different combinations of private nucleotides 3 and 4.

Ambivalent portions of primers will result in amplification of templates (target sequences) irrespective of the nucleotides corresponding to the ambivalent positions. See, for example, Guo, Z., Liu, Q., and Smith, L. M. "Enhanced discrimination of single nucleotide polymorphisms by artificial mismatch hybridization" (1997) Nature Biotechnology 15:331–335.

Any number of private nucleotides can be read and encoded in each stage according to several embodiments of the invention. As nonlimiting examples, in certain preferred embodiments, one could read and encode 1, 2, 3, 4, 5, or 6 or even slightly greater than 6 private nucleotides at a given stage. That number, however, may be well over 6.

In certain embodiments, specific recognition of previously read private nucleotides is important for subsequent reading steps and, thus, to preserve the proper discrimination by the polymerase, ambivalent portions of primers would not be used. Such embodiments include those in which previously read information is "passed on" in subsequent stages. Such embodiments are discussed in detail below.

Similar strategies could be used to "build" information into subsequent stage pa primers. Thus, the same primer that "reads" the private sequence can also encode such information.

As will be discussed below in more detail, including both the reading and encoding functions on a single primer will substantially reduce the number of vessels needed to accurately encode nucleotides at a given position. For example, if the pb primer encodes information, as discussed below, one typically must use a separate reaction vessel for each pb primer for each of the four possible nucleotides A, T, C, and G. If the pa primer encoded such information in addition to serving its reading function, one would not need such four way separation.

Encoding Nucleic Acid Sequences Through Use of DNA Amplification Techniques

Certain embodiments of the invention use a code transformation property to link tags to DNA fragments using nucleic acid amplification, preferably PCR. Although PCR is preferred, one may possibly use any nucleic acid amplification technique such as those discussed in PCT Published Patent Application No. WO 93/06121, e.g., at page 21, lines 9–14, and at the paragraph bridging pages 27 and 28. When using such nucleic acid amplification techniques according to certain embodiments of the invention, typically there should hybridization between two strands of nucleic acid such that a subsequent amplification will succeed or fail depending on the precision of the base pairing of the hybridization. In other words, one selectively amplifies a subpopulation of nucleic acids where the precision of the base pairing exceeds a threshold that allows amplification of that subpopulation. Thus, in PCR, the polymerase discriminates between the threshold level of mispairing permitted such that amplification proceeds if the threshold is met and does not proceed if the threshold is not met. As shown by certain embodiments discussed below, mispairing may or may not be permitted.

In ligase chain reaction, ligase discriminates between the threshold level of mispairing permitted such that amplification proceeds if the threshold is met and does not proceed if the threshold is not met. Typically, these DNA amplification techniques not only discriminate the threshold amount of mispairing permitted (if any), but also associate the appropriate tag element to encode information about the target or target subpopulation that is selectively amplified. The tags are subsequently used to identify the identity of the amplified target or target subpopulation of nucleic acids.

According to certain embodiments, a population of DNA molecules is created such that each individual DNA molecule in a population of DNA molecules or fragments is flanked by common primer binding sites (public regions A and B). For example, each DNA molecule in a population is flanked by primer binding sites A and B so that all of the molecules in the population could be exponentially PCR amplified using primers pa and pb. See, for example, Mullis, K., F. Faloona, S. Scharf, R. Saiki, G. Horn, and H. Erlich "Specific enzymatic amplification of DNA in vitro: the polymerase chain reaction" (1986) Cold Spring Harbor Symp. Quant. Biol. 51:263–273; Scharft, S. J., G. T. Hron and H. A. Erlich "Direct cloning and sequence analysis of enzymatically amplified genomic sequences" (1986) Science 233:1076–1078; and Andersson, M. A. Wentland, J. Y. Ricafrent, W. Liu and R. A. Gibbs "A 'double adaptor' method for improved shotgun library construction" (1996) Anal. Biochem. 236:107–113.

The distal nucleotides of the unique regions of the DNA fragments (private regions) are located immediately adjacent to the nucleotides that bind to the 3' ends of each primer (the primer binding sites are public, but the DNA between the primer binding sites A and B is unique and private to each molecular species).

Rather than using the pa primer to amplify any target DNA, one can "read" the first private nucleotide of the DNA fragments by constructing four different pa primers such that an additional nucleotide (A, T, G, or C) is added to the 3' end of each pa primer. In the first reaction, there are four separate reaction vessels. One includes the primer paA-3', the second includes primer paT-3', the third includes primer paG-3', and the fourth includes primer paC-3'. Thus, in the first vessel, only DNA fragments having T at the 3' end of the private region and complementary fragments having A at the 5' end of the private region can be exponentially amplified. In the second vessel, only DNA fragments having A at the 3' end of the private region and complementary fragments having T at the 5' end of the private region can be exponentially amplified. In the third vessel, only DNA fragments having C at the 3' end of the private region and complementary fragments having T at the 5' end of the private region can be exponentially amplified. In the fourth vessel, only DNA fragments having G at the 3' end of the private region and complementary fragments having C at the 5' end of the private region can be exponentially amplified. In this way, primer paA-3' is used to read a T at the 3' end of the private sequence of the strand to which paA-3' binds and an A at the 5' end of the strand complementary to the strand to which paA-3' binds.

Each of the four vessels also includes a unique pb primer that uniquely tags the particular amplified DNA fragments. Thus, the first vessel that has the primer paA-3' also has a unique pb primer that has a unique tag for fragments that have T at the 3' end of the private sequence that is read by paA-3'. The second vessel includes the primer paT-3' and a unique pb primer that has a unique tag for fragments that have A at the 3' end of the private sequence that is read by paT-3'. The third vessel includes the primer paG-3' and a unique pb primer that has a unique tag for fragments that has C at the 3' end of the private sequence that is read by paG-3'. The fourth vessel includes the primer paC-3' and a unique pb primer that has a unique tag for fragments that have G and the 3' end of the private sequence that is read by paC-3'. At the end of the reaction, each vessel will have amplified fragments having a private sequence with one of four nucleotides at the 3' end and such amplified DNA fragments will have unique tags corresponding to that nucleotide. Of course, the information encoding each of A, T, G, and C at the 3' end of the private fragments adjacent the A public region also provides encoding information corresponding to each of T, A, C, and G at the 5' end of the complementary strand.

The pb primer tag or modification can comprise a change in one or more non-destabilizing nucleotides in the pb primer, or the addition of new nucleotides to the 5' end of the pb primer. For instance, the length of the additional nucleotides will be different for each of the four nucleotides amplified in each of the four vessels. Typically a new additional common nucleotide sequence (pbcommon1) is added to the very 5' end of the new pb primers so that the resulting PCR amplified fragments can be amplified in parallel in subsequent PCR steps. (FIG. 1 shows the general scheme discussed here, except that the tagged information is shown as 3 nucleotide stretches called "pblE2C" and "pblE2A" in the figure rather than tags based on differing lengths. The term "pblE" when used in this application refers to specific tag elements that are used to encode information about the particular portions of the target that are being read. The number in the designation refers to the particular stage of the encoding steps.) In other words, even though the length of each unique tag is different, they will all share the same nucleotides at the 5' end. Such a common nucleotide sequence will permit the design of a primer in the next step that will recognize the common nucleotide sequence so that the first tag will be amplified in the subsequent reaction step discussed below.

In summary, in the first reaction step of these preferred embodiments, each of the four different pa primers will be used with one of four different modified pb primers. Four parallel PCR reactions are then carried out under conditions where each amplifies a subset of the original population of molecules, depending on the match between the first private nucleotide of the DNA molecule being read and corresponding 3' nucleotide of the particular pa primer. Such PCR amplified DNA subsets will be tagged with new and unique information by the particular pb primer and such tag will correspond to the private nucleotide immediately adjacent to the 3' end of the original pa primer. Another way of viewing this is that a single private nucleotide has been "sequenced" on every molecule in the original DNA fragment mixture, and such sequenced molecules have now been enriched and tagged with unique identifiers in the pb primer region.

The four PCR reactions are pooled, mixed, and then split into four new second stage reaction vessels. The new pools are once again PCR amplified. However, the pa primers for this second round of PCR amplification (pa2 primers) now comprise the sequence paNX-3' where N represents an equal mixture of all four nucleotides at the first private nucleotide position, pa represents sufficient sequence complementary to the pa primer binding site to allow specific priming, and X represents a single nucleotide (A, T, C, or G) at the second private nucleotide position specific for the particular PCR reaction vessel. Thus, each of the four second reaction vessels selectively will amplify fragments with a particular nucleotide (A, T, G, or C) at the second position of the private region. In addition, a new modified pb primer is added to each vessel. These pb2 primers will hybridize with all of the molecules in the newly added pbcommon1 public region on the 5' end of the first round pb1 primers, but will encode new nucleotides that will tag (encode) each molecule with unique information that reflects the identity of the second private nucleotide, which is the nucleotide read in the second stage reaction vessel in which the molecule was created.

The B region of the new PCR amplified fragments will now have two sets of information (two linked tags) that can be used to uniquely identify the pb tag and thereby uniquely identify the two private nucleotides immediately adjacent to the 3' end of the original pa primers. In a sense, the first two private nucleotides of every molecule in the original DNA population has been translated into a new code found in the new B region (linked tags).

According to certain embodiments, one can construct the B region such that there are 16 unique lengths (one for each possible combination of private dinucleotides, i.e., AT, AG, AC, M, TA, TG, etc.) between the 3' and 5' ends of the B region after two stages of PCR. If one has also placed a unique restriction site at the B region/private junction, then the B region can be isolated by cleavage with the appropriate restriction enzyme. Then, one can analyze all of the B region lengths by electrophoresis or mass spectroscopy and determine which two private dinucleotides were present adjacent to the region A/private region junction for all of the original DNA species in the original DNA population. Essentially this embodiment provides a sequence of the first two nucleotides of each private region adjacent to region A/private region junction.

Such a process can be repeated to gain additional sequence information by increasing the length of the tag. In addition, information can be acquired in dinucleotide, trinucleotide, or larger "bytes" simply by increasing the number of reaction vessels per stage and increasing the number of "test" nucleotides at the 3' end of each pa primer, provided that priming conditions are used that are selective or discriminating for the variable nucleotides at the 3' end of the primer. For example, sixteen reaction vessels could be used to obtain dinucleotide information in the private regions of the fragments. Each pa primer could contain two new 3' nucleotides, paX1X2-3'. Each of the sixteen reaction vessels would contain a different corresponding pb primer that would encode information related to the specific X1 and X2 nucleotides in that vessel. Three nucleotides of information could be acquired with 64 reaction vessels, 64 different pa primers of the type paX1X2X3-3', and 64 different pb primers.

According to certain preferred tagging methods, when one encodes private nucleotides at one or more positions by correlating the identity of the private nucleotides with specific sizes or molecular weights of the oligonucleotides, one can use the following type of table to assure that there are different sized tags for each possible nucleotide sequence. For example, if one wished to encode the sequences at four private nucleotide positions (arbitrarily designated as t1, t2, t3, and t4), the molecular weights of the tag molecules could be multiples of the numbers shown in Table 1, such that the sums of the molecular weights of any four tags, one selected from each row, would be independently and simultaneously identifiable:

TABLE 1

Example Tags

| | A | C | G | T |
|---|---|---|---|---|
| t1 stage | 1 | 2 | 3 | 4 |
| t2 stage | 4 | 8 | 12 | 16 |
| t3 stage | 16 | 32 | 48 | 64 |
| t4 stage | 64 | 128 | 192 | 256 |

Thus, for example, a tag set for the sequence AGGT would have an approximate molecular weight of k(1+12+48+256)= 317k, where k is some constant. The constant represents the molecular weight of the basic tag unit. For example, if the tag set comprised nucleotides, k would be approximately 330 Daltons (varying slightly depending on the particular nucleotide used.) The sequence TTTA would have the molecular weight k(4+16+64+64)=148k. The sequence MGC would have the molecular weight k(1+4+48+128)= 181k. Alternatively, the numbers in Table 1 can be the number of nucleotides for each tag such that each four nucleotide sequence will correlate to a nucleotide tag having a unique length. Thus, the sequence AGGT would be tagged with a nucleotide sequence of (1+12+48+256)=317 nucleotides. One could also add a constant number to the sum calculated from the table.

The numbers in Table 1 are derived by taking all of the 4-digit numbers in base four having only one non-zero digit. The T tag of each row is the same molecular weight multiple as the A tag of the next row, and the highest molecular weight multiple (256) is actually derived from the 5-digit base four number 10000.

Additionally, in creating a table any constant number may be added to any row of numbers, and the resulting molecular weights will also be unique. Variations can be created so that there are "gaps" between blocks of molecular weights by adding numbers to certain blocks within the table and multiplying other blocks appropriately. Essentially if the numbers are written in base four, it is possible to leave gaps in the base four sequence and just add more digits. Leaving molecular weight gaps can be useful if, for example, in a subsequent analysis step, the linked tags are cleaved to remove portions of the tags. The remaining linked tags may then migrate in the gap regions, which makes their identification easier. For example, the following set of numbers also produces 256 unique molecular weights when one tag is selected from each row:

TABLE 2

Example molecular weight tag multipliers with block gaps.

| | A | C | G | T |
|---|---|---|---|---|
| t1 stage | 1 | 2 | 3 | 4 |
| t2 stage | 4 | 8 | 20 | 24 |
| t3 stage | 16 | 48 | 80 | 112 |
| t4 stage | 64 | 192 | 320 | 448 |

This pattern places a block of 8 "gaps" between each block of 8 consecutive molecular weights. If there are N vessels in each stage of a combinatorial synthesis procedure, then a set of functional molecular weight multiples can be derived by writing the base N numbers having one non-zero digit. The highest molecular weight is derived from a base N number having S+1 digits, where S is the number of stages in the combinatorial synthesis. As with the base four example, there are multiple solutions to the table of molecular weight multiples for any given combinatorial synthesis scheme. The permitted combinations merely need to sum to unique numbers, whether written in base 10 or base N. As seen in Table 2, it is also possible to use base N numbers having more than one non-zero digit provided that the sums remain unique.

These tags can then be decoded by any appropriate method, including, but not limited to, mass spectroscopy, electrophoresis, or chromatography. Each of these methods could simultaneously determine the molecular weights or sizes of a large number of tags simultaneously.

In certain embodiments, after several stages of PCR reactions, the private region that has already been "sequenced" can present a challenge. For example if sequence information is being acquired in dinucleotide "bytes", private nucleotides 5 and 6 can be acquired with pa primers of the sequence paNNNNX1X2-3'. The four N's represent positions in the primer where all four nucleotides are represented in equal frequency. Another way to view this is that $4^4=256$ different pa primer types will be synthesized, each different in the NNNN region, and each of the 256 will have a specific X1X2 region. Since there will be 16 different X1X2 regions, each of these 16 combinations will be represented by 256 different primers (permuted through the NNNN region). After acquiring information about private positions 1 to 6, it might be possible to acquire information regarding private positions 7 and 8 by using pa primers of the sequence paNNNNNNX1X2-3'. This means, however, that each of the 16 different X1X2 primer pools will contain 4096 different primers permuted through the NNNNNN region. With 4096 different primers in each pool, each specific primer sequence is only present in $1/4096$ the concentration of the entire primer pool in any given vessel.

Figure 2:
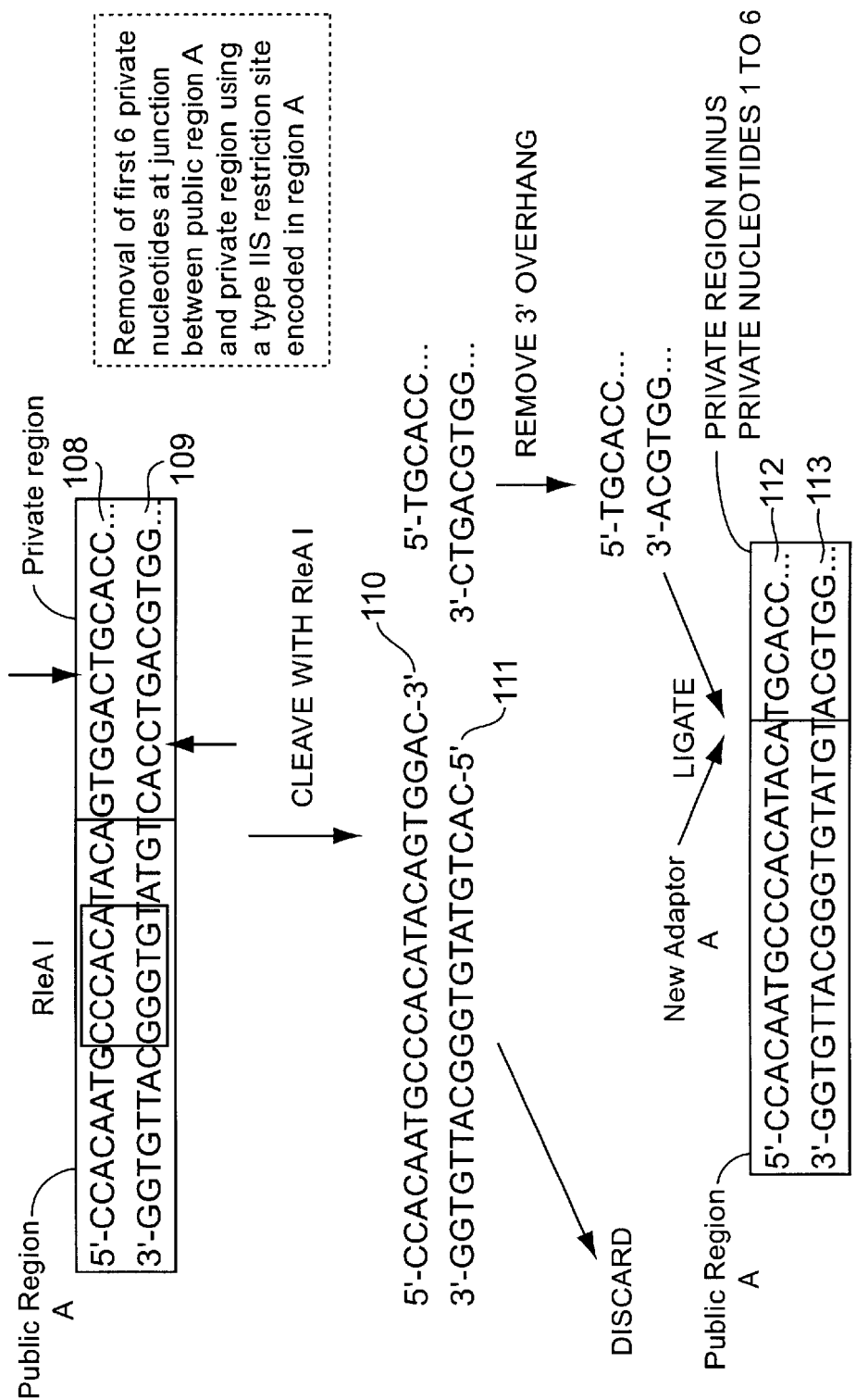
FIG. 2 shows a scheme for encoding extended nucleotides in a nucleic acid sequence by cleaving with a type IIS restriction enzyme.

At some point the efficiency of PCR priming will decrease due to dilution of template specific primer sequences in the pa primer pools. Thus, it might be desirable to remove "previously sequenced" private nucleotides from the DNA population before trying to acquire additional private nucleotide information. One way of accomplishing this is to encode a type IIS restriction site in the pa primer sequence such that cleavage with the associated restriction enzyme will remove the A region plus L nucleotides of private sequence, where L is defined by the specific type IIS restriction enzyme chosen. Type IIS restriction sites cause cleavage by associating restriction enzymes at a site displaced a set number of nucleotides away from the site. For example, a restriction site could be encoded in the A region such that 6 nucleotides of private region sequence could be removed by cleavage with the type IIS enzyme. See FIG. 2. Thus, all DNA fragments would be disassociated from the A region and also from 6 private nucleotides adjacent to the region A/private region junction. Such fragments could then be ligated with new A adaptors (for example, after creating blunt ends with a DNA polymerase such as Pfu DNA polymerase (Stratagene) (see also, Lundberg, K. S., D. D. Shoemaker, M. W. W. Adams, J. M. Short, J. A. Sorge, and E. J. Mathur "High-fidelity amplification using a thermostable DNA polymerase isolated from *Pyrococcus furiosus*" (1991) Gene 108:1–6; and Costa, G. L. and M. P. Weiner "Protocols for cloning and analysis of blunt-ended PCR-generated DNA fragments" (1994) PCR Methods and Appl. 3:S95–S106), and nucleotide triphosphates, if the type IIS enzyme does not leave blunt ends, or by ligating new A adaptors having a compatible overhang). The DNA fragments ligated with the new A adaptors could then be amplified with pa and pb primers to expand the population of DNA molecules. The new pa adaptors could also encode type IIS restriction sites so such a "trimming" procedure could be repeated as desired.

The primer-extension based strategies described above work best when the DNA polymerase is capable of distinguishing perfectly matched primer 3' ends from mismatched primer 3' ends. In the dinucleotide approach with 16 parallel PCR reactions, the polymerase should be able to discriminate all dinucleotide mismatches. According to certain embodiments, such discrimination is accomplished by varying conditions of the PCR reactions. For example, one can optimize such discrimination by using different temperature variations (for example higher temperatures for the initial rounds of PCR, which gradually are reduced for each subsequent round until a minimal temperature is reached for many subsequent rounds of PCR). This technology includes various "TouchDown" techniques. Such optimization may also be accomplished by delaying the combination of all of the requisite materials until a threshold temperature is reached for the first round of PCR. This technology includes various "HOT START" techniques. Such optimization may also be accomplished by varying the concentration of dNTP. Such conditions may be different depending on the size of the primers and the number of variant nucleotides that one is trying to read without mismatches in a given PCR reaction. Specific variations in the parameters for PCR reactions are discussed below.

One skilled in the art will be capable of constructing the pa and pb primers. Particular methods of making longer pb primers are discussed in more detail below.

Information about the target molecule can be encoded by using oligonucleotides in numerous different ways. For example, oligonucleotides can encode information by such properties as molecular weight, size, melting temperature, binding energy, or isoelectric points. Each of these properties can then be decoded by rapid, simultaneous analysis without the need to physically separate and amplify the tags one from another prior to performing the analysis, as opposed to classical DNA sequencing methods which require such isolation prior to analysis.

For example, another way to use oligonucleotides as tags to encode information about a target molecule would be to create tags (as opposed to the probe molecules themselves) that could be recognized by proteins, nucleic acids, or other affinity reagents. For example, suppose that each moiety of the probe or target is encoded by a linked tag comprised of a dinucleotide. For instance, suppose that for a given synthetic stage, moiety 1 is encoded by AC; moiety 2 is encoded by CA; moiety 3 is encoded by GT; and moiety 4 is encoded by TG. This particular dinucleotide code balances out the A:T/G:C content in the new code. The doublet code tag can be detected under suitable conditions that will also be suitable for other members of the doublet tag population (for example by hybridization at a fixed temperature). The important concept is that combinatorial synthesis procedures allow the probe or target sequence code to be encoded by a second tag code which might have properties that facilitate rapid detection. If the probe were a collection of long mononucleotide sequences having locally biased A:T/G:C content, the tag collection could be short dinucleotide sequences having balanced A:T/G:C content. Thus, subsets of the probe-tag collections could be examined quickly with oligonucleotide grids specific for the A:T/G:C balanced dinucleotide tag codes. This balancing of the A:T and G:C content remedies any difficulty that may be encountered with unbalanced A:T or G:C rich regions that was discussed above.

Figure 3:
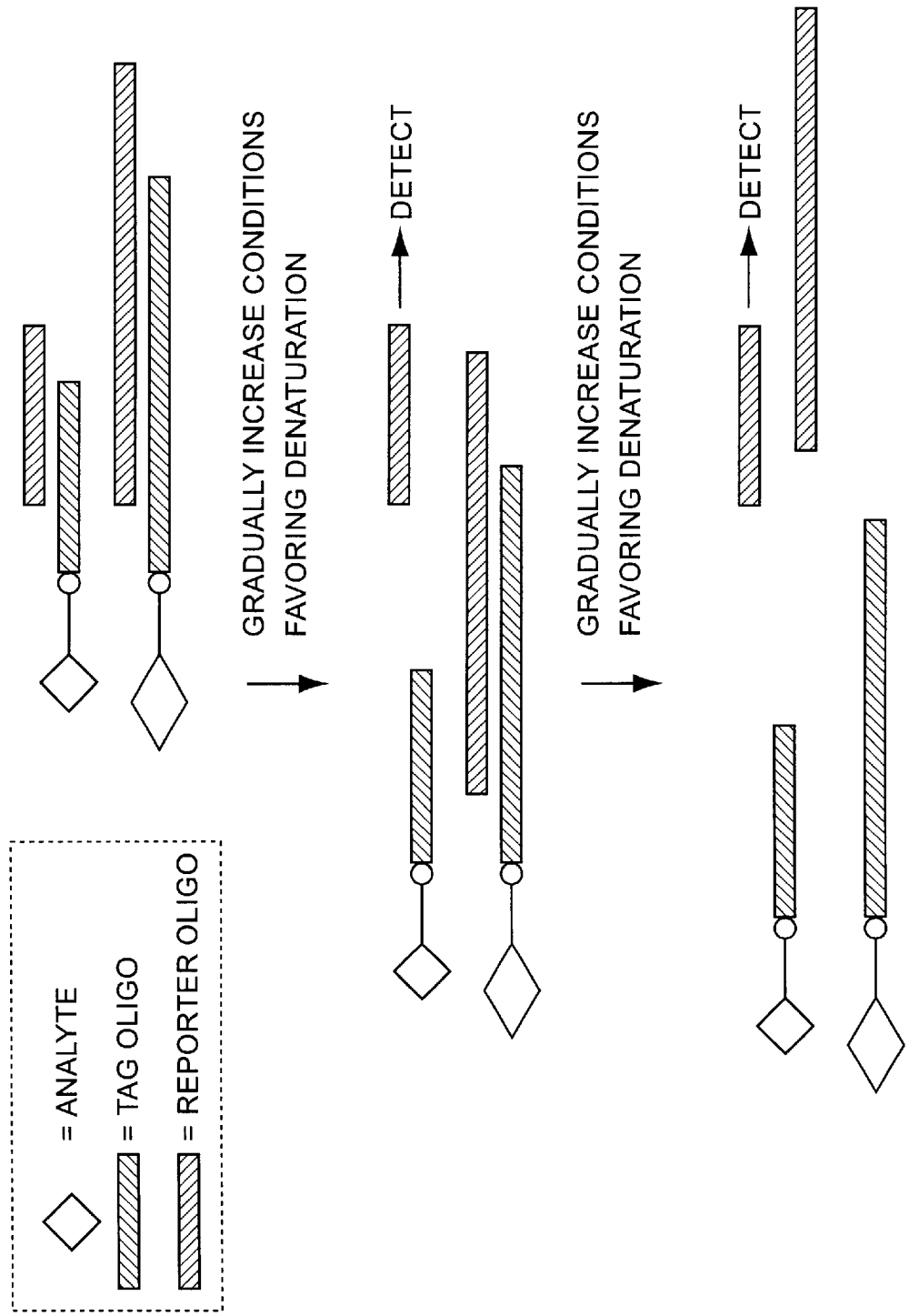
FIG. 3 shows a scheme for determining an analyte using oligonucleotide tags and a complementary reporter oligonucleotide.

Oligonucleotide tags could also be identified by their binding energy or "melting temperatures" when hybridized with other molecules. An oligonucleotide tag that is operatively linked to an analyte could hybridize with a complementary "reporter" oligonucleotide. See FIG. 3, which generally represents the scheme discussed here. For this discussion, an analyte is defined as a probe being used to interact specifically with the target material. Such a hybridized complex or collection of hybridized complexes could then be placed in a chamber that is exposed to increasing temperature, or other changes in conditions that result in disassociation of the hybridized complexes (changes in properties or concentration of a disassociating agent). Such other changes include, but are not limited to, increasing concentration of denaturant, changes in pH, changes in hydrophobicity, or changes in ionic strength. Those skilled in the art are familiar with changing disassociating conditions that can include, e.g., use of agents such as urea and formamide. Such conditions may be changed individually or together. At some point, the duplex DNA will "melt" and the reporter oligonucleotide would disassociate from the analyte-tag oligonucleotide complex. If the reporter oligonucleotide were in a flow stream or in an electric field it could be carried away from the analyte-tag oligonucleotide which could be tethered or trapped so that it could not move in the flow stream or in the electric field. The reporter oligonucleotide would melt from the analyte-tag oligonucleotide at a reproducible temperature and/or other denaturing condition. Thus, the appearance of a dissociating reporter oligonucleotide at a particular temperature and/or other denaturing condition would indicate that a known tag oligonucleotide sequence was present in the chamber.

Since each known tag oligonucleotide would be associated with a particular analyte sought, a large collection of analyte-tag oligonucleotides could thus be monitored to determine which members of the collection were present in a chamber as follows: one takes a library of single stranded analyte-tag oligonucleotides and hybridizes the tag oligonucleotides with their complementary reporter oligonucleotides. (Through prior experimentation one can determine the conditions at which each reporter oligonucleotide will dissociate from a given tag oligonucleotide.) One then reacts the analytes with their target(s) to select for a target or analyte subpopulation of interest. Here, an analyte selectively reacts with a particular target. For instance, an analyte could include a particular DNA sequence that hybridizes to a particular target sequence. One would need to design the analyte such that the sequence that hybridizes to the target does not hybridize to the reporter oligonucleotide. One washes away the population that does not react with the target(s).

To accomplish this washing step according to certain embodiments, the targets could be coupled to an affinity moiety, such as a biotin or a hapten. The target-analyte-tag-reporter complexes thus could be separated from the analyte-tag-reporter complexes that are not bound to targets.

Another way to accomplish this is to confine the target-analyte-tag-reporter oligonucleotide complexes to a chamber (there are numerous ways to accomplish this, such as by using a chamber that has an immobilized affinity reagent that reacts with a second affinity reagent included on all target-analyte-tag complexes, or by restraining the movement of these complexes because they may be bound to beads). One then causes a fluid to flow through the chamber or places the liquid in the chamber under an electric or magnetic field. One then gradually raises the temperature and/or denaturing conditions of the chamber and the fluid in (flowing through) it. At certain temperatures and/or other denaturing conditions, certain reporter oligonucleotides will melt away from their respective target-analyte-tag oligonucleotide complexes and be drawn away by the flow stream or by the electric or magnetic field. Such reporter oligonucleotides may then be detected. By correlating the time of detection with the chamber temperature and/or other denaturing conditions at that time, the sequence of the particular reporter oligonucleotide can be determined, provided that the individual melting temperatures or denaturing conditions of the reporter oligonucleotides are different and distinguishable. Knowing the sequence of particular reporter nucleotides, one can deduce the analytes, and thus, the targets in a given sample. This decoding step can be performed without prior separation of each of the retained unique analyte-tag oligonucleotides from each other after reaction with the target.

Figure 4:
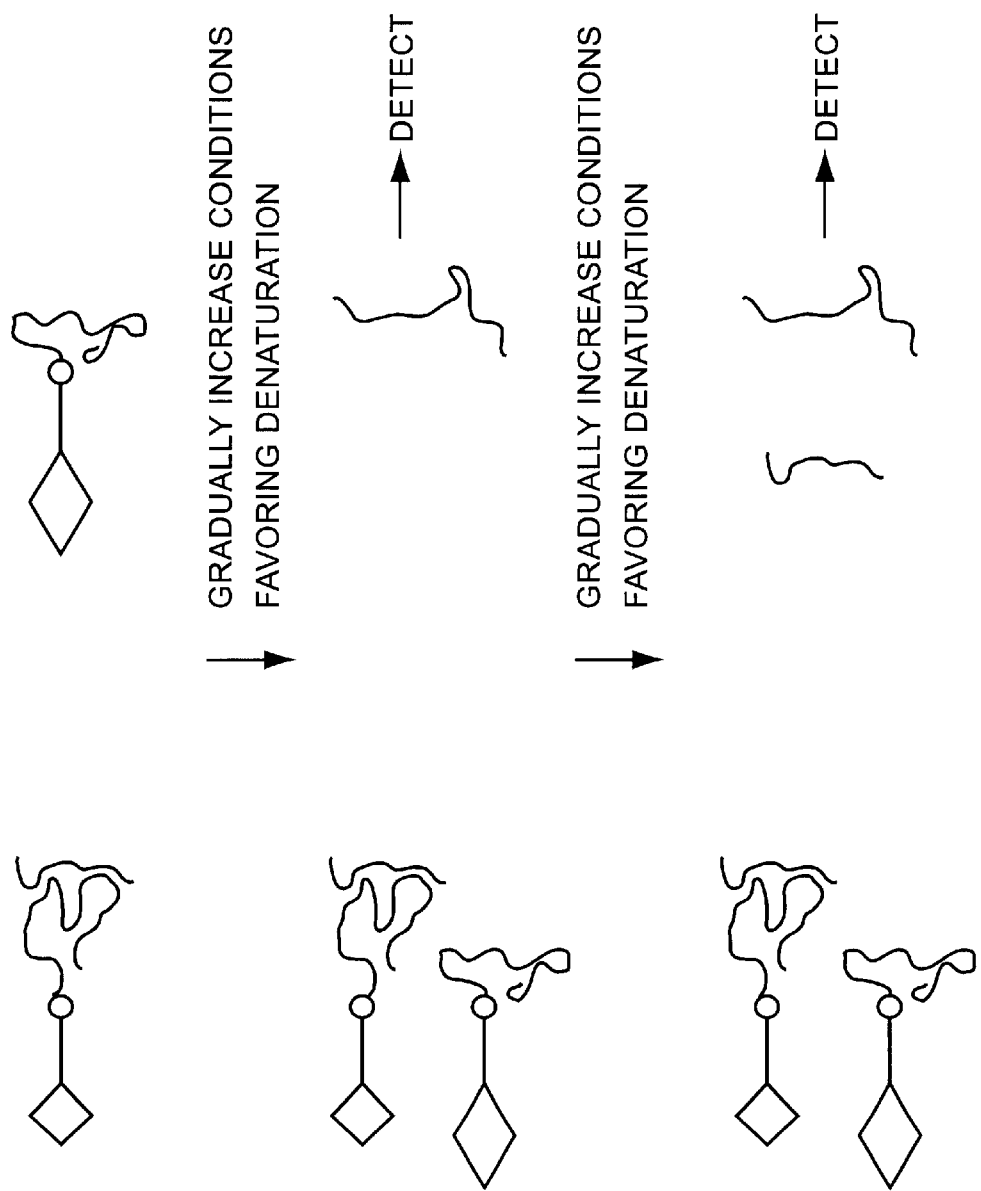
FIG. 4 shows a scheme for determining an analyte using oligonucleotide tags and a complementary reporter oligonucleotide, in which the oligonucleotide tags are not perfectly hybridized to the reporter oligonucleotides.

The reporter oligonucleotides need not be perfectly hybridized with the tag oligonucleotides. In fact, secondary structure in each oligonucleotide and interrupted stretches of hybridizing bases could contribute to a greater spectrum of melting temperatures and/or other denaturing conditions within the population. See FIG. 4.

Melting or denaturation temperature is not the only variable that could be used to separate the reporter molecules from the tag molecules (neither of these molecules needs to be an oligonucleotide—oligonucleotides are exemplary only). For example, hydrocarbons of varying chain length or hydrophobicity could be used. An electric and/or magnetic field could be applied such that increasing the field could begin to cause certain duplexes to disassociate at different field strengths. If the particular field strengths at which different complexes dissociate are known, then such knowledge could be used to predict which complexes are present in a complex mixture that is being exposed to gradually increasing field strength. Magnetic fields could be used for such purposes if the reporters were coupled to substances that respond to magnetic fields. See, e.g., Baselt et al., "A biosensor based on force microscope technology," J. Vac. Sci. Technol., B 14(2), pp. 789–793 (April 1996). Baselt et al. also illustrates the use of atomic force microscopy, which may also be used according to certain embodiments to identify uniquely identifiable molecular compositions used as encoding elements.

The tags used in these embodiments may also be referred to as base subunits, since they hold the reporter molecule (reporter subunit) until a uniquely identifiable condition causes them to dissassociate. The base subunits may also be other materials such as amino acid residues of varying length and isoelectric point or other materials that can have a unique association with reporter subunits. Proteins, nucleic acids, or other affinity reagents that recognize the tags comprise reporter subunits. A base subunit is identified by its association with and subsequent dissociation from a reporter subunit. Conditions under which the base and reporter subunits associate and disassociate are unique and identifiable.

Known, calibrating reporter molecules could be included in the complex mixture so that particular temperatures or denaturant concentrations or field strengths can be measured not just at the source but also indirectly by the appearance of calibrating reporter molecules. For example, reporter molecules coupled to a fluorescent molecule could act to identify certain melting points provided that the fluorescent molecule were unique to the calibrating population.

Throughout the discussion above, the use of disassociating conditions has been discussed for unique identification by disassociating molecules. This invention also includes embodiments in which association is used to identify molecules. Thus, rather than vary conditions to achieve disassociation of molecules at unique conditions, one may vary conditions that result in association of molecules at unique conditions. In such embodiments, one could detect the unique conditions at which association occurs.

Another method for creating a large population of independently identifiable tags is to give such tags ionic residues such that they will either be charged or uncharged at various pH's. For example, amino acids have side groups that can be charged or uncharged at various pH's. A protein will have an "isoelectric point"—a pH at which the protein charge is neutral. If the pH is raised or lowered, the protein will gain either positive or negative charge. If a collection of different proteins are placed in a pH gradient which is also placed under an electric field, each protein can be "focussed" by migration to its isoelectric pH. The combinatorial tag population could be synthesized so that each tag or tag family had a different isoelectric point. In this way, the tags could be separated in an additional dimension.

For example, proteins can be examined on "two-dimensional gels". The proteins are first focussed to migrate to their isoelectric pH's in a pH gradient. The gradient is then placed orthogonal to an electric field that draws the focussed proteins through a size separation gel. If the tag population were synthesized so that they first could be focussed by pH or some other means, and then size separated, many more tags could be identified simultaneously. One dimension would be size or molecular weight, as described above, and another dimension could be some type of focussing. For example, modified tag oligonucleotides could be synthesized so that they contained charged groups attached to the bases. Such oligonucleotides could be pH focussed just like proteins and separated in two dimensions. Such two-dimensional analysis could exponentially increase the number of independently identifiable tags that could be detected. Other properties could be used for separation, such as hydrophobicity, charge to mass ratio, or magnetic responsiveness.

The following references discuss the use of proteins as tags, including attachment of the proteins: Dower, W. J. and Fodor, S. P. A., "Sequencing of Surface Immobilized Polymers Utilizing Microfluorescence Detection" U.S. Pat. No. 5,547,839; Fodor, S. P. A., et al., "Array of Oligonucleotides on a Solid Substrate" U.S. Pat. No. 5,445,934; Fodor, S. P. A., "Synthesis and Screening of Immobilized Oligonucleotide Arrays" U.S. Pat. No. 5,510,270; and PCT Published Patent Application WO 96/12014 (Brenner). Typically, when proteins are used as tags, the target is separated from the tag proteins prior to decoding steps.

For the oligonucleotide tags discussed above, which are used in combination with nucleic acid amplification techniques, any type of information may be stored in the B region. As shown above, the B regions can be varied in length, such that the length corresponds with information in the private region of the DNA molecules. Additional information can be decoded by length measurements by selectively placing restriction sites in the B region. For example, if a particular nucleotide in the private region is being selectively amplified with a pa primer, the corresponding pb primer for such an amplification can include a restriction site which is placed a known distance from one or the other end of the B region. If there are four parallel vessels each of which is selectively amplifying a subpopulation encoding a different private nucleotide, the corresponding pb primers can be designed to comprise a restriction site placed in a predetermined location which corresponds to the particular private nucleotide-encoding fragments being selectively amplified in the particular reaction vessel.

Subsequent analysis of such fragments can include cleaving the DNA with the restriction enzyme whose targets are now encoded in pb followed by molecular weight or size determination, or the restriction digestion could be performed after one separation, but prior to another separation. Comparison of the B region lengths and/or weights prior to and after restriction enzyme cleavage will reveal information about sequences in the private region. For example, the final pb primers can be labeled with fluorescent reporter molecules such as fluorescene, rhodamine, or bodipy (Molecular Probes Co. (Eugene, Oreg.) derivatives at their 5' ends. The DNA can then be cleaved at a common restriction site located at the region B/private region junction of all DNA fragments. The DNA can also be cleaved at a specific restriction site encoded in the pb internal sequence depending on the particular nucleotide that was selectively amplified. The degree to which the B region DNA was shortened by cleaving at the internally encoded restriction site will convey information about private sequences in the DNA molecules. In order to accomplish this, it is important to be able to trace the change in size of the DNA fragments prior to and after cleavage at the internally encoded pb restriction sites.

One example of a way to accomplish this would be tagging the pb primers with fluorescent molecules of different emission wavelengths. The "color" of the tag can then be used to trace the change in molecular weight pre- and post-cleavage. For example, the B region lengths encoded in Table 1 can be used to generate 256 different amplified populations such that four private nucleotides of each molecule are encoded by the length of the B region. Each of four possible nucleotides at a single position within the encoded private region can also be encoded by a fluorescent color. For example, the t1 stage shown in Table 1 could be correlated with four different colored pb primers. Thus, a B region fragment of length 256 might be red; length 255 might be blue; length 254 might be green; length 253 might be yellow; length 252 might be red; length 251 might be blue; and so forth in succession.

After cleaving such DNA molecules at a restriction site located at the pb region/private region junction, electrophoresis of such molecules will reveal information regarding four of the private nucleotides of each member of the DNA population. The color of each band will add no additional information, but will confirm the identity of one of the private nucleotides. However, if a restriction site were encoded internally in the pb regions corresponding to an additional fifth private nucleotide, then cleaving the DNA at the internal restriction site would reduce the size of the fragments. If the internal restriction site were designed to reduce the size of all molecules by a fixed number of nucleotides, plus one, two, three, or four nucleotides, corresponding with the identity of a fifth private nucleotide, then it will be possible to map reductions in band size. For example, a red band will be reduced by F+R nucleotides, where F is a fixed number of nucleotides for all fragments and R is between 1 and 4 nucleotides. In this way, one red band, for example, will never be superimposed on another red band, and thus it will be possible to map the reduction in size of all red bands. The same will be true for the other colors.

For instance, in the example above, one could assign a fixed number of 10 nucleotides, and R for the fifth private nucleotide A could be 1, R for the fifth private nucleotide T could be 2, R for the fifth private nucleotide G could be 3, and R for the fifth private nucleotide C could be 4. Thus, the restriction site for A at the fifth position would result in an enzyme cleaving off 11 nucleotides of the pb primer. The restriction site for T at the fifth position would result in an enzyme cleaving off 12 nucleotides of the pb primer. The restriction site for G at the fifth position would result in an enzyme cleaving off 13 nucleotides of the pb primer. The restriction site for C at the fifth position would result in an enzyme cleaving 14 nucleotides of the pb primer.

If the initial length of the pb primer encoding the first four private nucleotides were 256 nucleotides (encoding private nucleotides 1 to 4 TGGG), the pb primer would be red. If the fifth nucleotide were A, the pb primer would become a red 245 nucleotide fragment after the specific enzyme cleavage step. If the fifth nucleotide were T, the pb primer would become a red 244 nucleotide fragment after the specific enzyme cleavage step. If the fifth nucleotide were G, the pb primer would become a red 243 nucleotide fragment after the specific enzyme cleavage step.

If the initial length of the pb primer encoding the first four private nucleotides were 255 nucleotides (encoding private nucleotides 1 to 4 GGGG), the pb primer would be blue. If the fifth nucleotide were A, the pb primer would become a blue 244 nucleotide fragment after the specific enzyme cleavage step. If the fifth nucleotide were T, the pb primer would become a blue 243 nucleotide fragment after the specific enzyme cleavage step. If the fifth nucleotide were G, the pb primer would become a blue 242 nucleotide fragment after the specific enzyme cleavage step.

In this manner, fragments obtained after the specific enzyme cleavage step will not "erase" the initial encoding information about the first four nucleotides, since the color will preserve this information. In other words, even though the pb primers encoding TGGGT and GGGGA will both be 244 nucleotides long after the specific enzyme cleavage step, one can distinguish them from one another on the basis of color since the 244 fragment for TGGGT will be red and the 244 fragment for GGGGA will be blue. Also, no other pentanucleotide private sequences will be encoded with a 244 nucleotide red or blue fragment.

The same type of information can be encoded in molecular weight "blocks" of colors or other tags that are in multiples of four. The molecular weights in Table 2 are particularly useful for this type of analysis, since certain molecular weight ranges or "gaps" are reserved for post-digestion analysis. The general concept is that a small set of independently discernible tags can be used to trace the alteration in size or molecular weight of a large number of DNA fragments cleaved by one or more restriction enzymes. In other words, the specific values shown in Table 2 would contribute to molecular weight of particular tags prior to restriction cleavage, and the gaps between those summed values would allow for nonambiguous identification of molecular weight after such cleavage. The outcome is that private nucleotide sequence information can be encoded in restriction patterns. Such restriction patterns can be planned to yield high density information regarding sequences in the private domains.

Information that is not length encoded can also be placed in the B regions or attached to pb DNA. For example, private nucleotide information can be correlated with labeled pb primers as discussed above, however, the label itself can correspond to new private sequence information. For example, suppose that the identity of a particular private nucleotide is associated with the color of a fluorescent tag associated with a particular pb primer. Four different colors could correspond with the four possible bases at a given private nucleotide position. Thus, the pa primer corresponding to each of the four possible nucleotides at a given private sequence position will be included in a separate vessel with a pb primer that includes a particular color label. Accordingly, only private sequences that have the particular nucleotide being encoded will have pb color label amplified in that vessel.

Excess labeled primer in such a step can be separated out from amplified tag nucleotides if the primer is smaller than any tag that will be measured. Thus, if the size or molecular weight of the nucleotide tags are to be measured to decode particular encoded information, the excess labeled primer will not be detected in the same size or weight range as the tags. For example, if electrophoresis is used to detect the molecular weight of the tags, the excess labeled primers will migrate to the bottom of the gel. Another way to avoid detecting excess labeled primer is to use a limited amount of primer. In other words, there would be no excess primer since it would be completely incorporated into the PCR products used in the PCR reactions.

Such information could be coupled with information encoded by B region lengths to yield additional information resolvable by electrophoresis. For example, five private region positions could be encoded in 1024 different pb region lengths, and a sixth private position could be encoded by the color of a fluorescent dye attached to the pb primer. Thus a single electrophoretic lane could yield information with respect to all hexamers encoded in a population of DNA fragments.

Fluorescent dyes are not the only tags that could be associated with pb primers. Different radionucleotides could be used. Different haptens could be used. Enzyme tags could be used. Examples of multiplex sequencing are discussed in the following documents: U.S. Pat. No. 4,942,124 issued Jul. 17, 1990; "Multiplex Sequencing", Church, G. M. inventor; U.S. Pat. No. 5,149,625 issued Sep. 22, 1992; "Multiplex Analysis of DNA", Church, G. M. and Kieffer-Higgins, S., inventors; and Church, G. M. and S. Kieffer-Higgins "Multiplex DNA Sequencing" (1988) Science 240:185–188. Different radioisotopes also can be used.

While the diversity of each such sets of molecular labels may not be great enough to allow such labels to independently tag a large set of molecules, such molecular labels can be used in conjunction with other labels, such as molecular weight/length tags, to exponentially expand the amount of information that can be encoded.

Another method for decoding information encoded in the pb regions is hybridization using oligonucleotide probes, or probe molecules capable of specifically hybridizing to or identifying B regions. B regions can be constructed so that subregions of contiguous nucleotides comprise sequences that are unique for the particular private fragment with which the particular B region is associated (these B region information-encoding subregions will be called pblE subregions). See, e.g., FIG. 1. As stated elsewhere in this application, the genetic code of the private sequence adjacent to the Region A/private region junction can be translated and encoded with a novel nucleotide language in the A and/or B regions. For example, A's in the private sequence can be translated into AC's in the B region. C's could be translated into CA's, etc. Such a dinucleotide code would keep the A:T/G:C ratio at 1 to 1. Or A's could be translated into GGT, or AACTGA, or any code of choice.

It is simple to create pblEs by PCR if they are separated by "common" sequence subregions, shared by all of the molecules. For example, the molecular population can begin with the same A and B regions attached to all molecules. Sixteen first-stage PCR reactions are carried out, each corresponding to a different private sequence dinucleotide being read. Each corresponding pb1 primer would contain, for example, an octanucleotide (pblE1) representing the particular private dinucleotide being read and amplified in the particular PCR reaction vessel (the private dinucleotide immediately adjoining the A region will be said to occupy private nucleotide positions 1 and 2). Moreover, each pb1 primer would also carry a 5' extension of 20 nucleotides that is identical for all 16 pb1 primers being used in this stage (this will be called a pbcommon1 subregion).

The 16 PCR reaction product pools are subsequently mixed and PCR products are then re-amplified in a second stage of combinatorial PCR using a pa2 primer set and a new set of pb2 primers comprising pbcommon1 sequences at their 3' ends. For an example of suitable pbcommon regions, see FIG. 1. In the second stage of combinatorial PCR, pa2 primers are degenerate or ambivalent at private nucleotide positions 1 and 2, and specific for private nucleotides at positions 3 and 4. Thus, the pooled material from the first PCR reactions is then split into 16 vessels, one for each possible dinucleotide combination at positions 3 and 4. The pa2 primers are used in conjunction with new pb2 primers. Such new pb2 primers comprise 20 common nucleotides at their 3' ends which hybridize with the pbcommon1 region on the stage 1 PCR products (use of 20 nucleotide pbcommon regions and complementary regions on pb primers is exemplary only—other lengths of pbcommon regions and complementary regions on pb primers may also be used). The new pb2 primers also comprise a pblE2 region located 5' to the pbcommon1 region (such pblE2 regions being correlated with the dinucleotides at private positions 3 and 4), and also comprise a new and unique pbcommon2 region. By repeating such a combinatorial PCR procedure through many stages, one creates a B region that comprises multiple pblEs from each PCR reaction stage separated by 20-nucleotide pbcommon regions.

Figure 5:
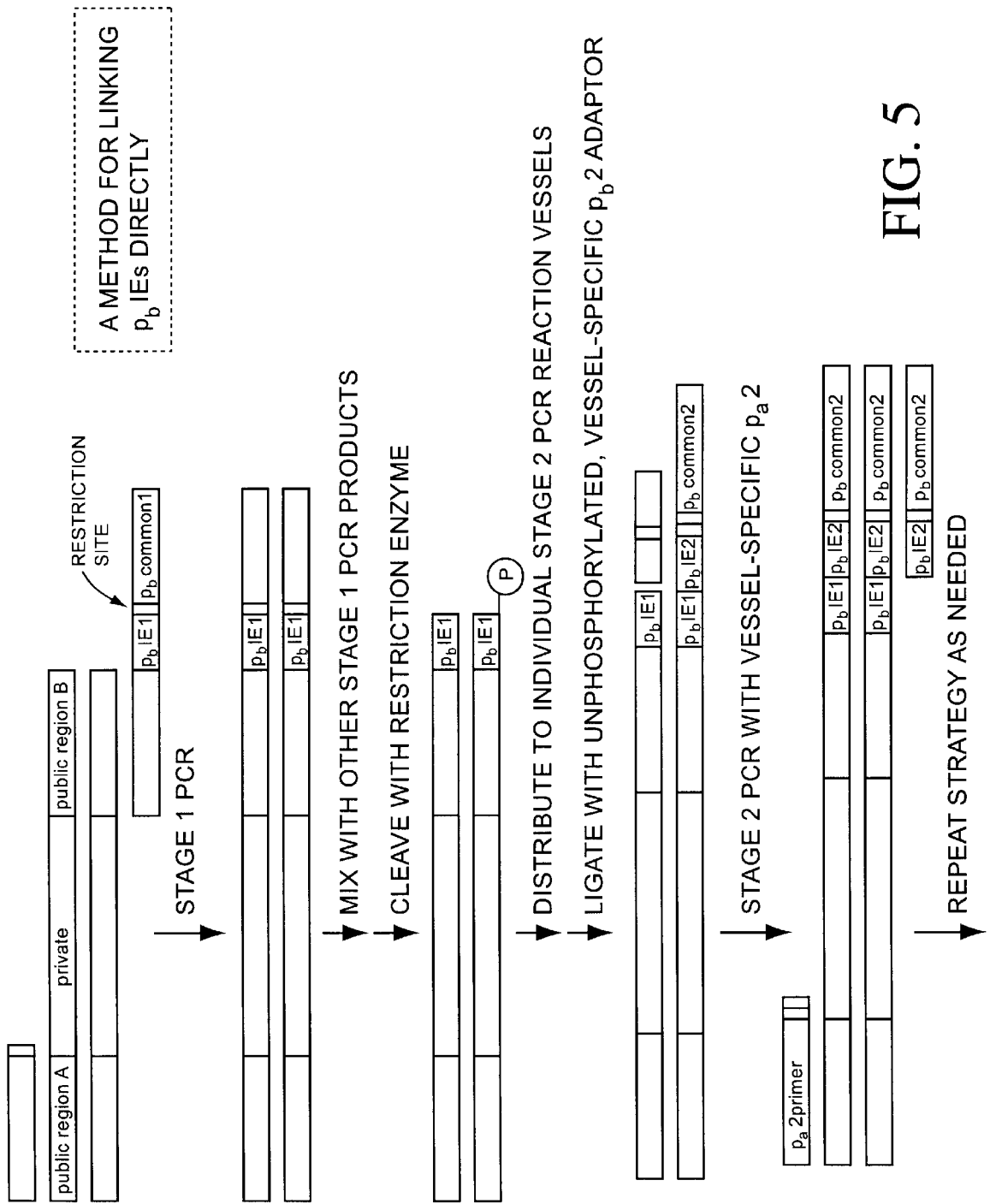
FIG. 5 shows a scheme for ligating tags by cleavage of the pbcommon1 region.

If the pblEs are made as described above, it would not be trivial to decode information contained in the pblEs with hybridization probes in solution phase because the pblEs are separated by 20-nucleotide pbcommon stretches. However, if the pbcommon stretches were eliminated or reduced in size, then contiguous elements of coding information could be examined with hybridization probes. One way of accomplishing this is to encode a restriction site in the pbcommon1 region such that, subsequent to PCR amplification, the molecules are cleaved at the pbcommon1 restriction site. See FIG. 5. (It is possible to inhibit cleavage at other occurrences of such a restriction site—see e.g., Padgett and Sorge, "Creating Seamless Junction Independent of Restriction Sites in PCR Cloning," Gene, 168:31–35 (1996)).

Such a site is situated so that it separates most or all of the pbcommon1 region from the main PCR fragment, yet leaves the pblE1 attached to the main PCR fragment. Cleavage at such a restriction site can leave either a blunt or protruding end on the main PCR fragment. The cleavage can be designed to occur exactly at the pblE1-pbcommon1 junction, or in either pblE1 or pbcommon1. If cleavage occurs in pblE1, some information encoded by pblE1 will be cleaved away. How that information will be recovered in such embodiments will be discussed in more detail below.

Such fragments can then be ligated with a new adaptor comprising a new pblE2 specific for the next stage of amplification. In certain embodiments, the adaptors typically comprise two oligonucleotides which are annealed at regions of complementarity. The following is but one example of how ligation can be accomplished. To create an adaptor, equal molar amounts of the two oligonucleotides are combined, heated, and slowly cooled to a temperature at which the oligonucleotides specifically anneal. Adaptors are ligated to the fragments. The ratio of picomole ends of adaptors to fragments can be varied to increase the ligation efficiency and is typically at least 3:1 (adaptors:fragments). Adaptors and fragments are combined and incubated in 1× ligase buffer (1× ligase buffer is 50 mM tris-HCl [pH 7.5], 7 mM $MgCl_2$, 1 mM dithiothreitol [DTT] and 1 mM rATP) with 2 units of T4 DNA Ligase (Stratagene; La Jolla, Calif.) at a temperature which favors annealing of the adaptor oligonucleotides and enzymatic activity and for a sufficient amount of time for ligation to occur.

The new adaptor also comprises a new pbcommon2 sequence distal to the new pblE2 sequence, for subsequent PCR amplification. If the original cleavage were at the pblE1-pbcommon1 junction, then no pbcommon1 sequences would remain between the first stage pblE1 and the second stage pblE2. The purpose of the pbcommon1 region in such embodiments is to provide a phosphate after the restriction cleavage at the 5' end to allow subsequent ligation. Another way to provide a phosphate at the 5' end is to use a pb1 primer with a phosphorylated 5' end. In such embodiments, one need not include a pbcommon1 region on the pb1 primers.

However, if cleavage occurred in pbcommon1, some pbcommon1 sequences would remain between pblE1 and pblE2 (unless removed prior to ligation). In such embodiments, the portion of pbcommon1 remaining after cleavage, which would be common to all first stage amplification products, may serve as a common site for ligation to the new pblE2 adaptor. In other embodiments, the portion of pbcommon1 remaining after cleavage, which would be common to all first stage amplification products, may serve as a common template for pb2 primers if the second stage involves PCR amplification rather than ligation.

If non-blunt cleavage occurred in pblE1, then some or all of the "overhanging" nucleotides could contain (by design) information with respect to private nucleotides 1 and 2, and new adaptor sets could be constructed to be specific for particular private nucleotide 1 and 2 sets. Thus the stage 2 adaptors could comprise unique pblE2 elements which encode private nucleotides 3 and 4, and also comprise an "overhang" specific for the cleaved pblE1 overhang which is specific for private nucleotides 1 and 2. Such stage 2 adaptors thus not only would encode private nucleotides 3 and 4, but also would be specific for private nucleotides 1 and 2. (Such an embodiment would use 256 different stage 2 adaptors, 16 different combinations of nucleotides at private positions 1 and 2 multiplied by 16 different combinations of nucleotides at private positions 3 and 4.)

Figure 6:
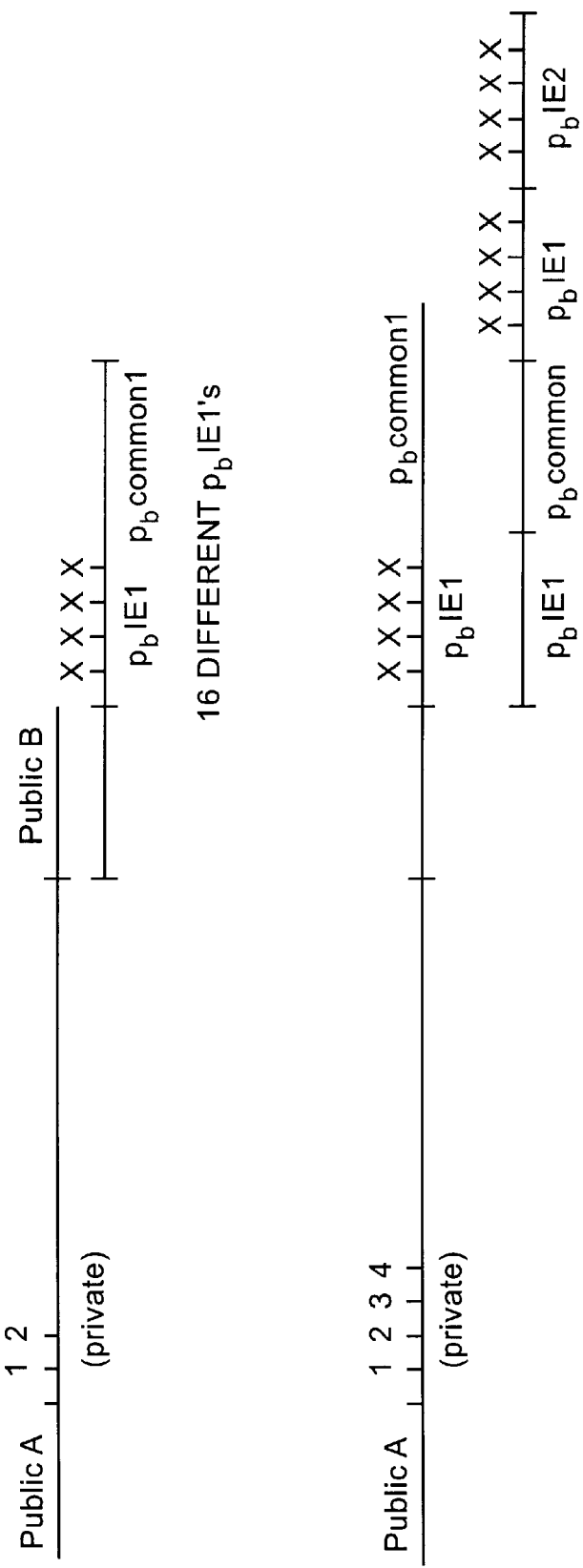
FIG. 6 illustrates embodiments in which previously encoded information is "passed on" in subsequent encoding steps.

While such dual specificity is not necessary for all modes of the invention, certain modes might use such a design to "pass on" information from pblE1 to pblE2, thus giving pblE2 information related to private nucleotides 1 through 4. In such embodiments, since the stage 2 adaptors would be specific for private nucleotides 1 and 2 in view of the specific overlap with pblE1 created after the cleavage, the newly attached pblE2 could encode not only private nucleotide positions 3 and 4 in view of the reading of those positions in stage 2, but would also encode private positions 1 and 2 in view of the specific overlap of the stage 2 adaptor with the previous pblE1. See, e.g., FIG. 6. Such embodiments allow one to create contiguous encoded tag elements without separation by common regions, which may be advantageous for several types of tags. Such a concept could be extended so that each new pblEn contains cumulative information with respect to all private nucleotides decoded through stage n. This concept of passing on information will be discussed in more detail below.

Figure 7:
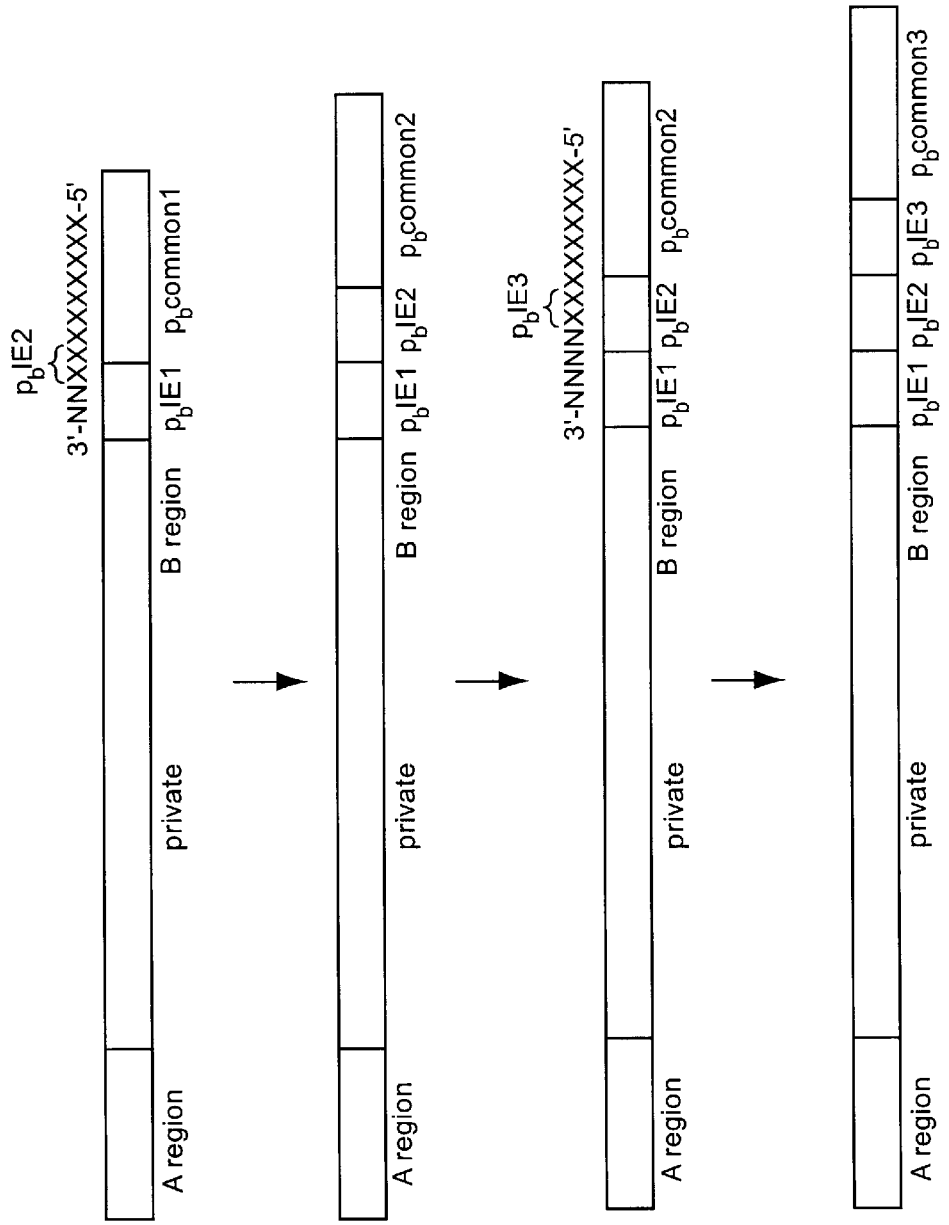
FIG. 7 shows a scheme for linking tags using primer extension.

There are other ways to link pblE elements directly together, without using ligation. One could use chemical coupling instead of enzymatic ligation. Another would be through primer extension. For example, suppose that pblE1 is two nucleotides in length. Then stage two pb2 primers can be designed such that they hybridize to the B region sequence at their 3' ends, are degenerate at the two pblE1 nucleotides, and encode two more specific nucleotides representing pblE2 at their 5' ends. See FIG. 7. This could be repeated with stage three pb3 primers which hybridize to the B region sequence at their 3' ends, but are degenerate at the four nucleotides encoding pblE1 and pblE2, and encode two more specific nucleotides representing pblE3 at their 5' ends.

The risk in this process, however, is that the degenerate pb2 or pb3 primers might not be selective in their hybridization to the pblE regions. For example, if a pb2 degenerate primer were to hybridize such that a mismatch occurred between the primer and the pblE1 region, then a "mutation" would have become incorporated into the pblE1 code. One way to reduce the possibility of such "mutations" would be to design stage 2 pb primers such that they hybridize with only two or three nucleotides immediately adjacent to the pblE1 region in the original B region. Thus, the hybridization of the 3' end of such primers would be dependent on the proper two- or three-base match to the B region, but would also depend on proper hybridization to the pblE1 region. For example, suppose that pb1 primers added a 2 nucleotide pblE1 to the original pb sequence and then added a pbcommon1 sequence to the distal end of the B region. Suppose that pb2 nucleotides 1 to 3, counting from the 3' end, hybridized with the three B region nucleotides immediately adjacent to pblE1. Nucleotides 4 and 5, counting again from the 3' end of primer pb2, would be degenerate in the pblE1 region such that 16 different dinucleotides in each of the primers would match each of the 16 possible pblE1 sequences. Nucleotides 6 and 7 from the 3' end of primer pb2 would encode pblE2. If pblE1 encodes positions 1 and 2 of the private sequence and pblE2 encodes private positions 3 and 4, there would be 16 different primer nucleotides 6 and 7 to encode each of the possible dinucleotide combinations at positions 3 and 4 of the private sequence. In other words, there would be 16 different primers in each of the 16 stage 2 vessels. Thus, there would be 16×16=256 different pb2 primers.

The remaining nucleotides 5' of pblE2 in all of the pb2 primers would be designed to hybridize with the remainder of pbcommon1 and perhaps extend it a few nucleotides in the 5' direction. Thus, such a pb2 primer would hybridize with 3 nucleotides of B, would be completely degenerate in pblE1, would substitute the first two nucleotides of pbcommon1 with a two-nucleotide pblE2 region, and would continue to replicate the remainder of pbcommon1. Thus a 2-base "substitution" would be effected to create pblE2. Subsequent amplification would result in all new fragments having that 2-base substitution. Since the pblE1 sequences would be close to the 3' end of primer pb2, it would be less likely for a mismatch in the pblE1 region to cause efficient primer extension. Such a configuration helps to preserve the "fidelity" of pblEn replication.

Another way to keep pblE regions in a dense cluster is to "pass on" information to each new stage of pb primers. For example, suppose that in stage 1, the pb1 primers hybridize to region B but also comprise about 15 pblE1 nucleotides on their 5' ends. In stage 2, each pb2 primer is synthesized so that it hybridizes with pblE1 at the 3' end of the primer, and then comprises about 15 nucleotides of new sequence at its 5' end that encodes information for both pblE1 and pblE2. Thus, the new pblE2 contains "cumulative" information. Such cumulative information can be "passed on" in each synthetic stage so that the latest pblEn will contain all of the cumulative information contained in the earlier stage pblE's.

Figure 8:
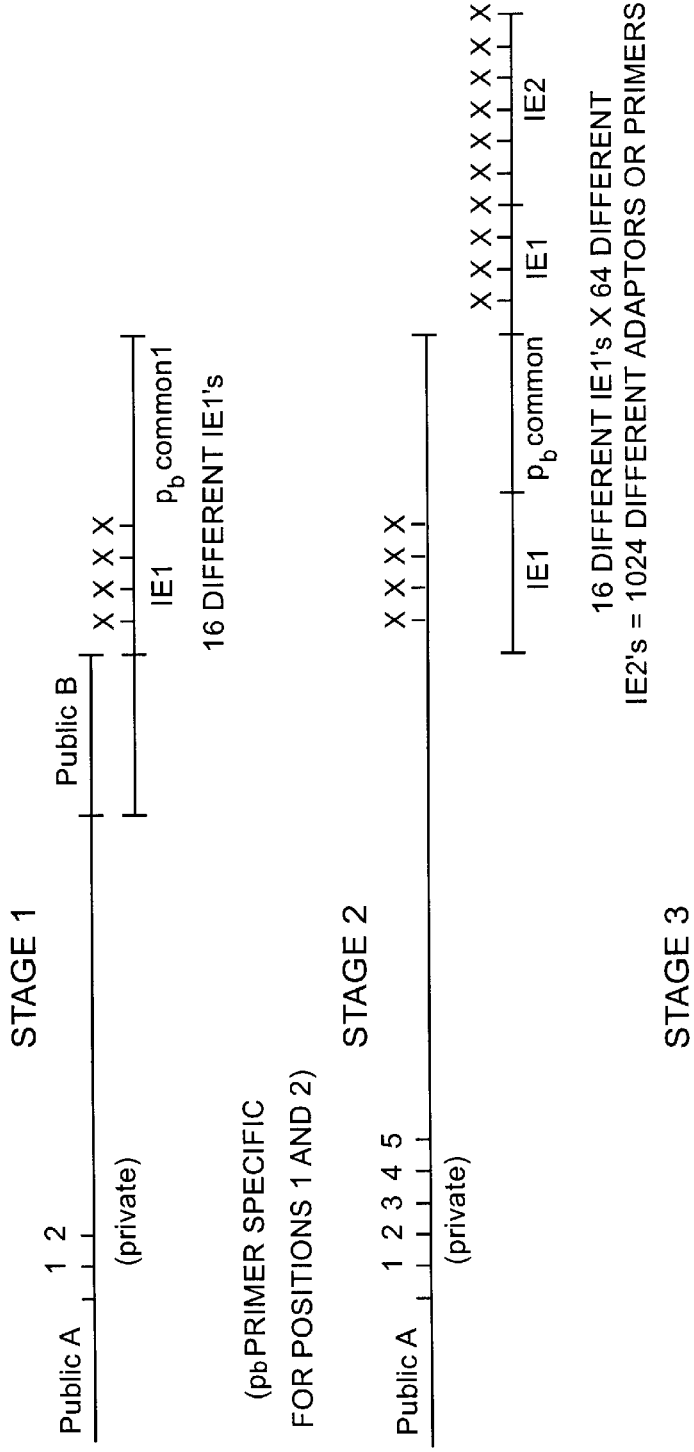
FIG. 8 illustrates additional embodiments in which previously encoded information is "passed on" in subsequent encoding steps.

There may be several advantages when using the "passing on" approach. For instance, one can optimize embodiments in which the tags are unique sequences that are decoded by specific hybridization since common regions do not separate the cumulative information included on the last pblE region. Also, the molecular weight or lengths of tag elements may be reduced if one need not include a common region. This may be particularly advantageous in embodiments in which oligonucleotide tag molecular weight or length encodes private nucleotides, since one need not use a particularly long pb primer or adaptor until the last stage. The earlier stages can encode private nucleotide positions by unique short combinations of bases in the pblE regions (for example 2 base tag elements as shown in FIG. 8). The pb primer or adaptor for the last stage would read specifically the earlier combinations of short combinations of bases in the earlier pblE regions that are all included in the immediately preceding pblE region and convert that information into unique molecular weights or lengths for every possible combination of private nucleotides. See FIG. 8 for example. In such embodiments, the first two stages do not require particularly long adaptors (if ligation is being used to add the tag elements) or primers (if amplification is being used to add the tag elements) since the first two stages involve encoding with short unique sequences, which are later used to convert the specific information encoded by unique sequences into unique molecular weights or lengths. In certain embodiments, the stage 3 reaction in these embodiments may be ligation with 1024 different stage 3 adaptors having 1024 different molecular weights or lengths or amplification with 1024 different pb3 primers having 1024 different molecular weights or lengths. See FIG. 8.

The challenge with this "passing on" approach is that each new generation of pb primers typically must be synthesized such that the primer 3' ends are specific for the cumulative information contained in the prior stage pblE, and such that the primer 5' ends contain information specific for all stages to that point. Thus an exponentially growing number of pb primers typically must be synthesized in each stage. While this might be a lot of work initially, a collection of such primers could then be used for many different combinatorial PCR reactions; thus the large effort becomes spread over many subsequent uses. For example, as discussed below in detail, in certain embodiments, the large collection of primers may be supplied in a kits for end users, and the end users simply run the last stage reaction and then decode the cumulated information.

The advantage to linking pblE regions together with small or no spacer regions between them, whether by a cleavage/ ligation strategy or by a pblEn substitution strategy, is that hybridization probes can be designed that are specific for concatamers of pblE elements. For example, if the pblE regions are represented by 5-mers, and a four stage combinatorial process were carried out with 16 reactions per stage, the pblE string would be 20 nucleotides in length. The 5-mer code could be designed such that the sixteen different 5-mers in the pblE code set were very dissimilar, causing "mismatches" to be very destabilizing to hybridization. Thus an exact match at each pblE element in the string of four pblE elements would be critical for effective hybridization to a complementary nucleic acid molecule. The concept is to essentially increase the binding energy for each bit in the genetic code by substituting a new code, so that hybridization mismatches in the new code are significantly more energy destabilizing than hybridization mismatches in the natural genetic code.

The pblE regions of a collection of such molecules could be hybridized to a collection, panel, or grid of probes specific for the new code. Such hybridization assays would be far more discriminating for "single base" changes in the natural genetic code since they would be represented as multiple "base changes" in the new code. Thus false positive and false negative hybridizations would be far less common with new code hybridizations. This reduces the need for "redundancy" in oligonucleotide panels or grids. References discussing the need for redundancy in oligo panels or grids include: Pease et al., "Light-generated oligonucleotide arrays for rapid DNA sequence analysis" (1994) *Proc. Natl. Acad. Sci. USA* 91:5022–5026; Lipshutz et al., "Using oligonucleotide probe arrays to access genetic diversity" (1995) BioTechniques 19:442–447; and Drmanac et al., "DNA sequence determination by hybridization: a strategy for efficient large-scale sequence" (1993) Science 260:1649–1652. A single oligonucleotide probe would suffice where an overlapping series is currently needed.

It should be clear that linked pblE elements could also be analyzed by mass or size, rather than by hybridization. An advantage to linking pblE regions without intervening pbcommon regions is that the "information density" can be increased. Thus, methods capable of discriminating a small difference in molecular weight could be more effective at decoding information dense subregions than regions separated with information poor (pbcommon) subregions. For example, if mass spectroscopy were used to analyze the strings of pblE elements, it could actually be used to distinguish both the length and molecular composition of the pblE strings. A 20-mer consisting of G's and A's would have a different molecular weight than a 20-mer consisting of T's and C's. Different combinations could create intermediate molecular weight species. While two natural DNA molecules of the same length and same A:T/G:C content will have the same molecular weight, such need not be the case with an expanded genetic code. The expanded code for "A" at position 1 might be AGAGGA, but the code for "A" at position 2 might be CTTCTC. While the natural sequence 5'-AT-3' would have the same molecular weight as 5'-TA-3', this need not be the case with an expanded genetic code.

One could thus use pblE sequences to create a code based upon molecular weight that can be decoded through the use of mass spectroscopy by choosing sequences that had distinguishably different molecular weights. For example, one could encode the 16 different dinucleotides by creating 16 different oligonucleotides that were distinguishable in mass spectroscopy. One example of a set of such oligonucleotide tags is given in Table 3:

TABLE 3

Some possible 20-mers with different molecular weight. N7-deaza A and G are used instead of normal A and G.

|  | Molecular Weight | Difference |
| --- | --- | --- |
| CACTCACTCACTCACTCACT | 5974.0 |  |
| GCCAACCTACCTTCCTACCT | 5990.0 | 16.0 |
| CCGACCGTCCACCCAACCAT | 6007.0 | 17.0 |
| TCTACCTTTCTTTCTATCTA | 6018.0 | 11.0 |
| CACACACTCGCTCGCTCGCT | 6030.0 | 12.0 |
| TCCGACACTTCATTCATCCG | 6044.0 | 14.0 |
| GCCAACCAGCCAGCCTGCCT | 6062.0 | 18.0 |
| GCTTACTTACCAGCCTATTT | 6074.0 | 12.0 |
| CACGCAGACCACTAATCAAT | 6091.0 | 17.0 |
| TGCATTCCTGCGTGCGTTCG | 6107.0 | 16.0 |
| CTACCGATCGACCGAACGAT | 6123.0 | 16.0 |
| CTATCCAGCTAGCAACGTAG | 6138.0 | 15.0 |
| GCTCACTGACTGACAGACTG | 6154.0 | 16.0 |
| CACTCGAGCAAGCCAGCGAG | 6171.0 | 17.0 |
| GACATTGCTGCGTACATGCG | 6185.0 | 14.0 |
| TGCGTGTATCGAGCTACGTA | 6200.0 | 15.0 |

Table 3 illustrates one possible set of 16 different 20-mers having different molecular weights and different sequences. N7-deaza A and G are substituted instead of normal A and G to help with molecular stability for mass spectroscopy (Koster, H., Tang, K., Fu, D., Braun, A., van der Boom, D., Smith, C. L., Cotter, R. J., and Cantor, C. R., "A strategy for rapid and efficient DNA sequencing by mass spectrometry," Nature Biotechnology, 14:1123–1128 (1996)). Note that the largest and smallest molecular weights are different by only 226 Daltons. Thus, if another nucleotide is added to any of these 20-mers, the resulting 21-mer will have a greater molecular weight than any of the original 20-mers. Thus, one can increase the encoded information by adding a nucleotide to the original 20-mers without overlap with any of the original 20-mers. For example, one can add another 16 pieces or elements of information by adding the same nucleotide to each of the original 16 20-mers. In such embodiments, there will be sixteen additional 21-mers with sixteen different molecular weights.

Another use for linked pblE elements without intervening regions would be to create a normal genetic code of desired sequence. For example, pblE triplets could be added in each stage of combinatorial PCR such that the set of possible triplets comprises a desired set of amino acid codons. In this way, the string of pblE elements could comprise a collection of codons potentially encoding a collection of peptides. This would provide a means for creating a library of peptides that encode information, either alone or within a larger protein framework. The peptides could be analyzed to decode the encoded information, for example, by two-dimensional gel electrophoresis or by specific interaction with another molecule, for example, an antibody.

Encoding Information in Same Primer as the "Reading" Primer

Figure 9:
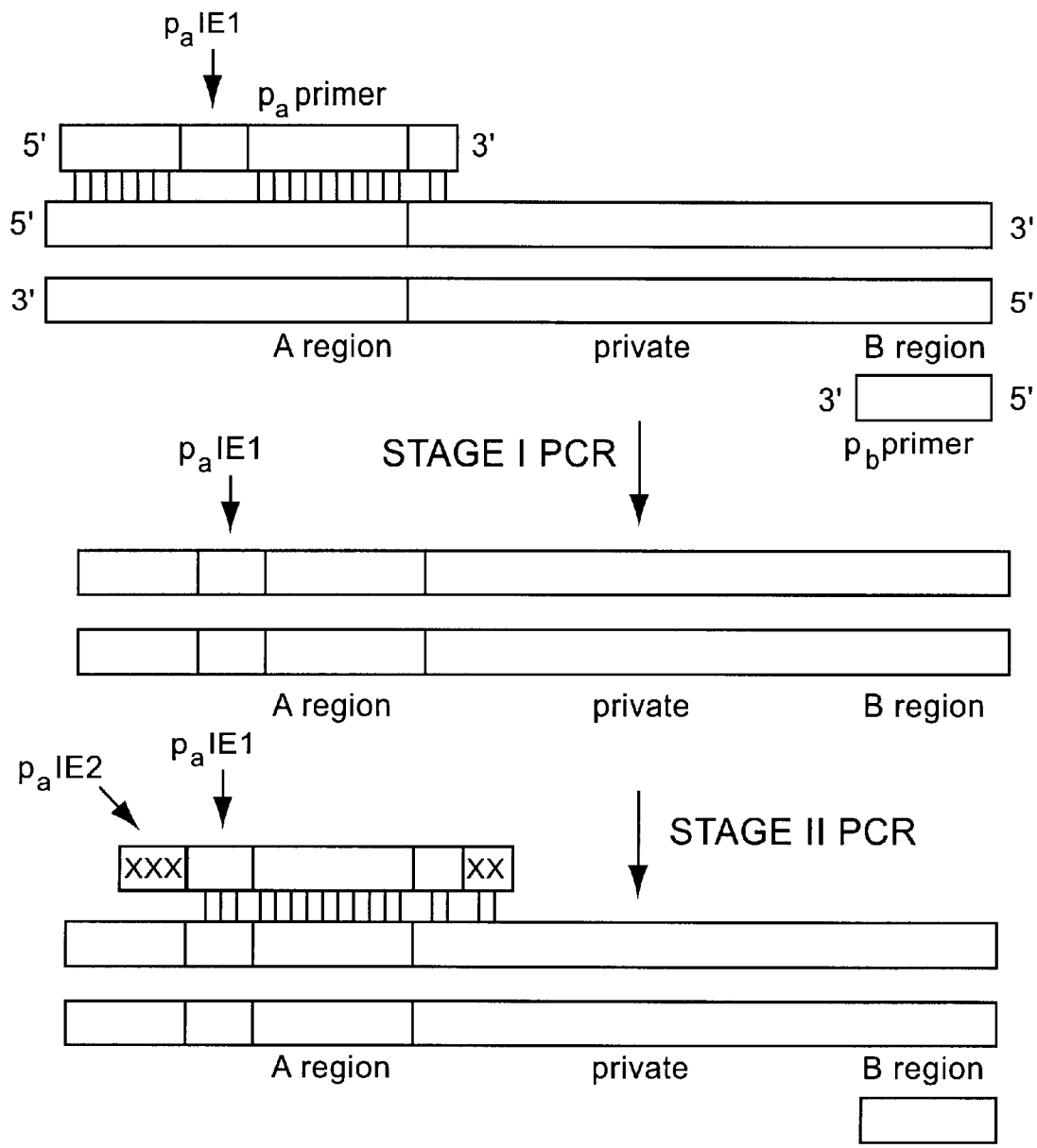
FIG. 9 illustrates embodiments that use the same primer for reading and encoding.

As stated above, according to certain embodiments, it is possible to encode information in the same primer that is being used to determine (read) the sequence of the private nucleotides in the target population. For example, assume one seeks to determine the sequence adjacent to the private—A region junction. See FIG. 9. One can design pa primers that will hybridize to the A region, and will include one or more nucleotides at their 3' end that will hybridize with the private nucleotides adjacent to the A region—private junction. For example, if two private nucleotides are included at the 3' end of the pa primers, then 16 primers would be synthesized to account for all 16 combinations of the private nucleotides. The same pa primers would each include nucleotides near their 5' ends, palE1, that would encode information corresponding to the sequence of the private bases at the 3' end of the primer (see FIG. 9). This palE1 region would not necessarily hybridize with the A region, however there would be sufficient overall base pairing between the pa primer and the A region for efficient hybridization and priming to occur. FIG. 9 illustrates potential base pair positions with vertical lines drawn between the pa primer and the template (although the actual base pairs would form between pa and the lower strand of the template, not the upper strand as shown). Assume that hybridization between the twelve vertical lines at the 3' end of pa (the "XX" region shown and the region 3' of the "XXX") is not sufficient for pa to prime the template under the conditions used. As FIG. 9 shows, however, one can include additional nucleotides on the 5' end of pa that are capable of hybridizing with more of the A region (7 additional base pairs shown in the Figure, although a different number from 7 could be used depending on the chemical compositions of the base sequence). Such additional base pairs would allow for effective binding of pa to the template and effective priming by pa. Each pa primer would contain both the private domain nucleotides for preferential priming (the XX "reading" nucleotides), and the IE element (XXX). Interestingly, when the IE elements are covalently linked to the "reading" nucleotides (XX) on the same primer, the PCR reactions can be carried out in a single vessel instead of 16. The IE element (XXX) may be decoded by hybridization or could pass on information to the next stage IE element as discussed above.

After the Stage I PCR reaction, the templates from Stage I may then be exposed to a Stage II PCR reaction for further specific priming "reading" of the private regions. Assume that private nucleotides 3 and 4 are to be "read" in Stage II. The Stage II pa primer (pa2) is designed such that private nucleotide positions 1 and 2 on the pa2 primer will be degenerate, such that any one of the 16 possible dinucleotides in the template can be accommodated. Private nucleotide positions 3 and 4 will now be occupied by specific bases (XX) for each of the 16 Stage II pa2 primer sets. There will be a pa2lE2 element, toward the 5' end of the pa primer, that will encode the specific information for private nucleotides 3 and 4. The palE1 element of pa2 will now be degenerate for the 16 possible codes created in Stage I (on pa2 primers, each possible combination of private nucleotides 1 and 2 will be represented and will also include each of the 16 corresponding palE1 elements) (it is important to recognize that even though the length of palE1 may be greater than a dinucleotide, there will only be 16 "codons" in the palE1 population).

The palE codes will be created such that mismatches in the palE codes will be very destabilizing. For example, if private nucleotides 1 and 2 are AG, the corresponding palE1 code might be GGA. If private nucleotides 1 and 2 are M, the palE1 code might be TTG. If a pa2 primer carrying the GGA palE1 codon (encoding AG) falsely hybridizes with a template containing both the complement of AA at positions 1 and 2 and the complement of TTG at palE1, there will be an attempted base pairing between GGA in the primer palE1 and MC in the template palE1. This mispairing will be far more destabilizing than the mispairing of AG at positions 1 and 2 in the primer and TT at positions 1 and 2 in the template. Thus the code chosen for the palE elements can be used to decrease the possibility for mispairing of Stage II primers (pa2) on Stage I templates. That is, Stage II primers are designed so that they will not bind to any template except the correct template because there will be too few proper base pairs between a primer:template mismatch. Each palE element can be designed to be longer than 3 nucleotides, allowing for many codon possibilities in the palE "language".

Codon languages that greatly disfavor primer:template mismatches would be most desirable. It is also important to recognize that each Stage 2 pa2 primer will be designed such that the palE1 code will correspond with the nucleotides at private positions 1 and 2 in the primer. The same correlations will exist in the Stage II template population (that is, private nucleotides 1 and 2 in the templates will be physically linked in the same DNA strand with a particular palE1 codon or anticodon). Thus Stage II pa2 primers that encounter a mismatched template at palE1 will also be mismatched with at least one of the template nucleotides at private positions 1 and 2. Even though there may be a perfect match between private nucleotides 3 and 4 and the corresponding sequence in the Stage II pa2 primer, there will not be sufficient base pairing to cause efficient priming to occur, as a result of losing the palE1 and position 1 and/or 2 base pairing.

The same logic can be used for Stage III priming, and beyond. If there is a potential mismatch in Stage III, then either palE1 or palE2 or both will be mismatched along with the corresponding positions 1 and 2 or 3 and 4, or a combination. Codons can be selected so that such mispairing would not allow efficient priming, thus preserving the fidelity of the linkages between palE codes in the amplified template population.

Variations can be envisioned where there are pa common regions, or gaps, between the palE elements if desired. The pb primers also may be "self encoding" to read the private nucleotides adjacent to the B region—private junction. Both ends could be encoded simultaneously, requiring only a single reaction vessel in each Stage of encoding.

In other embodiments, "self encoding" occurs in one or more Stages followed by further encoding in the other primer region as described in other embodiments in this application. Thus, private nucleotides 1 to 6 adjacent to the A region—private junction could be encoded in the pb primer, and private nucleotides 7 to 12 adjacent to the A region—private junction subsequently could be "self encoded" in the pa primer. This could be accomplished by using a pbcommon region specific to the extreme end of the B region during the pa "self encoding" steps. The pbcommon region is the same for all combinations of primers for private nucleotides 7 to 12.

The ability to create codons that will not easily mispair can also be used when designing pb primers such that pblE elements can be placed contiguous to each other without the need for either pbcommon regions or for ligation of adaptors between stages. For example, in FIG. 10 the Stage 1 PCR is performed with a pa primer having a dinucleotide 3' extension to selectively prime templates with specific private nucleotides 1 and 2. The corresponding 16 pb primers have, for example, 12 nucleotides of sequence matching the B region at their 3' ends, have a 5' nucleotide pblE1 element, and have 5 (or more as needed) nucleotides matching the B region at their 5' ends. These reactions would be performed in 16 independent vessels, since the pa "reading" nucleotides are not covalently linked to the pb encoding nucleotides. The pblE1 element does not necessarily hybridize with the B region template. After Stage 1 PCR, the pblE1 elements will be appended to region B. In Stage II PCR, the pb2 primers will each comprise the 16 potential pblE1 codons, and each collection will then contain a specific pblE2 sequence that will be vessel-specific and encode private nucleotides 3 and 4 preferentially primed by the specific pa2 primer in the vessel. If the pb2 primer hybridizes with an incorrect template, such that the pblE1 element is not complementary to the corresponding template sequence, there will not be sufficient base pairing to cause efficient priming by pb2. This can be facilitated by choosing the pblE codons such that each codon will hybridize efficiently with its corresponding anticodon, but very poorly with another one of the 16 (or more) anticodons.

Figure 10:
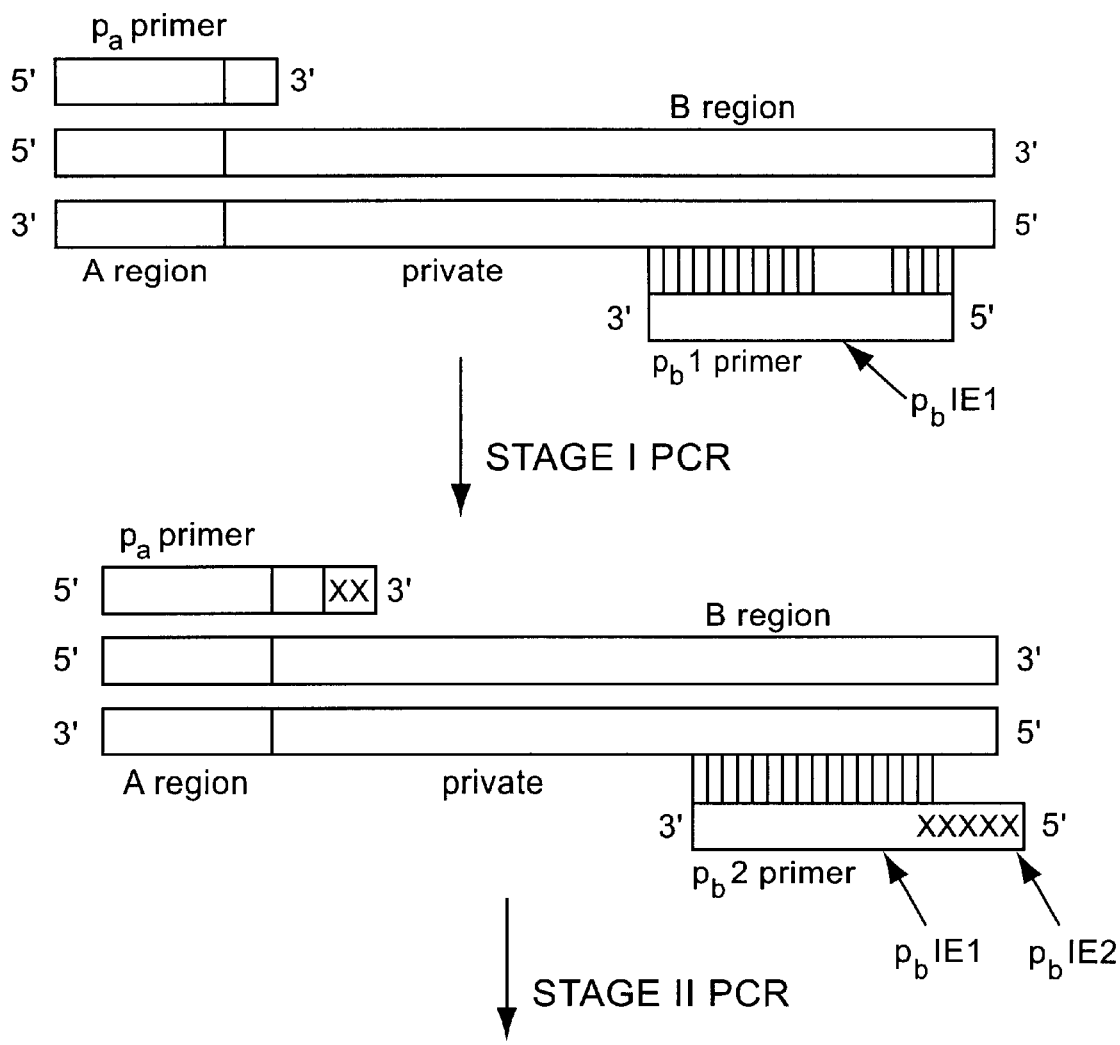
FIG. 10 illustrates certain embodiments of the invention for encoding information.

All of these methods could be applied to primers where 3 or more private nucleotides are being "read" by the primer, using 64 or more primers for such reactions. FIG. 10 simply shows an example of one structure for pa and pb. However, other lengths of hybridizing regions or codon lengths could easily be used.

Use of Nucleotides as Tags For Combinatorial Synthesis Procedures

According to certain embodiments, a library of various nucleic acids can be synthesized by combinatorial synthesis procedures and each of the specific nucleic acids created will be encoded by the length, molecular weight, or some other physical characteristic of nucleotide tags. Such tags, however, may be used for any type of probe molecule synthesized in a combinatorial synthesis method. (In these embodiments, the "probe molecules" are the library of molecules synthesized by the combinatorial techniques that are being tested for potential uses.) For example, the probe molecules may be peptides and some feature of the nucleotide tags, such as molecular weight, length, melting temperature, denaturing condition, or annealing property will identify the particular amino acid sequences of those peptides. The molecules may be various types of organic chemicals that are synthesized by various pathways. The nucleotide tags will provide the order of synthesis and, thus, the identity of each of the organic molecules made in the library. In preferred embodiments, these tags will permit simultaneous decoding of the tags without separation of the tags from one another prior to the commencement of the decoding steps.

To use nucleotide tags with combinatorial synthesis of materials other than nucleic acids, one should keep in mind the compatibility of the reaction conditions for synthesis of the other materials with conditions suitable for the nucleotide tags. Such considerations are discussed in detail in PCT Publication No. WO 93/06121, which is hereby specifically incorporated by reference into the present application. See WO 93/06121, e.g, at page 17, line 14, through page 19, line 5; at page 24, line 5 to line 18; at page 37, line 32, through page 39, line 3; at page 40, line 23, through page 45, line 21; and at page 46, line 28, through page 48, line 21.

According to certain preferred embodiments, nucleic acids are synthesized using the combinatorial "pool and split" method. (This procedure could also be used for combinatorial synthesis of other materials such as peptides or organic molecules.) For a simple DNA molecule containing the four normal bases, the first stage or step in the synthesis is carried out with four reaction vessels. Each reaction vessel contains one of the four DNA bases. This will be called the first synthetic "stage". Each base is physically linked to a unique tag molecule, specific for that reaction vessel. Such linkage can be either direct, via a linker molecule, or via a solid support.

One skilled in the art will be able to design appropriate conditions for the combinatorial synthesis, including the attachment of tags. General methods of using other types of tags can be gleaned from PCT Publication No. WO 93/06121, e.g., at page 15, line 27, through page 19, line 5; at page 22, line 11, through page 24, line 3; at page 36, line 15, through page 39, line 21; and at page 40, line 23, through page 49; and from PCT Publication No. WO 96/12014, e.g., at page 12, line 1, through page 14; and at page 15, line 33, through page 17.

Figure 11:
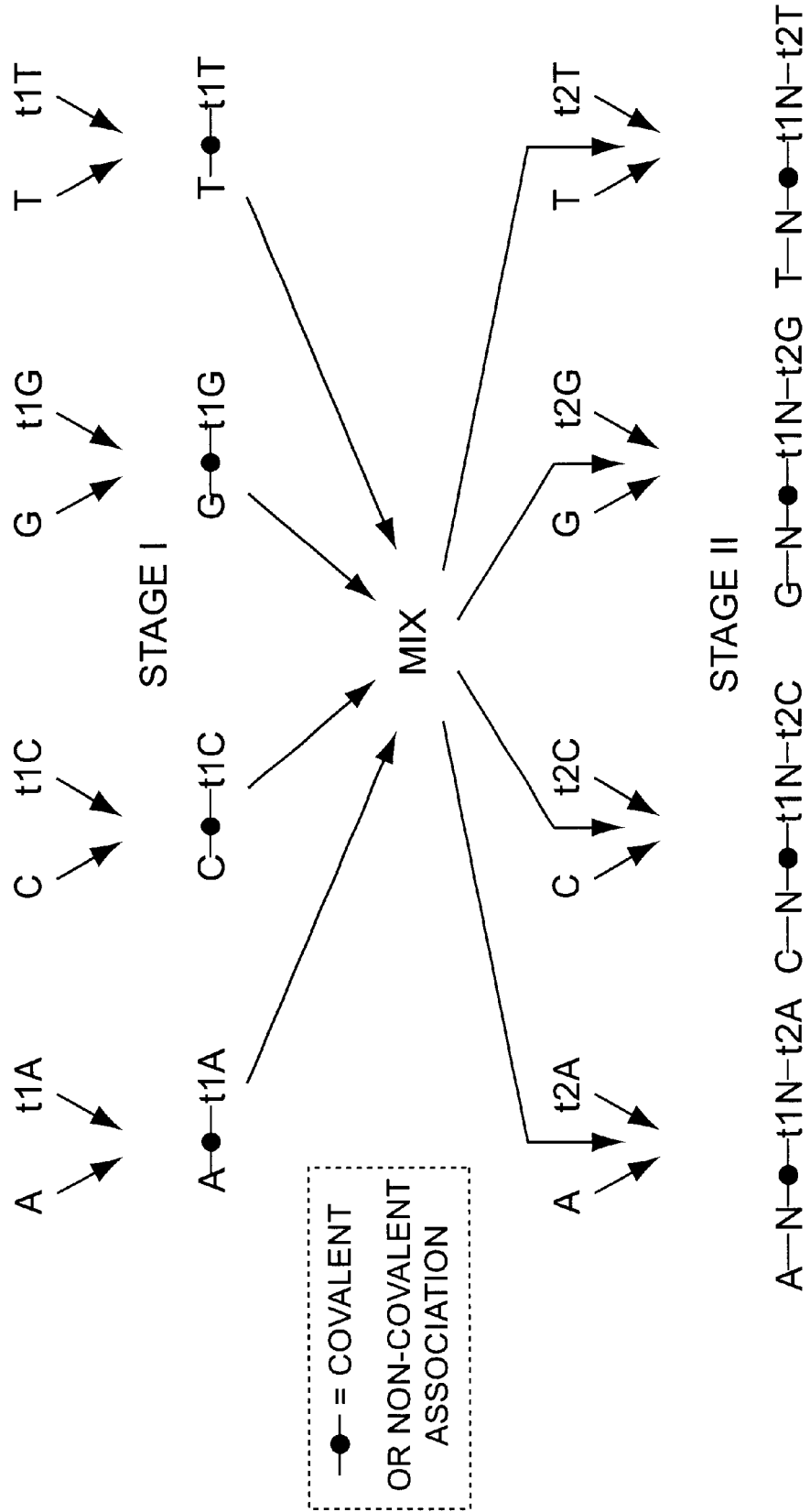
FIG. 11 shows a scheme for encoding information about combinatorial synthesized libraries using nucleotide tags.

For example, in the reaction vessel into which adenosine is added, the adenosine is physically associated with a tag that will be referred to as t1A. In the reaction vessel into which cytosine is added, the cytosine will be physically associated with a tag referred to as t1C. The same nomenclature is used for G and T. See FIG. 11 for this Stage 1 of the synthesis and subsequent steps discussed below.

After the coupling reactions have been completed, the contents of all four reaction vessels are pooled and mixed. The mixture is then divided into four new reaction vessels, which will be called "Stage 2". For each vessel in Stage 2, a second nucleotide is attached to the nucleotide in the first nucleotide position of the growing nucleic acid molecule. For any given molecule, the first position of the growing oligonucleotide can be any one of the four nucleotides (due to the prior pooling and mixing), but the second nucleotide position will be unique for the particular second stage reaction vessel. In each reaction vessel in Stage 2, a second set of unique tag molecules is associated with the growing tag chain. For example, in the second stage A reaction, the tag t2A is added. In the second stage G reaction, the tag t2G is added.

The growing tag chain preserves the identity of (encodes) the growing nucleic acid sequence being made in the combinatorial library, so that one can later decode the tags to identify every nucleic acid sequence made by the combinatorial synthesis scheme. The tags are physically linked to each other as they are added in each stage. If the tags are designed such that the sum of the molecular weights of any "chain" of tags is a unique molecular weight, then the molecular weight of the tag chain can be used to identify the particular chemical compound (oligonucleotide) associated with the tag. For example, to synthesize 256 oligonucleotides each 4 bases in length, 16 tag molecules would be needed. If the molecular weights of the tag molecules are multiples of the numbers shown in Table 1 discussed above in this specification, the sums of the molecular weights of any four tags, one selected from each row, would be independently, and simultaneously identifiable. One could also design tags based on Table 2 discussed above or any other system in which the particular probe element added in the combinatorial synthesis scheme and its position in the compound being generated is encoded by a tag element having unique molecular weight, length, or other uniquely identifiable property such as melting temperature, denaturing condition, or annealing property.

Such molecular weights can be analyzed simultaneously using various methods. For example, mass spectroscopy could be used to analyze the collection of unique molecular weights (Fitzgerald, M. C. and Siuzdak, G. "Biochemical mass spectrometry: worth the weight?" *Chemistry and Biology* 3:707–715, 1996; Also see the following articles: Tang et al.,"Matrix-assisted laser desorption/ionization mass spectrometry of immobilized duplex DNA probes" (1995) *Nucleic Acids Res.* 23:3126–3131; U.S. Pat. No. 5,547,835 "DNA sequencing by mass spectrometry", H. Koster, inventor; and U.S. Pat. No. 5,605,798 "DNA diagnostic based on mass spectrometry", H Koster, inventor). The molecular weight species seen in the mass spectrograph would uniquely identify the linkages of the tags and thus would identify the pathways that each molecule traveled during the chemical synthesis reactions. If 256 oligonucleotides are synthesized using four reaction vessels in each of four stages, and a set of four tags are coupled to each oligonucleotide, then each member of a particular subset of the 256 oligonucleotides can be identified by analyzing the molecular weight of the tags associated with the subset of oligonucleotides.

The tags could first be physically cleaved away from the oligonucleotides made in the combinatorial synthesis before molecular weight analysis. This could be accomplished by laser desorption using mass spectrometry as discussed in Tang et al.,"Matrix-assisted laser desorption/ionization mass spectrometry of immobilized duplex DNA probes" (1995) *Nucleic Acids Res.* 23:3126–3131; U.S. Pat. No. 5,547,835 "DNA sequencing by mass spectrometry", H. Koster, inventor; and U.S. Pat. No. 5,605,798 "DNA diagnostic based on mass spectrometry", H Koster, inventor).

According to certain embodiments, nucleotide tags are amplified prior to the decoding steps. (Such embodiments may include those in which amplification was not used to create oligonucleotide probe libraries.) Such amplification of different nucleic acid tags is discussed, e.g., in PCT Publication Nos. WO 96/12014 and WO 93/06121. See, PCT NO. WO 93/06121, e.g., at page 28, line 28, through page 29, line 6; at page 39, line 5 through line 21; at page 41, line 27, through page 42, line 7; at page 46, line 5 through line 26; and at page 49, line 5 through line 18.

If the oligonucleotides were longer than four bases; 256 unique tag sequences would only encode information for some of the positions in such an oligonucleotide set. For example, information regarding the terminal four nucleotide positions could be encoded by the 256 unique tags, with the rest of the oligonucleotide residues being anonymous (with respect to the information in the tags).

More than four stages of synthesis could be performed. If unique tag identifiers are desired for 7 nucleotides of information, then 28 tag molecules could be used (although as seen above, the tags need not be unique in molecular weight—only the molecular weight sums need be unique). In addition, the linkages of such molecules would be discernible if there were $4^7$ (16,384) different separately identifiable signals created by the combinations. This presents a challenge if molecular weight is to be used to identify the 16,384 different combinations. Electrophoresis and chromatography (HPLC) are alternative methods for rapidly determining a large number of molecular weights simultaneously. More than one method could be used in series. For example, the tags could first be separated into subgroups by electrophoresis. Each subgroup could then be analyzed by a second dimension of electrophoresis or by mass spectroscopy.

To reduce the amount of decoding needed, one can screen members of the produced combinatorial probe library for a given desired activity prior to decoding. Decoding would not be needed for members that lack sufficient activity. In other words, one enriches the probe library to be decoded by eliminating members of the library that lack sufficient desired activity.

These embodiments of the invention permit rapid, simultaneous decoding of the synthetic pathways of a relatively large subset of molecules in a combinatorial library, without the need to physically separate the individual tags prior to decoding.

Primer Extension Reactions

In certain embodiments of the invention, primer extension reactions are used. Any method of primer extension can be used and may include the use of thermostable and thermolabile polymerases. The only requirements are that the conditions under which the annealed primer and template are extended be discriminatory, i.e., that they exceed a threshold of binding energy between the primer and template in order for extension to occur. Such conditions are discussed in this application, for example, in Example 6.

Suitable thermolabile polymerases from mesophiles are available from many commercial sources and include, modified T7 DNA polymerase, Exo⁻ Klenow and the like. Suitable thermostable polymerases from thermophiles and hyperthermophiles are also available from commercial sources and include polymerases isolated from *Thermus aquaticus* (Taq DNA polymerase; Stratagene; La Jolla, Calif.), *Thermus thermophilus* HB-8 (Tth; Perkin Elmer; Alameda, Calif.), *Bacillus stearothermophilus*, and the like.

The polymerases may have activities other than polymerase activity such as 5'→3' exonuclease, 3'→5' exonuclease, endonuclease and 3' extendase activities. For a review of thermostable DNA polymerases and their activities see "Thermostable DNA Polymerases" in Methods of Enzymology, Vol. 48: 377–435, 1996, Academic Press, Inc. incorporated by reference. Polymerases having 5'→3' exonuclease and lacking 3'→5' exonuclease nuclease activity may be used in this invention. Polymerases having 3' extendase activity sometimes add an additional nucleotide, most often an A, at the 3' end of the PCR product. Such polymerases, for example, Taq DNA polymerase, may not be optimal in the examples described herein where tags are identified by molecular weight. Examples of suitable polymerases lacking 3'→5' exonuclease activity are Exo⁻ Pfu DNA polymerase (Stratagene; La Jolla, Calif.), Exo⁻ Klenow (Stratagene; La Jolla, Calif.) and *Thermotoga maritima* (UlTima; Perkin Elmer; Alameda, Calif.). Polymerases having 3'→5' exonuclease activity may be used under conditions which reduce or eliminate this activity. Polymerase conditions such as salt, pH and, in particular, temperature are known to affect polymerase activity. Also contemplated is the use of recombinant polymerases in which one or more mutations have been introduced into the nucleotide sequence resulting in the reduction or absence of 3'→5' exonuclease activity. The polymerases may be purified from the native organism or be expressed and purified from a recombinant source.

The use of additives which may enhance a desired result such as a change in priming specificity of the primer and template or a change in the polymerase activity and/or processivity of one or more polymerases in a primer extension reaction and the like are also contemplated. Exemplary suitable additives in primer extension reactions are Perfect Match® DNA polymerase enhancer (U.S. Pat. No. 5,449,603; Stratagene; La Jolla, Calif.), Polymerase Enhancing Factor (U.S. patent application Ser. No. 08/822,774, filed March 21, 1997, "Polymerase Enhancing Factor 'PEF' Extracts, PEF Proteins and Methods for Purifying and Identifying Same"), mutS (Wagner, R., et al., *Nucleic Acids Res.* 23:3944–3948, 1995 and Takamatsu, S., et al., Nucleic Acids Res. 24:640–647, 1996; Epicenter, Technologies, Madison, Wis.), betaine (Baskaran, N., et al., Genome Methods 6:633–638, 1996; U.S. Pat. No. 5,545,539; Sigman, St. Louis, Mo.), dimethyl sulfoxide (DMSO; Hung, T., et al., *Nucleic Acids Res.,* 18:4953, 1990; Sigma, St. Louis, Mo.), formamide (Sarkar, G., et al., *Nucleic Acids Res.* 18:7464, 1990; Stratagene, La Jolla, Calif.), tetramethylammonium chloride (TMAC; Chevet, E., et al., *Nucleic Acids Res.* 23:3343–3334, 1995; Sigma, St. Louis, Mo.), T-7 type single stranded DNA binding protein (U.S. Pat. No. 5,534,407), gene 32 protein of phage T4 (Schwarz, K., et al., *Nucleic Acids Res.,* 18:1079, 1990) and the like.

EXAMPLE 1

Combining Different Types of Tags and Decoding Methods to Create a Large Amount of Information About Target Molecules that can be Decoded In a Simultaneous Manner One way to combine a pblEn length code with a pblE sequence (mass) code would be to carry out a first stage of combinatorial PCR with, for example, 16 reaction vessels, each of which encodes the different possible combinations of private nucleotides 1 to 2. The 16 pb1 primers would each comprise 20 new nucleotides of unique sequence at their 5' ends, with a restriction site dividing the original B region sequences from the 20 new nucleotides, thus adding 20 unique nucleotides to the distal B regions of each fragment. The 20 unique nucleotides would comprise the pblE1 information. The 16 different 20-mer sequences would be chosen such that they had distinguishably different molecular weights (Li, Y., Tang, K., Little, D. P., Koster, H., Hunter; R. L., and McIver, R. T. "High-resolution MALDI Fourier transform mass spectrometry of oligonucleotides," Anal. Chem., 68: 2090–2096 (1996)) and sufficiently different sequences such that 16 different pb2 primers could be designed to specifically amplify each of the stage 1 PCR fragments by priming in the 20-mer region. See Table 3 above.

Stage 2 would have 64 reaction vessels, each with a different pa2 and pb2 primer set. The pa2 primers would be degenerate for private nucleotides 1 and 2, and would be specific for private nucleotides 3 to 5.

Stage 2 reaction vessel 1 would have 16 different pb2 primers (specific for the 16 different pblE1 sequences) each 20 nucleotides in length. Thus, reaction vessel 1 would not change the molecular weights of the tag elements from the first stage reaction. The original sixteen different molecular weights, however, not only would encode the sixteen different possible combinations at private positions 1 and 2, but also would encode the first possible combination of private positions 3, 4, and 5.

Reaction vessel 2 would have 16 different pb2 primers 21 nucleotides in length, of which the first 20 nucleotides on the 3' end would be specific for the 16 different pb1 E1 sequences. Typically, the newly added nucleotide will be the same for each of the 16 different pb2 primers in vessel 2. The newly added nucleotide will shift the original molecular weight of each of the original 20-mers by the weight of the newly added nucleotide. The new molecular weight not only would encode the sixteen different possible combinations at private positions 1 and 2, but also would encode the second possible combination of private positions 3, 4, and 5. This would continue up to reaction vessel 64, which would have 16 different pb2 primers 83 nucleotides in length (the longer lengths could be created in 2-step PCR reactions or nested PCR reactions as discussed in more detail below).

If the amplified molecules were cleaved at a restriction site separating the original B region sequence from the 20-mer sequence, molecules would be liberated ranging in size from 20 to 83 nucleotides. Such molecules would have 1024 (64×16) different molecular weights, each of which would encode only one possible combination for a five nucleotide sequence. Such molecules could be analyzed by mass spectroscopy.

EXAMPLE 2

A Method for Determining the Sequence of DNA Using DNA Amplification Techniques and Uniquely Identifiable Tags In certain embodiments of the invention, the sequence of a fragment of DNA can be determined by using uniquely identifiable tags in combination with DNA amplification techniques without having to resort to traditional DNA sequencing techniques or to attaching to a solid phase (such as a bead or a two-dimensional solid support) either the materials to be analyzed or the uniquely identifiable tags.

In these embodiments, the uniquely identifiable tags are nucleotides. These nucleotides can be sequences having specified lengths or molecular weights. They can also have specified melting temperatures, binding energies, or isoelectric points. These nucleotides can also have specific compositions or sequences specifically recognized by complementary sequences. In the latter case, the nucleotides could form primers for use in DNA amplification techniques. These nucleotides could be associated with other types of specified materials such as fluorescent atoms or molecules, radionucleotides, atoms conducive to NMR measurement, materials recognized by a protein (such as haptens or enzyme substrates, for example), or materials recognized by other affinity reagents.

Nuclear magnetic resonance (NMR) can also be used to encode tag information. For example if tag molecules contained fluorine atoms, the fluorine NMR spectrum would yield information not only regarding which tag molecules were contained in a particular set of linked tags, but also regarding the sequence of such tags. Such NMR spectral information would be unique for each sequence of tag linkages and would be identifiable even in the presence of other tag sets. NMR is discussed in Rastinejad et al.,"Studies of nucleic acids and their protein interactions by $^{19}$F NMR" (1995) Meth. Enzymol. 261:560–575.

It is possible to use these various different specific identification materials and techniques in combination to exponentially expand the amount of information that can be encoded by the uniquely identifiable tags than the amount that could be obtained through the use of a single class of materials or techniques alone. As a result, it is intended that any specifically identifiable nucleotide tag, directly or indirectly, alone or in combination with one or more other materials, could be used in this invention.

In this example, a target DNA gene or other fragment to be studied is prepared and then sheared into a collection of DNA sequences having an average size that permits reasonably efficient DNA amplification. Such a size can be about 200 base pairs in length, but any size can be used as long as the DNA can be amplified reasonably efficiently.

Prior to shearing, the target DNA may be flanked by some additional known DNA sequence, which may be called "flanking DNA." The amount should be sufficient to determine the nucleotides at the ends of the private sequence. The purpose of this step is to create fragments having a large number of random starting points throughout the length of the target DNA such that sequencing terminal nucleotides of each sheared DNA fragment will produce an overlapping sequence of the entire target DNA.

One skilled in the art will know how to accomplish this shearing. Exemplary methods include the use of nebulizers as described in Anderson et al., "A 'double adaptor' method for improved shotgun library construction" (1996) Anal. Biochem. 236:107–113.

The DNA is treated so that its ends are blunt. Treatment to make blunt ends can include stranded exonuclease and/or with a DNA polymerase and dNTPS. Then adaptor region A is attached to one end of each fragment to be sequenced and adaptor region B is attached to the other end. One skilled in the art will know various methods for attaching adaptor regions. For example, the adaptor regions can be attached by ligation to the ends of the fragments or by insertion of the fragments into cloning vectors where the adaptor regions flank the cloning site. Ligation can be performed according to methods known to those skilled in the art. Exemplary methods are described in the following references: Wieland et al., "A method for difference cloning: Gene amplification following subtractive hybridization" (1990) Proc. Natl. Acad. Sci. 87:2720–2724; Lisitsyn et al., "Cloning the differences between two complex genomes" (1993) Science 259:946–951; Lisitsyn et al., "Representational difference analysis in detection of genetic lesions in cancer" (1995) Meth. Enzymol. 254:291–305; U.S. Pat. No. 5,436,142 "Methods for producing probes capable of distinguishing variant genomic sequences", Wigler, M. and N. Lisitsyn, inventors; and U.S. Pat. No. 5,501,964 "Methods for producing probes capable of distinguishing DNA from related sources", Wigler, M. and N. Lisitsyn, inventors.

In certain embodiments, the adaptor regions A and B are each preferably 20–40 nucleotides long. Adaptor region B preferably has a unique restriction site at the junction between it and the DNA fragment to be sequenced. Primers pa and pb are designed such that they can anneal to adaptor regions A and B, respectively, and permit the amplification of the DNA fragments to be sequenced. As discussed above, the DNA sequence between the two adaptor regions, whose sequence is sought, is the "private" sequence.

Combinatorial DNA amplification techniques having multiple stages are then performed. A variety of strategies can be used. For example, PCR is a preferred strategy, but it is not a required strategy. As another example, strategies can vary in terms of the number of vessels employed at one or more stages. A 64 vessel strategy is convenient, but fewer or greater numbers of vessels can be employed.

In general, these strategies each involve at least two types of phases-an encoding phase and a decoding phase. A preferred type of encoding phase involves combinatorial DNA amplification strategy in which the samples are alternatively split and pooled in each stage for one or more stages. At each stage, one or more different tags are attached to the DNA fragment or fragments to be sequenced whereby the sequence of the DNA fragment or fragments is encoded. Following the addition of the tags in one or more stages, the tags are analyzed in the decoding phase in order to decode the encoded sequence information. An increase in the number of stages and/or the number of different tags added in the encoding phase to the DNA fragment to be sequenced can result in an increase in the amount of sequence information that can be obtained during the decoding phase.

An example of a combinatorial DNA amplification strategy is given in order to illustrate one possible use of this invention to sequence DNA, and this example does not limit the scope of the invention. PCR is used as the DNA amplification technique, together with a 64-vessel, pool-and-split strategy.

In the first stage, 64 different primers are designed that each will anneal to adaptor region A flanked by a specific three-nucleotide private region. These primers are referred to as "pa1." (Primers will be referred to by the adaptor region with which they are designed to anneal to, together with the planned annealing stage number. Thus, "pb2" refers to the primers that are designed to anneal to adaptor region B during stage 2.) The 64 different pa1 primers are designed such that the final three nucleotide bases at the 3' end of each pa1 primer are complementary to the first three bases of the private regions that abut region A. All 64 combinations of three nucleotides are to be represented among the 64 different primers (AAA, MC, MG, MT, ACA, ACC, ACG, ACG . . . TM, TAC, . . . etc.).

Each different pa1 primer is placed in a separate PCR reaction vessel with a pb1 primer that corresponds to that particular pa1 primer. Each pb1 primer will hybridize with region B and will encode information with respect to the sequence of private nucleotides 1 to 3 that are read by the particular pa1 primer. Thus, 64 different pb1 primers are designed that will anneal to adaptor region B during stage 1. In this example, the extra nucleotides at the 5' end of pb1 that do not hybridize with adaptor region B encode information about the sequences of the private nucleotides 1 to 3. The total number of nucleotides in the pb1 primers correlate to the sequence of private nucleotides 1 to 3 as follows:

TABLE 4

|  | A | C | G | T |
|---|---|---|---|---|
| Private Nucleotide 1 | 1 | 2 | 3 | 4 |
| Private Nucleotide 2 | 4 | 8 | 12 | 16 |
| Private Nucleotide 3 | 16 | 32 | 48 | 64 |

This table is designed such that each trinucleotide sequence will correspond to a different sum. Thus, if pa1 is designed to anneal to the private sequence AGC, then the corresponding pb1 would have a total of 1+12+32=45 nucleotides that correspond to AGC. On the other hand, if pa1 is designed to anneal to the private sequence GCA, then the corresponding pb1 would have a total of 3+8+16=27 nucleotides that correspond to GCA. If adaptor region B was 20 nucleotides in length, then the pb1 that corresponded to the pa1 that is designed to anneal to the private sequence AGC would have 45–20 (the number of nucleotides complementary to region B, which all pb1 primers include)=25 extra nucleotides at its 5' end. For the pb1 primer corresponding to the pa1 designed to anneal to GCA, there would be only 7 extra nucleotides.

It is within the level of skill of the art to design other tables that would ensure that each private three nucleotide sequence would be associated with a different sum. It is also within the level of skill in the art to design tables that result in unique sums for longer private nucleotide sequences. Thus, a 256-vessel strategy having pa1 primers designed to anneal to the first four private sequence nucleotides could be pursued. In such a case, a fourth row would be added to Table 4. The fourth row would encode the number of nucleotides corresponding to each possible nucleotide at the fourth position. For example, a fourth row could be added to Table 4 assigning the following values to each fourth private nucleotide:

TABLE 5

|  | A | C | G | T |
|---|---|---|---|---|
| Private Nucleotide 4 | 64 | 128 | 192 | 256. |

All of the pb1 primers in this example also have a common specific sequence at the 5' end, which is referred to as "pbcommon1." This common region will permit subsequent amplification of the extra nucleotides at the 5' end of the region complementary to region B, since the pb2 primers (for the second amplification step) will all include a region complementary to pbcommon1. To incorporate pbcommon1, all of the pb1 primers can include a common 20 nucleotide region complementary to the B region at the 3' end and a common 20 nucleotide pbcommon1 region at its 5' end. There are at least two ways the extra encoding nucleotides of Table 4 could be included in pb1. The first simply adds them between the region B complementary region and pbcommon1. In such an embodiment, one would simply add the constant 40 (20 region B completing region+ 20 pbcommon1) to the sum for private nucleotides 1 to 3 of Table 4.

A second embodiment does not require adding the constant 40 to the unique number of Table 4, since nucleotides of the B complementary sequence and pbcommon1 are included in the nucleotides calculated in Table 4. The shortest encoding sequence in Table 4 is for private sequence AAA, which is 21 nucleotides in length. The sequence complementary to the B region accounts for twenty of those nucleotides. The twenty-first nucleotide would be the particular nucleotide at the 3' end of pbcommon1. Thus, the pb1 that corresponds to pa1 for AAA would be 40 nucleotides in length (20 for complementary B region sequence and 20 for pbcommon1). The next shortest pb1 would correspond to the pa1 for CAA, which requires 2+4+16=22 nucleotides from Table 4. This pb1 primer would have the same sequence as the pb1 primer for AAA except it would include an additional nucleotide between the region B complementary sequence and pbcommon1. It would thus include 41 nucleotides. Thus, it should be apparent that the total number of nucleotides for each pb1 will be the particular sum for the private nucleotides from Table 4 added to the constant 19.

Each of the 64 corresponding pairs of pa1 and pb1 primers are added to only one of the 64 reaction vessels such that the two different primers are unique for each vessel. The randomly sheared adaptor-ligated NDA and PCR reagents are added to each vessel, and the PCR reactions are then run to completion. The reaction conditions are set so that there will be no exponential amplification of a given fragment unless the pa1 primer is correctly matched to it. In other words, to be amplified, a fragment must have the first three nucleotides of the private region next to the A region that are complementary to the three 3' nucleotides of the pa1 primer in a given reaction vessel. How one may optimize conditions to achieve this goal is discussed above and below in Example 6.

To avoid excess pa1 or pb1 primer from amplifying nucleotides in the Stage 2 reaction, one may assure that there is a much greater concentration of Stage 2 primers (pa2 and pb2) by taking small aliquots from each of the 64 Stage 1 reaction vessels and pooling and diluting significantly. One could also limit the amount of any excess pa1 or pb1 primers by using an amount of such primers such that after the complete Stage 1 reaction, the concentration of unused primers is low. Alternatively, various physical separation methods can be used to remove small unincorporated single-stranded primers prior to stage 2. For example, Centricons and Microcons (Amicon; Beverly, Mass.) which separate on the basis of molecular weight and PCR Pure (Boehringer Mannheim; Indianapolis, Ind.) which separates on the basis of molecular weight and by the binding of single-stranded DNA can be used.

After the first stage PCR reactions are complete, the DNA from all of the 64 first-stage vessels is pooled and then split and typically diluted into 64 new stage 2 vessels that contain primer pairs pa2 and pb2. The concentrations of primer pairs pa2 and pb2 typically will be far greater than any residual primers pa1 and pb1. The pa2 primers are designed to hybridize with a sufficient portion of adaptor region A for efficient annealing. They also contain 3 degenerate nucleotides or are ambivalent at positions –4 to –6 from the 3' terminus of the primer (the fourth, fifth, and sixth nucleotide from the 3' terminus), so that the pa2 primers in each of the 64 vessels has the potential to hybridize with any of the 64 possible sets of private nucleotides 1 to 3. Finally, the pa2 primers in each of the 64 vessels contain 3 unique nucleotides at their 3' terminus. These 3 unique nucleotides are complementary to one of the 64 possible combinations of nucleotides 4, 5, and 6 of the private sequence that abut private nucleotides 1 to 3, which were encoded in the first reaction step. Taking into account the 3 degenerate nucleotides, one will use 4096 (64×64) pa2 primers. Each of the 64 vessels will include 64 different pa2 primers that correspond to each possible trinucleotide combination at private sequence portions 1 to 3. All of those 64 pa2 primers in one given vessel, however, will have the same unique trinucleotide corresponding to the particular nucleotides at positions 4 to 6 of the private sequence to be encoded in that vessel. If one uses pa2 primers that are ambivalent at positions corresponding to private nucleotide positions 1 to 3, only 64 pa2 primers are needed since 64 different degenerate combinations at those positions are not needed.

The corresponding pb2 primers are designed to hybridize at their 3' ends with pbcommon1, and to encode information with respect to private nucleotide 4 by adding nucleotides according to the Table 5 presented above with respect to position 4. For example, in any of the 64 vessels where private nucleotide 4 would be C, then amplification using pb2 would add 128 nucleotides to the length of region B such that the distance between the restriction site at the junction of the private sequence and region B, on the one hand, and the 5' terminus of pb2, on the other, would increase by 128 nucleotides. Thus, the total distance between the private region/B region junction corresponding to each combination of private nucleotides 1 to 4 would be equal to the sum of the length of pb1 (including pbcommon1) and the 5' region of pb2 that does not overlap with pbcommon1. For example, if pbcommon1 was 20 nucleotides long and private nucleotides 1 to 4 are GACG, then this distance would be (3+4+32)+(constant 19)+192=270 where the first 39+19 constant were added as the result of the amplification using pb1, and the last 192 as the result of the amplification using pb2.

Synthetic primers longer than about 90 nucleotides may be difficult to synthesize. As an alternative to synthetic primers, DNA created by PCR or other DNA amplification techniques or isolated from plasmids can be used in conjunction with 20- to 30-mer oligonucleotides homologous to the extreme 5' terminus of each DNA fragment. This is possible in this example because the specific composition or identity of much of the nucleotides added by pb2 is irrelevant, only the number of added nucleotides is critical. The methods for making such longer primers, however, are not limited to pb2 primers. The methods can be used to make any long primers that may be used in the present invention.

For example, if a 256 nucleotide extension is needed in the second stage, a 276 nucleotide fragment may be obtained from a PCR product or from a restriction digest of a plasmid, or other DNA source. For example, the PCR product that is discussed here can be obtained by the nested PCR approach that is discussed below. Alternatively, DNA fragments to be used as primers can be inserted into plasmid vectors. The primer is obtained by simply "lifting" the fragment of desired length from the inserted sequence and plasmid between two strategically positioned primers. The primers may anneal to and prime the inserted DNA and/or the plasmid DNA. Additionally, DNA fragments to be used as primers can be isolated from a DNA source by restriction enzyme digestion at preselected sites in the DNA to selectively remove the DNA fragment.

According to certain embodiments, the 20 nucleotides at the 3' end of the 276 nucleotide fragment are complementary to the 20 nucleotides of pbcommon1. The 20 nucleotides at the 5' end of the 276 nucleotide fragment may comprise a new pbcommon2 region. The remaining 236 nucleotides can be from any DNA source. This 276 nucleotide fragment acts as an accessory pb2 primer in the particular PCR vessel. In addition, a 20 nucleotide fragment complementary to pbcommon2 is added to the same vessel in high concentration. The 276 nucleotide fragment merely needs to prime synthesis at the pbcommon1 region to initiate one round of PCR extension. Subsequently, the 20 nucleotide pb2 primer will carry out amplification of the molecules in the remaining rounds.

An alternative approach is to include 4 overlapping 80-mers to create a large pb2 primer. The 80-mers are designed for overlap at their 5' and 3' ends so that a nested PCR can occur which will piece together the desired length pb2 region. For instance, the first 80-mer fragment would include 20 nucleotides at its 3' end that are complementary to pbcommon1 and would include at its 5' end a new 20 nucleotide pbcommon2a region. The second 80-mer fragment would include 20 nucleotides at its 3' end that are complementary to pbcommon2a and would include at its 5' end a new 20 nucleotide pbcommon2b region. The third 80-mer fragment would include 20 nucleotides at its 3' end that are complementary to pbcommon2b and would include at its 5' end a new 20 nucleotide pbcommon2c region. The fourth 80-mer fragment would include 20 nucleotides at its 3' end that are complementary to pbcommon2c and would include at its 5' end a new 20 nucleotide pbcommon2d region.

In the first step of stage 2 of the PCR reaction, the first 80-mer fragment would hybridize to pbcommon1 and extend the 5' end by 60 nucleotides (80–20 nucleotide overlap with pbcommon1). In the second step of stage 2 of the PCR reaction, the second 80-mer fragment would hybridize to pbcommon2a of the first 80-mer fragment and extend the 5' end by 60 nucleotides (80–20 nucleotide overlap with pbcommon2a). In the third step of stage 2 of the PCR reaction, the third 80-mer fragment would hybridize to pbcommon2b of the first 80-mer fragment and extend the 5' end by 60 nucleotides (80–20 nucleotide overlap with pbcommon2b). In the third step of stage 2 of the PCR reaction, the third 80-mer fragment would hybridize to pbcommon2b of the second 80-mer fragment and extend the 5' end by 60 nucleotides (80–20 nucleotide overlap with pbcommon2b). In the fourth step of stage 2 of the PCR reaction, the fourth 80-mer fragment would hybridize to pbcommon2c of the third 80-mer fragment and extend the 5' end by 60 nucleotides (80–20 nucleotide overlap with pbcommon2c). The fourth 80-mer fragment could be used in excess to amplify the DNA to obtain amplified DNA having the appropriate extension for stage 2 of the PCR reaction. In this instance, the extension would be 240 nucleotides (4×60) added to the 5' end of pb1. Alternatively, one could simply use a primer including pbcommon2d in a subsequent amplification step to obtain amplified DNA having the appropriate extension.

All of the steps described above could be accomplished in a single PCR reaction by placing all of the primers in the Stage 2 reaction vessel simultaneously.

One could vary the length of the extension for a particular vessel by varying the lengths of the fragments used in each step (vary from the 80-mer discussed above). One could also vary the size of the pbcommon regions. (As one decreases the size of the overlap of pbcommon regions, more of the nucleotides in a given fragment will contribute to the extension.) As an example, if one is using Table 5 above to encode T in the fourth private position, in stage 2 of the PCR reaction, one must add a 256 nucleotide extension to the 5' end of pb1 from the first stage PCR reaction. Using nested PCR, one could employ four primer fragments for four steps of the stage 2 PCR reaction as discussed above as follows: (1) an 81-mer that includes at its 3' end 20 nucleotides that are complementary to pbcommon1 and includes a new 15 nucleotide pbcommon2a at its 5' end (which adds 61 nucleotides); (2) an 80-mer that includes at its 3' end 15 nucleotides that are complementary to pbcommon2a and includes a new 15 nucleotide pbcommon2b at its 5' end (which adds 65 nucleotides); (3) an 80-mer that includes at its 3' end 15 nucleotides that are complementary to pbcommon2b and includes a new 15 nucleotide pbcommon2c at its 5' end (which adds 65 nucleotides); and (4) an 80-mer that includes at its 3' end 15 nucleotides that are complementary to pbcommon2c and includes a new 15 nucleotide pbcommon2d at its 5' end (which adds 65 nucleotides). Thus, after stage 2 of the PCR reaction is complete, the appropriate target sequences with T at private position 4 will include the 256 nucleotide extension at the 5' end of pb 1.

Yet another alternative approach is to encode a rare restriction site in the pbcommon1 region of the pb1 primers (a restriction site that does not occur in the target gene, if this information is known). Also, one can accomplish selective cleaving, which avoids cleaving restriction sites within the target gene. (See Padgett and Sorge, "Creating Seamless Junction Independent of Restriction Sites in PCR Cloning," Gene, 168:31–35 (1996). The first stage PCR products are mixed and then cleaved with the restriction enzyme that cleaves pbcommon1 to create an overhang in pbcommon1. (Since a portion of pbcommon1 will be deleted in this cleavage step, one may use a pbcommon1 that is significantly shorter than 20 nucleotides in length.) The DNA is distributed to 64 vessels and then ligated with double stranded DNA fragments of the desired length (PCR products, restriction fragments, or annealed oligonucleotides) having a compatible restriction overhang with the overhang created by the cleavage in pbcommon1. Such double stranded fragments are designed to encode pbcommon2 at the end of the molecule opposite from the compatible restriction overhang. The ligated products are amplified with appropriate pa2 and pbcommon2 primers pairs.

Still another alternative method is to mix the first stage amplification products or preamplified target material and ligate them to a blunt end cloning site in a plasmid such as a PCR Script™ following procedures recommended by the manufacturer (Stratagene). The ligated DNA is then distributed into 64 different vessels along with pa2 and pb2 primer sets. (More vessels (for example, 256) can be used for encoding longer stretches of private nucleotides.) Such pb2 primers are designed to prime at appropriate distances from the cloning site of the PCR Script™ plasmid to yield the desired size restriction fragments. In other words, rather than using adaptors or common regions on the preamplified target material or amplification products that primers recognize, one uses primers that recognize sites on the plasmid that are specific different distances from the preamplified target material or amplification products. Thus, one can obtain specific different length amplification products based on the particular location on the plasmid where the particular pb primers commence priming synthesis. The pb primers encode the particular private nucleotides by amplifying particular lengths of the plasmid that correspond to particular private nucleotides. This procedure is used in the procedure directly above in lieu of pbcommon1 cleavage.

In this example, position 5 of the private sequence is encoded by use of four independently distinguishable fluorescent tags on the 5' ends of the pb2 primers. Each different tag corresponds with private nucleotide 5. For example, pa2 primers that read A at position 5 are placed in vessels with a rhodamine labeled pb2 primer. Vessels having pa2 primers that read C at position 5 will also include pb2 primers tagged with fluorescein. The vessels having pa2 primers that read T at position 5 and G at position 5 will likewise each include a unique fluorescent tag on the 5' ends of the pb2 primers to encode the T or G. Each different base at position 5 corresponds with a different color tagged pb2 primer.

The second stage PCR reactions are now run to completion. Upon completion, the vessels for which private nucleotide 6 are identical are pooled so that there will be four separate vessels, one for each possible nucleotide at position 6. One is aware of the sixth private nucleotide in each Stage 2 reaction vessel in view of the particular pa2 primer used in the Stage 2 reaction vessel. In these pools, private nucleotides 1 through 4 will be encoded by the number of nucleotides between the private/region B junction and the 5' fluorescent tag. Private nucleotide 5 will be encoded by the color of the fluorescent tag, and private nucleotide 6 will be encoded by the particular vessel containing the pooled material.

Private nucleotide 7 is encoded during stage 3 of the encoding phase. In stage 3, the DNA in each of the four vessels (one vessel for each possible nucleotide at position 6) is cleaved with a type IIS restriction enzyme that cleaves between private nucleotides 7 and 8 in the fluorescently tagged strand. (In general, one chooses an enzyme that has a recognition site in the adaptor (independent of the private sequence) and that cleaves in the private sequence such that it removes the number of private nucleotides already encoded in addition to the one (or more) private nucleotide to be encoded by the primer extension step.) The recognition sequence for such type IIS enzyme is in the public Region A and the complementary sequence to Region A (pa primer sequence), yet the cleavage site is 7 nucleotides into the private region. The site should not occur anywhere else in the private region or in the pb regions or such other sites should be protected (see Padgett and Sorge, "Creating Seamless Junction Independent of Restriction Sites in PCR Cloning," Gene, 168:31–35 (1996); and McClelland et al., "Effect of site-specific modification on restriction endonucleases and DNA modification methyltransferases" *Nucleic Acids Res.* 22:3640–3659 (1994), which describes the use of methylation to protect DNA containing restriction sites from cleavage)).

For example, an enzyme such as RIeA I, which has the recognition site CCCACA(12/9), could be included in the Region A; Vesely, Z., A. Muller, G. G. Schmitz, K. Kaluza, M. Jarsch and C. Kessler "Rle Al: a novel class-IIS restriction endonuclease from *Rhizobium leguminosarum* recognizing $$5'\text{-CCCACA(N)}_{12}\text{-}3'$$

$$3'\text{-GGGTGT(N)}_{9}\text{-}5'$$

(1990) Gene 95:129. *R. leguminosarum* is available from the American Type Culture Collection (culture numbers 10004 and 10313), the National Collections of Industrial and Marine Bacterial (culture number 11478) and Deutsche Sammiung von Mikroorganismen und Zelijulturen GmbH (culture number DSM301132). (The designation (12/9) indicates that the enzyme cleaves 12 nucleotides from the recognition sequence CCCACA on one strand and 9 nucleotides from the complementary sequence GGGTGT on the other strand.) Other such type IIS enzymes are available.

See, e.g., Szybalski et al., "Class-IIS restriction enzymes—a review" (1991) Gene 100: 13–26.

Figure 12:
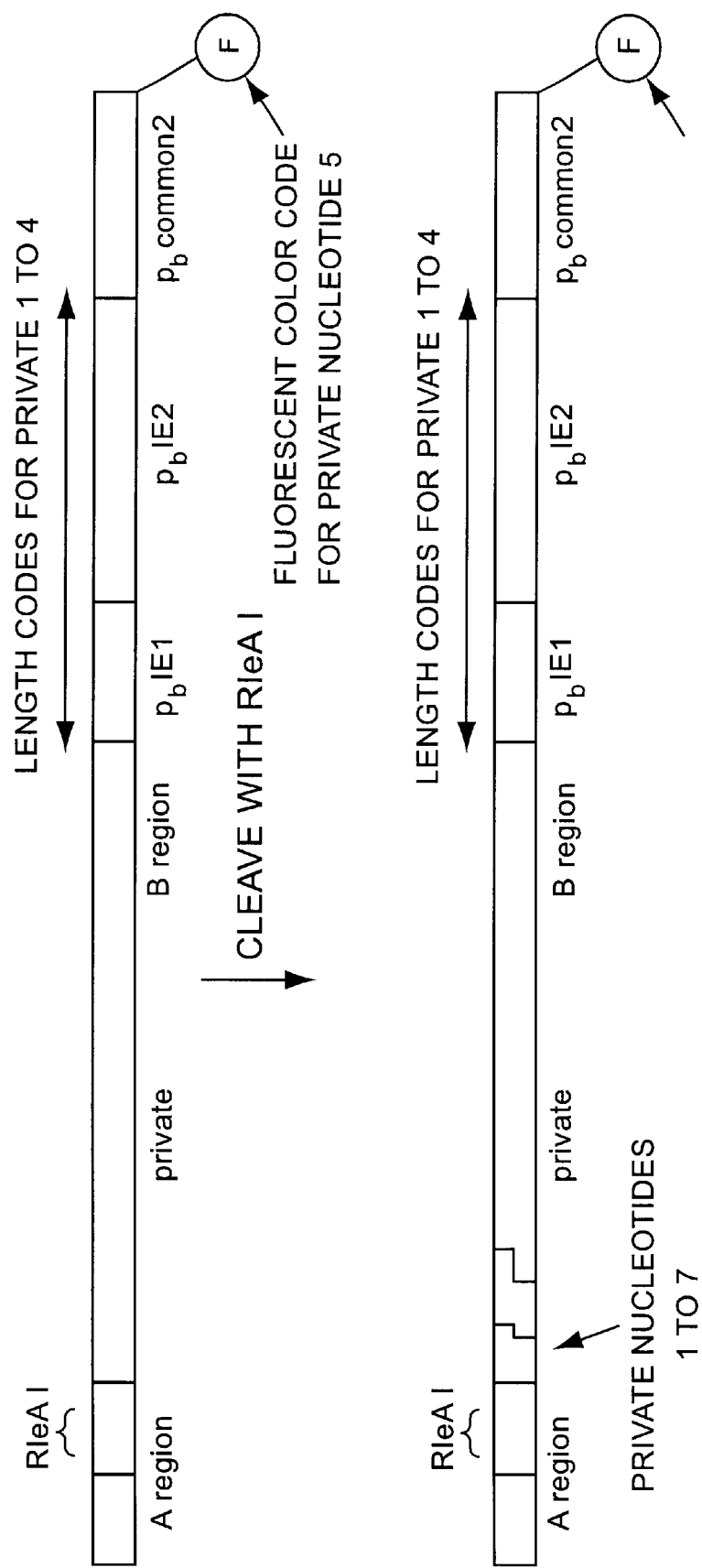
FIG. 12 illustrates cleavage with a type IIS restriction enzyme for subsequent encoding of a private nucleotide by primer extension.

After cleavage with such a type IIS restriction enzyme, private nucleotides 1 to 7 will have been cut away from the DNA strand having the fluorescent tag on its 5' end. See FIG. 12. In this embodiment, the type IIS enzyme used leaves a 3' overhang. In other words, the enzyme cleaves between private nucleotides 7 and 8 of the strand with the fluorescent tag and between nucleotides 10 and 11 on the complementary strand. Such a fluorescently labeled fragment will not prime DNA synthesis when hybridized to its cleaved complementary strand because there is a 3' overhang.

Such DNA can then be denatured and, in preferred embodiments, the complementary strands are removed or selectively digested such that only fluorescenated strands are present (this separation or removal is discussed in more detail below). The fluorescenated strands are then added to target nucleic acids and annealed. The fluorescently labeled strands will hybridize to complementary target nucleic acids that include the nucleotide corresponding to private nucleotide 7 overhanging the 3' end of the flourescenated strand. Thus, if primer extension is initiated, the first nucleotide added to the 3' end of the fluorescenated strand will be nucleotide 7.

To encode nucleotide 7, each of the 4 vessels (corresponding to private position 6) are split into 4 different vessels for 4 different primer extension reactions in which a different biotinylated (or similarly ligand tagged) dideoxy nucleotide triphosphate is present. (Other possible ligands will be known to those skilled in the art and examples are discussed below.) Thus there will be four sets of four reaction vessels. Each set of four will represent a different private nucleotide 6, and the four vessels within each set will each contain a different biotinylated dideoxy nucleotide that will encode a different private nucleotide 7.

For the primer extension reactions according to certain embodiments, DNA exo$^-$ polymerase and appropriate primer extension buffer are added to each vessel and a primer extension reaction is run to completion. Biotinylated dideoxy nucleotide will be added to the 3' ends of the fluorescenated strands provided that the particular dideoxy nucleotide contained in the particular reaction vessel is complementary to private nucleotide 7 in the test DNA. Thus, only those templates bearing a private nucleotide 7 complementary to the particular dideoxy nucleotide in the reaction vessel will cause the fluorescenated strand to become biotinylated.

Exo$^-$ polymerase may be employed since some other polymerases may have exonuclease activity that feasibly could remove nucleotides at the 3' end of the fluorescenated strand. Such removal could introduce errors, since the first nucleotide added in the primer extension reaction is supposed to correspond to private position 7. If private nucleotide 8 at the 3' end of the fluorescenated strand has been removed, however, the first nucleotide added in the primer extension will correspond to private nucleotide 8. Any way to assure that only private nucleotide 7 is encoded in this primer extension procedure is envisioned by the invention.

As discussed above, in certain embodiments, it is desirable to prevent hybridization of the single stranded fluorescently labeled DNA to its complementary strand prior to mixture with the test sample. There are many ways to achieve this goal. For example, one can use an enzyme such as lambda exonuclease, which will digest the non-labeled complementary strand, starting at its 5' phosphate, but will not digest the fluorescenated strand, because the fluorescent molecule protects that strand from digestion. Other methods of separation may be employed. For instance, one could use some form of affinity binding specific to the complementary strand, which does not bind to the fluorescenated strand to separate the complementary strand from the fluorescenated strand. One could alternatively employ physical separation based on a property of the complementary strands that is not shared by the fluorescenated strands. For instance, size separation on a gel may be employed. One skilled in the art will be capable of employing many different types of procedures to achieve this goal, and the invention is not limited to any particular procedure.

The first 7 nucleotides of each different DNA fragment to be sequenced are now encoded by the tags attached to the fragment. All of the different encoded 7 base DNA fragments (7-mers) (which can run into the hundreds, thousands or even more) can now be simultaneously decoded on a single gel in order to reveal multiple overlapping 7-mer sequences of the original DNA sample, that, when pieced together, will give a DNA sequence of the original target DNA sample, including mutations or variations contained therein.

To commence decoding in certain preferred embodiments, the biotinylated DNA strands in each of the 16 reaction vessels are separated from the annealed test DNA fragments. One skilled in the art will be able to accomplish this. For example, one could raise the temperature to obtain single stranded material. The single stranded biotinylated strands are then absorbed to streptavidin on a solid support and washed. Alternatively, biotinylated double stranded DNA strands are absorbed to streptavidin on a solid support and the complementary, nonbiotinylated strand can be removed, for example, by treatment with alkali. The absorbed strands are then cleaved with the restriction enzyme that digests at the private region/public pb region junction. The restriction enzyme recognition site can be included in the pb1 3' end region that is common to all strands (the region complementary to public Region B). For example, one could employ a restriction endonuclease that cleaves single stranded DNA. See, e.g., New England Biolabs 1995 Catalog at page 212. An alternative example is to add a single stranded fragment complementary to the pb1 3' end region that is common to all strands (all or a portion of public Region B). Adding such fragments will result in double stranded fragments at the restriction enzyme recognition site and cleavage can then proceed.

In certain embodiments, one need not separate the biotinylated strand from the annealed test DNA fragments. In such embodiments, the restriction site will already be double stranded in view of the complementary target strand. If the target DNA includes fragments that may not include a complementary strand that extends to the restriction site in the public Region B, one can add a single stranded fragment complementary to the pb1 3' end region that is common to all biotinylated strands (all or a portion of public Region B) as discussed above.

The cleaved DNA is then electrophoresed in 16 separate lanes, one per vessel, in a manner that separates the DNA on the basis of size such that single nucleotide differences are able to be accurately ascertained. Techniques for achieving this are well known in the art. The size of the bands can then be decoded to reveal private nucleotides 1 to 4, the color of the bands represents private nucleotide 5, and the particular lane on the gel reveals private nucleotides 6 and 7. Tags showing up in a particular lane will all have a known combination of private nucleotides 6 and 7, because any strands from each particular vessel that are absorbed by streptavidin must have a known particular combination of nucleotides at positions 6 and 7. One knows position 6 in view of the prior physical pooling separation step (one knows that only amplified strands with a known nucleotide at position 6 are in each particular vessel). One knows position 7 for each vessel, since only strands with a given nucleotide at position 7 will be biotinylated, and only such strands will have been captured by the streptavidin.

Thus, if vessel 1 contained only amplified strands with nucleotide A at position 6 and contained biotinylated nucleotide A at position 7, if tag from vessel 1 shows up in column 1, one knows that the 7-mer that had been encoded includes AA at positions 6 and 7. Similarly, if vessel 2 contained only amplified strands with nucleotide A at position 6 and contained biotinylated nucleotide T at position 7—if tag from vessel 2 shows up in column 2, one knows that the 7-mer that had been encoded includes A T at positions 6 and 7.

Thus, in combination with the information encoded for private nucleotides 1 to 5 as discussed above, the 16 lanes on a typical DNA sequencing gel will reveal essentially all of the 7-mers in a given target DNA fragment. This provides information on the 47 (16,384) possible sequences of the 7-mers.

One can then compile all of the information concerning the 7-mers to deduce the entire sequence that is sought. Assembly of such information is known to those skilled in the art. For example, one can employ the methods discussed in Lipshutz, "Likelihood DNA Sequencing by DNA Hybridization," J. Biomolecular Struct. and Dynamics, 11 (3):637–653 (1993) and in Lysob et al., "DNA Sequencing by Contiguous Stacking Hybridization on Modified Oligonucleotide Matrices," Molecular Biology, 29:62–66 (1995).

Depending on the size of the DNA being sequenced, one may want to encode more than 7 nucleotides of each fragment. By increasing the number of nucleotides encoded, one decreases the possibility of not identifying repeat sequences located at different positions in the sequence sought or in an expressed genome being analyzed. For instance, if an unknown sequence has a stretch of 10 identical nucleotides and only 7-mers are being encoded, one typically will have difficulty detecting the presence of the interior identical nucleotides. The first six and last six identical nucleotides may be detected since they will include overlap with other nucleotides. If one encoded, e.g., 18 nucleotides, however, such stretches could be accurately detected. Thus, certain preferred embodiments encode any number of nucleotides. In certain preferred embodiments, that number is between 7 and 20. Of course, the complexity of the encoding is increased with each additional nucleotide encoded.

According to certain embodiments, one may also be able to assess whether there are repeat sequences by correlating the size of a band on the gel with the number of 7-mer stretches of the same nucleotides.

EXAMPLE 3
A Method for Detecting Mutations, Including Substitutions, Deletions, and Insertions in a Target Gene Using DNA Amplification Techniques and Uniquely Identifiable Tags The DNA sequencing method described above in Example 2 can be adapted to kits so that end-users can rapidly detect mutations, including substitutions, deletions, and insertions in a target gene. Such a test would be valuable in examining genes where any one of hundreds of possible mutations can cause a disease. For example, certain cancer-related gene mutations are known to occur at many possible locations in the respective genes. For another example, cystic fibrosis is also associated with a multitude of potential mutations.

In this embodiment of the invention, probe DNA can be prepared as described above in Example 2. The source of the probe DNA is a known wild type gene that does not contain any mutations, including substitutions, deletions, or insertions. Known flanking DNA is added on both ends of the wild type gene prior to the initial shearing step discussed above in Example 2. The procedures of Example 2 are then carried using combinatorial PCR in batch up through the cleavage using a type IIS restriction enzyme and subsequent denaturing at the beginning of Stage 3.

The probes will thus be provided in 4 different containers and will comprise the single stranded fluorescenated strand in which the length between the private region/pb region junction and the fluorescent molecule encodes private nucleotides 1 to 4 of each fragment, the color of the fluorescent molecule encodes private nucleotide 5, and the container encodes private nucleotide 6. The probes will have been cleaved between private nucleotides 7 and 8, and thus, will have private nucleotide 8 at their 3' ends. This probe DNA is then placed into kits for transfer to end-users. The end-user will then only need to run the remainder of the procedure of Example 2, in which nucleotide 7 is represented by a biotinylated nucleotide, with test DNA specimen fragments and wild type test DNA fragments in parallel.

The wild type test DNA fragments will be DNA fragments prepared above by adding to the wild type gene the flanking DNA and then shearing. (The material used to make the probes that has not been subjected to the combinatorial PCR reactions.) The wild type test DNA fragments can be provided with the kit.

The test DNA specimen fragments will be prepared by the end-user by adding to both ends of the test gene the same flanking DNA used to create the wild type probes and wild type test fragments provided in the kit. The end-user will then shear that test gene using the same protocol used to shear the wild type gene used to create the wild type probes and the wild type test fragments.

For primer extension of the test DNA fragments, the end-user will split half of each of the four containers of probes into four different primer extension vessels, resulting in 16 different vessels. For primer extension of the wild type test DNA fragments, the end-user will split the other half of each of the four containers of probes into four different primer extension vessels, resulting in another 16 different vessels. In parallel for the wild type test DNA fragments and the test DNA fragments, following the procedures in Example 2, the end-user will then carry out the primer extension reactions, bind the products to streptavidin beads (if the affinity agent was biotin, if not, then the products are bound to the appropriate binding agent), wash, release the fragments with a releasing agent such as a restriction enzyme, and analyze the tag population, for example by loading the released DNA fragments on an electrophoresis gel. Comparison of the tag signals will then reveal mutations, including substitutions, insertions, and deletions in the test DNA.

One only needs to perform the last primer extension step, since only the seventh position of each 7-mer private sequence will need to be determined from the test sample for the comparison between the wild type fragments and the test fragments. The wild type sequence will be completely encoded by the prepared probes and the last primer extension step. Thus, the parallel reaction using wild type DNA will provide the 7-mer sequences in the wild type gene corresponding to the test gene being assessed. Since the collection of 7-mer fragments should include random overlapping of each nucleotide of the entire wild type gene, within the collection of 7-mer sequences, each nucleotide of the entire wild type gene should be represented at a private position 7 of at least one of the fragments.

In other words, the first 7-mer sequence containing the first nucleotide of the wild type sequence would include known flanking DNA at positions 1 to 6, and the first wild type nucleotide would be at position 7. The next 7-mer sequence would include known flanking DNA at positions 1 to 5, the first wild type nucleotide at position 6, and the second wild type nucleotide at position 7. The next 7-mer sequence would include known flanking DNA at positions 1 to 4, the first wild type nucleotide at position 5, the second wild type nucleotide at position 6, and the third wild type nucleotide at position 7. This would continue up to the last 7-mer sequence, which contains only wild type DNA without known flanking DNA, such that the last nucleotide of the wild type gene is contained at position 7. (There would be other 7-mer sequences that begin with wild type nucleotides at positions 1 up to 6, and the rest would be known flanking DNA. Those 7-mers allow one to locate the terminus of the wild type gene.)

Since at least one 7-mer sequence will include each consecutive nucleotide of the wild type sequence at position 7, differences between the wild type 7-mer results and the test sample 7-mer results can highlight differences between the entire wild type gene sequence and the entire sequence of the test sample DNA.

Since all of the n-mers (7-mers in the above example) in the test sample and the wild type sample will be seen, there will be substantial redundancy in the information, providing significant confirmation of results.

This method provides a powerful liquid phase process for detecting mutations, including substitutions, deletions, insertions, and normal sequence in a target gene. This test could be used to examine genes where any one of hundreds of possible mutations can cause disease.

In these embodiments of the invention, the issue of repeat sequences found at different positions in the gene is easily addressed. One will already know the sequence of the wild type gene being compared to the test DNA. Thus, one will be aware of such repeat sequences in the wild type gene. If one detects in the test DNA fragments a change from one of wild type repeat sequences, the actual location of the change can be ascertained by separately sequencing individual nucleotides in each of the locations known to correspond to the wild type repeat sequences. The kit could include restriction enzymes known to cut the wild type DNA in regions containing the repeat sequences. It is possible that another mutation could have changed the restriction enzyme recognition sites in the specimen DNA. One skilled in the art, however, would know how to use alternate restriction enzymes to obtain suitable fragments.

EXAMPLE 4
A Method for Monitoring the Levels of mRNA Using DNA Amplification Techniques and Uniquely Identifiable Tags Another application for the invention described in this application is to monitor the relative expression levels of a large population of mRNA molecules. Information with respect to relative mRNA levels can be very valuable for assessing physiologic or disease states.

In order to prepare probes from a reference mRNA population, a nucleic acid population is placed between adaptor regions A and B as described in Example 2. For these embodiments of the invention, however, the nucleic acid population comes from cDNA prepared from the target mRNA population to be measured; the cDNA population is normalized using techniques such as SAS (U.S. Pat. application Ser. No. 60/033175, filed Dec. 13, 1996, Ser. No. 08/775,993, filed Jan. 3, 1997, Ser. No. 08/779,355, filed Jan. 6, 1997, and a CIP application of the Ser. Nos. 08/775,993 and 08/779,355 applications, which was filed on Sep. 26, 1997) or suppression subtractive PCR. See, for example, Diatchenko et al., "Suppression subtractive hybridization: A method for generating differentially regulated or tissue-specific cDNA probes and libraries," PNAS 93:6025–30 (Jun. 1996); U.S. Pat. No. 5,565,340. Additionally, instead of shearing the DNA, the cDNA is cleaved with a restriction enzyme prior to placement between public regions A and B. The recognition sequence of the restriction enzyme provides information about the target mRNA nucleic acid sequence at or immediately preceding the private region sequence between regions A and B. The combinatorial sequencing techniques, such as those described previously, are then used to provide additional sequence information. Ultimately, the information acquired by the combinatorial sequencing techniques is added to the information acquired from the recognition sequence of the restriction enzyme, and the specific cDNAs (and thus, the specific mRNAs) present in the standard or test population are identified.

In addition to identifying the presence of the specific cDNAs (and thus, the specific mRNAs) in the target population, the invention can provide the relative concentrations of each by the relative intensity of the fluorescent bands on the decoding gel. This can be achieved if the fluorescently labeled probes are in relatively equal concentrations prior to hybridization with the target as discussed below or if the intensity of the bands is compared directly to the intensity of bands created with a control mRNA sample.

According to these embodiments of the invention, it is possible to create pre-prepared kits for use by the end-users, and the kits can contain all of the probes necessary to detect mRNA levels from a single person or cell source.

The probes for monitoring the expression of mRNA levels can be created in many ways. One specific example is given in order to illustrate one possible embodiment of this invention, and this embodiment in no way limits the scope of the invention.

To create probes from a reference mRNA population, double-stranded cDNA is created from the reference mRNA population. The first strand of cDNA synthesis is primed with oligo-dT primers or with random primers. The cDNA is then digested with a restriction enzyme that cleaves frequently, such as a restriction enzyme with a four-nucleotide recognition sequence such as the enzyme Mbo I. Such enzymes cleave DNA approximately every 256 nucleotides. Adaptor regions A and B are designed to have Mbo1 compatible overhangs such that the region A and region B are added to the correct strand. This can be accomplished according to certain embodiments by ligation. In certain embodiments, the adaptors typically comprise two oligonucleotides which are annealed at regions of complementarity. The following is but one example of how ligation can be accomplished. To create each adaptor, equal molar amounts of the two oligonucleotides are combined, heated, and slowly cooled to a temperature at which the oligonucleotides specifically anneal. Adaptors having different nucleotide sequences are ligated simultaneously in equal molar amounts to the fragments. The ratio of picomole ends of adaptors to fragments can be varied to increase the ligation efficiency and is typically at least 3:1 (adaptors:fragments). Adaptors and fragments are combined and incubated in 1× ligase buffer (1× ligase buffer is 50 mM tris-HCl [pH 7.5], 7 mM $MgCl_2$, 1 mM dithiothreitol [DTT] and 1 mM rATP) with 2 units of T4 DNA Ligase (Stratagene; La Jolla, Calif.)

at a temperature which favors annealing of the adaptor oligonucleotides and enzymatic activity and for a sufficient amount of time for ligation to occur.

Primers pa are designed with a rare type IIS restriction enzyme recognition site situated so that it will cleave near the region A/private region junction, eight nucleotides away from the Mbo I site in the private DNA (between private nucleotides 12 and 13 with respect to the Mbo I site at private nucleotides 1 to 4). Primers pb are designed to place a restriction cleavage site at the private region/region B junction (which could be the Mbo I site itself in this example).

In addition, in the first stage of combinatorial PCR, the primers pa are designed with the knowledge that the first four nucleotides of the private sequence will be GATC for all molecules, corresponding to the Mbo I site used to prepare the cDNA for ligation to adaptor regions A and B. Thus, the pa1 primers will each include the complementary CTAG in the region immediately preceding the nucleotides that will read private positions 5 and 6. And, the pa2 primers will include the complementary CTAG immediately preceding the degenerate positions corresponding to private positions 5 and 6, which are followed by particular nucleotides that read private positions 7 and 8. Both the first and second stages of combinatorial PCR may be carried out using 16 vessels (one vessel for each of the 16 different dinucleotide combinations at private positions 5 and 6 in the first stage, and one vessel for each of the 16 different dinucleotide combinations at private positions 7 and 8 in the second stage), and the information for private positions 5 to 8 is encoded in primers pb as 256 different lengths, similar to private regions 1–4 described in the DNA sequencing discussed in Example 2 above.

After mixing the second stage vessels, the third stage is carried out using 64 different vessels. The pa3 primers are designed with a sequence of 5'-paNNNNXXX-3', where N is an equal mixture of A, C, G, and T, and each X is only one of A, C, G, and T such that each of the 64 different tubes has a different permutation of the XXX triplet. (The pa portion of the primer will include CTAG (corresponding to the GATC Mbo I site) immediately preceding NNNNXXX.) The pb3 primers are 5' tagged with a fluorescent molecule, such that the color corresponds with the identity of private nucleotide 11 (corresponding to the X at the 3' end of the pa3 primers).

After the third stage combinatorial PCR reactions have run to completion, the 64 reaction vessels are pooled into 16 separate vessels such that each of the 16 vessels contains a different dinucleotide combination of private nucleotides 9 and 10. (Positions 9 and 10 of each of the 64 reaction vessels will be known in view of the particular pa3 primers used in the reaction vessel.) Each pool (vessel) contains DNA having identical private nucleotide positions 9 and 10, and contains four different fluorescent tags corresponding to each possible private nucleotide 11. One then cleaves the DNA in the 16 vessels at the type IIS restriction site encoded in pa such that private nucleotides 1 to 12 are cleaved from the fluorescently labeled strand and a 3' overhang on that strand is produced. (Restriction enzymes Bpm I, Bsg I, or Eco57 I can accomplish this. Those three enzymes are commercially available from the 1997 New England Biolabs (Beverly, Mass.) catalog.) (See Padgett and Sorge, "Creating Seamless Junction Independent of Restriction Sites in PCR Cloning," Gene, 168:31–35 (1996); and U.S. Pat. application Ser. No. 60/033175, filed Dec. 13, 1996, Ser. No. 08/775,993, filed Jan. 3, 1997, 08/779,355, filed Jan. 6, 1997, and a CIP application of the Ser. Nos. 08/775,993 and 08/779,355 applications, which was filed on Sep. 26, 1997). The DNA of these vessels is then denatured to create single stranded DNA and the DNA strand complementary to the fluorescently labeled strand is digested or otherwise removed or separated from the fluorescently labeled strand as discussed in Example 2.

These fluorescently labeled strands can then be used as probes to identify target cDNA or mRNA. These probes can be included in pre-prepared kits for end-users.

Specifically, the 5' fluorescently labeled strands are used to hybridize with target mRNA or cDNA added by the end-user. Thus, for example, the end-user adds the target sample of mRNA or cDNA to 64 different vessels so that 64 primer extension reactions can be carried out using the 16 probe pools split into 4 subpools. Each of the 16 probe pools are divided into 4 subpools such that each of the four includes one of biotinylated (or other ligand) ddATP, ddCTP, ddGTP, or ddTTP for primer extension reactions. If mRNA is used as the template, then reverse transcriptase would be used to incorporate the dideoxy nucleotides.

These 64 different primer extension products are then bound to a streptavidin (or other affinity) solid support, washed, and then cleaved with Mbo I at the restriction site at the private region/pb region junction. The 64 different samples are then electrophoresed in 64 separate lanes. These 64 lanes will contain the sequence of private nucleotides 1 to 12 for all mRNAs in the target population. Specifically, private nucleotides 1 to 4 are known by virtue of the restriction enzyme Mbo I; private nucleotides 5 to 8 are known by decoding the length of the fragment on the gel; private nucleotides 9, 10, and 12 are known by decoding the lane in which the band is found (each of the 64 lanes corresponds to each possible combination of nucleotides at private positions 9, 10, and 12 (43 possible combinations)); and private nucleotide 11 is known by decoding the color of the fluorescent band.

In addition, provided that the fluorescently labeled probes are in relatively equal concentrations prior to the hybridization with the target, the intensity of the bands will reflect the relative abundance of each mRNA species. Thus 64 lanes on an electrophoretic gel will reveal the identity and relative concentrations, with respect to a reference mRNA population, of all or most mRNAs of a test sample.

If needed, private nucleotides 1 to 13 of all mRNAs could be obtained using the same methods by using 256 primer extension vessels and 256 gel lanes. (The 256 different lanes would decode private nucleotides 9, 10, 12, and 13.) This would provide as many private nucleotides as the SAGE technique (Velculescu, V., Zhang L., Vogelstein, B., and Kinzler, K. W. Science 270: 484–487, 1995), yet would provide such information on many more mRNAs with less effort on the part of the end user.

If private nucleotides 1 to 14 were desired, one could cleave the starting cDNA with a restriction enzyme that recognizes 5 nucleotides, ligate A adaptors, cleave with a different enzyme that recognizes different nucleotides, such as one that recognizes 4 nucleotides, to shorten the average fragment length, and then ligate B adaptors. In this way, private nucleotides 1 to 5 will be defined by the 5-nucleotide restriction site.

EXAMPLE 5

Testing of Conditions for Primer:Template Pairing

A. Preparation of Circular Templates Having Public and Private Regions

Figure 13:
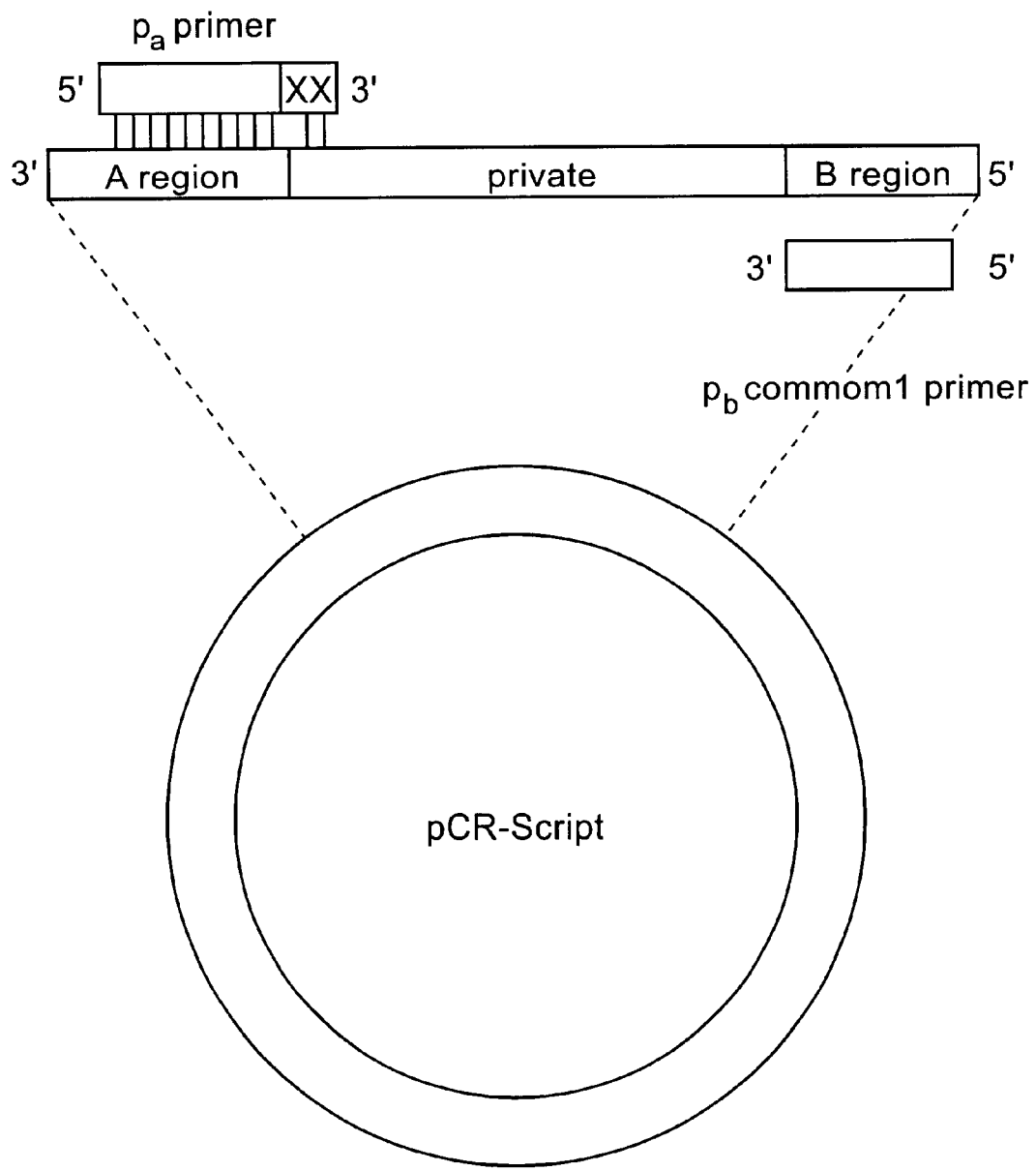
FIG. 13 shows the use of a plasmid for amplifying templates.

Seven circular templates having public and private regions were constructed for use in optimizing priming conditions. Those circular templates were prepared by annealing and inserting seven pairs of oligonucleotides into a circular plasmid vector FIG. 13). Each pair of annealed oligonucleotides comprised a public region of 21 identical nucleotides (A region) and a private region of 8 to 32 nucleotides (Table 6).

7.5; heating at 70° C. and slowly cooling to room temperature. The annealed oligonucleotides were inserted into the pCR-Script™ Amp SK(+) vector using the manufacturer's directions. DNA representing the circular templates was isolated and the nucleotide sequence determined using

TABLE 6

Nucleotide Sequence of Oligonucleotides Used to
Prepare Circular Plasmids Having Public and Private Domains

| Template | Nucleotide Sequence of Oligonucleotides | | SEQ ID NO.: |
|---|---|---|---|
| | Public Region | Private Region | |
| 1 | 5'-C TGC AGG TCA GCC TAA CGT CA<br>3'-G ACG TCC AGT CGG ATT GCA GT | <u>AA</u> AAG CTT-3'<br><u>TT</u> TTC GAA-5' | |
| 2 | 5'-C TGC AGG TCA GCC TAA CGT CA<br>3'-G ACG TCC AGT CGG ATT GCA GT | <u>AC</u> TCA AGC TT-3'<br><u>TG</u> AGT TCG AA-5' | |
| 3 | 5'-C TGC ACG TCA GCC TAA CGT CA<br>3'-G ACG TCC AGT CGG ATT GCA GT | <u>AG</u> TCG AAA GCT T-3'<br><u>TC</u> AGC TTT CGA A-5' | |
| 4 | 5'-C TGC AGG TCA GCC TAA CGT CA<br>3'-G ACG TCC AGT CGG ATT GCA GT | <u>AT</u> TCG ACA AAG CTT-3'<br><u>TA</u> AGC TGT TTC GAA-5' | |
| 5 | 5'-C TGC AGG TCA GCC TAA CGT CA<br>3'-G ACG TCC AGT CGG ATT GCA GT | <u>CA</u> TCG ACA AGA AGC TT-3'<br><u>GT</u> AGC TGT TCT TCG AA-5' | |
| 13 | 5'-C TGC AGG TCA GCC TAA CGT CA<br>3'-G ACG TCC AGT CGG ATT GCA GT | <u>TA</u> TCG ACA AGG TCT GAG TCA GTT CTG AAG CTT-3'<br><u>AT</u> AGC TGT TCC AGA CTC AGT CAA GAC TTC GAA-5' | |
| 16 | 5'-C TGC AGG TCA GCC TAA CGT CA<br>3'-G ACG TCC AGT CGG ATT GCA GT | <u>TT</u> TCG ACA AGG TCT GAG TCA GTT CTG AGC AGT AAG CTT-3'<br><u>AA</u> AGC TGT TCC AGA CTC AGT CAA GAC TCG TCA TTC GAA-5' | |

In these constructs, the public region (having a pa primer binding site) is followed a private region. The first two nucleotides in the private region adjacent to the public region are unique (underlined) and represent seven of the sixteen possible dinucleotides. The remaining six to thirty nucleotides of the private region are unique and are used to identify the templates by the length of the PCR products amplified when using the templates in later examples. Region B, having a priming site for the pbcommon1 primer, is from base pair position 1048 to 1079 of the pCR Script plasmid and therefore is 339 bases in length.

Only 7 of the possible 16 circular templates were selected for the initial studies based upon previous studies indicating that the presence of a T at the 3' end of a primer provided efficient amplification of a given DNA template irrespective of the corresponding nucleotide in the template. Kwok, S., D. E. Kellogg, N. McKinney, D. Spasic, L. Goda, C. Levenson and J. J. Sninsky "Effects of primer-template mismatches on the polymerase chain reaction: Human immunodeficiency virus type I model studies" (1990) Nucleic Acids Res. 18:999. The seven templates represent the dinucleotides TT, TG, TC, TA, GT, AT and AA in the template strand at the first two nucleotides of the private region (Table 6). The use of template 1 is described in this Example. The use of templates 2–6, 13 and 16 are described Example 6.

To prepare the circular templates, the complementary oligonucleotides were annealed and inserted into circular plasmid vector, pCR-Script™ (Stratagene; La Jolla, Calif.— cat#211188, GenBank Accession #U46017) at the unique Srf I restriction site. The oligonucleotides shown in Table 6 were prepared using standard phosphoroamidite chemistry and an ABI synthesizer. Six micrograms (pg) of each oligonucleotide were annealed in pairs as shown in Table 6 by combining the oligonucleotides in 5 millimolar (mM) Tris-Cl and 1 mM ethylenediaminetetraacetic acid (EDTA), pH Sequenase (U.S. Biochemical; Cleveland, Ohio). The nucleotide sequence confirmed that the circular templates contained a single copy of the public and private regions in the desired orientation. Thus, circular templates having pa and pb1 common priming sites and representing seven of the sixteen possible dinucleotide combinations at the first two nucleotides in the private region were prepared for use as templates in the following primer specificity experiments.

B. Priming Specificity Experiments

The purpose of these experiments was to optimize conditions for amplifying a template using primers in which all of the nucleotides of the template and primer base pair (100% homology) and not amplify a template when using primers in which one or more of the nucleotides of the template and primer do not base pair (less than 100% homology). In these experiments, a primer that is 100% homologous to the template is referred to as a matched primer and a primer that is less than 100% homologous to the template is referred to as a mismatched primer. When a primer is mismatched, either the first or second nucleotide or both the first and second nucleotides of the private region do not base pair with the template.

Sixteen primers which anneal to nucleotides 7–21 of the public region (region A) and nucleotides 1–2 of the private region (Table 7) were designed and synthesized as described above. The nucleotide sequence of primers 384 through 399 in nucleotide position 1–15 are identical. The last two nucleotides of the primers represent all possible combinations of dinucleotides and are underlined.

TABLE 7

Nucleotide Sequence of pa Primers

| Primer | Nucleotide Sequence (5'→3') | SEQ ID NO.: |
|---|---|---|
| 384 | GTC AGC CTA ACG TCA AA | |
| 385 | GTC AGC CTA ACG TCA AC | |
| 386 | GTC AGC CTA ACG TCA AG | |
| 387 | GTC AGC CTA ACG TCA AT | |
| 388 | GTC AGC CTA ACG TCA CA | |
| 389 | GTC AGC CTA ACG TCA CC | |
| 390 | GTC AGC CTA ACG TCA CG | |
| 391 | GTC AGC CTA ACG TCA CT | |
| 392 | GTC AGC CTA ACG TCA GA | |
| 393 | GTC AGC CTA ACG TCA GC | |
| 394 | GTC AGC CTA ACG TCA GG | |
| 395 | GTC AGC CTA ACG TCA GT | |
| 396 | GTC AGC CTA ACG TCA TA | |
| 397 | GTC AGC CTA ACG TCA TC | |
| 398 | GTC AGC CTA ACG TCA TG | |
| 399 | GTC AGC CTA ACG TCA TT | |

1. Effect of DNA Polymerase on Priming Specificity

This experiment tested the ability of different DNA polymerases to amplify a template when annealed to matched and mismatched primers. Four sets of sixteen separate PCR were performed using a template having TT in the variable region (Template 1 in Table 6), the pbcommon1 primer (SEQ ID NO.: **; 5'-GCGCAGCGCAGCGAGTCAGTGA-3') and the 16 primers given in Table 7. Each set of sixteen PCR was performed with one of the following DNA polymerases: TaqPlus® Long PCR System and Pfu DNA polymerases which have 3'→5' exonuclease activity and Taq and Exo(−)Pfu DNA polymerases which do not have 3'→5' exonuclease activity. The cycling conditions were one cycle of 93° C. for 3 minutes, 54° C. for 3 minutes, and 68° C. for 1 minute; thirty cycles of 93° C. for 45 seconds, 54° C. for 45 seconds, and 68° C. for 1 minute; and one cycle of 68° C. for 10 minutes. The expected sizes for the PCR products are between 360 and 384 base pairs. The PCR products were separated according to molecular weight by agarose gel electrophoresis, stained with ethidium bromide and visualized by ultraviolet light.

Results of the DNA polymerase priming specificity experiment are shown in Table 8. PCR with the matched primer and template resulted in a high amount of product. Template and primer having a single mismatch were amplified by all DNA polymerases. The position of the single mismatch (at the first or second nucleotide) did not effect the results. All of the templates with a primer having two mismatches were amplified by TaqPlus® Long PCR System and Pfu DNA polymerases and not with Exo(−) Pfu DNA polymerase. In general, the use of Exo(−) Pfu DNA polymerase resulted in less PCR product than the other polymerases tested. All of the template and primers having single mismatches and some of the PCR having two mismatches were amplified with Taq DNA polymerase.

TABLE 8

Results of Amplification of a TT template Using Matched and Mismatched Primers and Different DNA Polymerases

| Primer | Primer Sequence at Nucleotides 1 and 2 of the Private Region | DNA Polymerase | | | |
|---|---|---|---|---|---|
| | | Taq | TaqPlus ® | Pfu | Exo(−)Pfu |
| | | Amount of PCR product | | | |
| 384 | AA | ++ | ++ | ++ | + |
| 385 | AC | ++ | ++ | ++ | + |
| 386 | AG | ++ | ++ | + | + |
| 387 | AT | ++ | + | ++ | + |
| 388 | CA | ++ | ++ | + | + |
| 389 | CC | + | + | + | − |
| 390 | CG | − | + | + | − |
| 391 | CT | − | + | + | − |
| 392 | GA | ++ | ++ | ++ | + |
| 393 | GC | + | + | + | − |
| 394 | GG | − | + | ++ | − |
| 395 | GT | − | + | + | − |
| 396 | TA | ++ | ++ | ++ | + |
| 397 | TC | − | + | + | − |
| 398 | TG | − | + | + | − |
| 399 | TT | − | + | + | − |

(− is no PCR product, + is PCR product, ++ is a high amount of PCR product)

As expected, the results of this experiment indicate that the absence of 3'→5' exonuclease activity is optimal for priming specificity of matched primers and templates according to certain embodiments. DNA polymerases which have 3'→5' exonuclease activity will remove one or more mismatched nucleotides in the first two nucleotides of the private region of a mismatched primer and generate a product. As Taq and Exo(−) Pfu DNA polymerase were the most consistent in specifically priming, they were used in the next experiment.

2. Effect of Annealing Temperature on Priming Specificity

To further define conditions resulting in priming specificity, the effect of a range of annealing temperatures on the priming of a template by a matched primer and a primer having a single mismatch was examined. A gradient of annealing temperatures in 2° C. increments from 54° C. to 68° C. and Taq and Exo(−) Pfu DNA polymerases were used. These polymerases were selected by their ability to selectively amplify using either matched primers or primers having one mismatch in the previous experiment. For each polymerase, eight PCR reactions were performed with the matched primer and template (AA in the variable region of the primer and TT in the variable region of the template) and the pbcommon1 primer. In addition, eight reactions were performed with a single mismatched primer and template (AC in the variable region of the primer and TT in the variable region of the template) and the pbcommon1 primer. The expected sizes of the PCR products are between 360 and 384 base pairs. The cycling conditions were the same as in the first experiment, except that each of the eight reactions was annealed at a different temperature within the range given above.

The results of the amplification with matched and mismatched primers at a range of different annealing temperatures are shown in Table 9. In this experiment, both Taq and Exo(−) Pfu DNA polymerases amplify both templates at 54° C., and Taq does not show an increase in priming specificity at higher annealing temperatures (Table 9). However, Exo (−) Pfu DNA polymerase amplifies with the matched primer but not the mismatched primer at 56° C. and slightly at 58° C.

TABLE 9

Results of Amplification Using Matched and Mismatched Primers at Different Annealing Temperatures with Two Different DNA Polymerases

| Annealing Temperature | Amount of PCR product | | | |
|---|---|---|---|---|
| | Matched Primer AA | | Mismatched Primer AC | |
| (° C.) | Taq | Exo(−)Pfu | Taq | Exo(−)Pfu |
| 54 | ++ | ++ | ++ | + |
| 56 | + | + | + | − |
| 58 | − | + | + | − |
| 60 | − | − | − | − |
| 62 | − | − | − | − |
| 64 | − | − | − | − |
| 66 | − | − | − | − |
| 68 | − | − | − | − |

(− is no PCR product, + is a low amount of PCR product, ++ is a high amount of PCR product)

The results of the annealing temperature indicate that higher annealing temperature increases priming specificity when using Exo(−) Pfu DNA polymerase and that an increase of more than 2° C. reduces the amount of product amplified with the matched primer. Thus, priming specificity conditions using Exo(−) Pfu DNA polymerase and annealing temperature 56° C. were used in Example 6.

EXAMPLE 6

Further Testing of Conditions for Primer Pairing

Additional conditions for optimizing the specificity of primer pairing were tested. Specifically, concentration of dNTP, "Hot Start" techniques, and "TouchDown" techniques were tested.

"Hot Start" techniques involve delaying the interaction of reaction components in PCR until specific conditions such as a threshold temperature is reached. In certain embodiments, such a delay is achieved by separation or segregation of the polymerase and/or Mg and/or dNTP from the primer and template until the threshold conditions such as minimum temperature is reached. See, for example, Erlich et al., "Recent advances in the PCR," Science, 253:1643–1651 (1991); Powel, "Protocol Optimization and Reaction Specificity, in PCR Essential Data," edited by Newton C. R., J. Wiley & Sons (1995) pp. 72–77. In certain embodiments, one can achieve segregation of reaction components by placing a component or components in wax beads, which melt at the threshold temperature at which optimal matched priming occurs (priming in which the primer properly matches the template). See, for example, Newton, "Setting Up a PCR Laboratory, in PCR Essential Data," edited by Newton C. R., J. Wiley & Sons (1995) p.10.

"TouchDown" techniques involve using higher temperatures for the first cycles of PCR and gradually reducing the temperature for subsequent cycles. In certain embodiments, one eventually reaches a minimum constant temperature that is used for the balance of the cycles that are performed. See, for example, Vos et al., "AFLP: a new technique for DNA fingerprinting," Nucl. Acids Res., 23:4407–4414 (1995); Money et al., "AFLP-based mRNA fingerprinting," Nucl. Acids Res., 24:2616–2617 (1996).

Variations in the type and concentration of activating divalent metal ion, the pH, and the dNTP concentration are known to influence the rate and processivity of polymerization (efficiency of polymerization) with different polymerases. See, for example, Erlich et al., "Recent advances in the PCR," Science, 253:1643–1651 (1991); Cline et al, "PCR fidelity of Pfu DNA polymerase and other thermostable DNA polymerase," Nucl. Acids Res., 24:3546–3551 (1996); Liang et al. "An efficient and optimized PCR method with high fidelity for site-directed mutagenesis," PCR Methods and Applications, 4:269–274 (1995); Eckert et al., "High fidelity DNA synthesis by Taq DNA polymerase," Nucl. Acids Res., 18:3739–3744 (1990).

High fidelity DNA synthesis by Taq (Liang et al., PCR Methods and Applications, 4:269–274 (1995); Eckert et al., Nucl. Acids Res., 18:3739–3744 (1990)) and Pfu (Cline et al, Nucl. Acids Res., 24:3546–3551 (1996)) DNA polymerases seem to be stimulated by low pH (Liang et al., PCR Methods and Applications, 4:269–274 (1995); Eckert et al., Nucl. Acids Res., 18:3739–3744 (1990)) and low dNTP and $Mg^{2+}$ concentration. Initial experiments with Pfu (Exo-) showed excellent results using 20 mM PIPES pH 6.5 that was used for further experiments. The actual buffer system was as follows:

Buffer System:

| 10 × Buffer Composition (1 ml) | Stocks |
|---|---|
| 200 µl PIPES pH 6.5 | 0.5M |
| 100 µl Triton X-100 | 10% |
| 500 µl KCl | 1M |
| 20 µl $Mg_2SO_4$ | 1M |
| 100 µl $(NH)_2SO_4$ | 1M |
| 66 µl BSA | 10 mg/ml |
| 14 µl $H_2O$ | |

(from the above stocks concentrations)

A set of 16 templates (7 circular and 9 linear) and sixteen 17 nucleotide and sixteen 24 nucleotide long primers with all possible dinucleotide combinations at 3' ends were synthesized as a test system. The seven circular templates are discussed above in Example 5 and are shown in Table 6. The sixteen 17 nucleotide long primers are also discussed in Example 5 and are shown in Table 7. Nine mutagenesis primers for generating the nine linear templates are shown below in Table 10. (The mutations are underlined in the sequences in Table 10. The nine linear templates were generated by PCR using the nine upstream primers in Table 10 and one universal downstream PCR primer 775 GGC CGA TTC ATT AAT GCA GCT GGC-3' (position 973 in pCR-Script cat#21 1188, GenBank Accession #U46017) and template No. 13 from Table 6. The sixteen 24 nucleotide long primers are shown below in Table 11. All primers were synthesized on Expedite 8909 Moss Unit using 0-cyanoethyl phosphoamidite chemistries and were PAGE purified.

Primers 384 through 399 from Table 7 were used with the seven templates from Table 6 in dNTP titration experiments, which resulted in maximum 85% increase of priming specificity at a low concentration of 12 UM dNTP (Table 12 below). The conditions used for this experiment were the same as the conditions shown in Table 13, under the Stratagene, 97 column with the following exceptions: (1) HotStart beads were not used (1.5 mM Mg was included in the buffer, but HotStart beads were not used) and (2) the TouchDown protocol was not used (the PCR conditions were the same as the Stratagene, 97 column of Table 13, except that under the "Annealing" section, the "Onset Tm" and "Increment" listings do not apply (in other words, the linear temperature of 56° C. with the linear number of 30 cycles was used directly).

Based on this result, a set of 5 primers shown to have the highest mismatch ability (resistance for clearance) were chosen for further experiments. See Example 7 below. In order to increase further the priming specificity to a complete clearance of the residual mismatches, a simultaneous "TouchDown" protocol (Vos et al., Nucl. Acids Res., 23:4407–4414 (1995); Money et al., *Nucl. Acids Res.*, 24:2616–2617 (1996)) and Mg "Hot Start" were performed to try to upgrade the dNTP-cut approach (the dNTP-cut approach involves reducing dNTP concentration).

For all of the PCR reactions in this example, Pfu (Exo-) polymerase was used (Lunderberg et al., Gene, 108:1 (1991). The buffer system is described above. The PCR were performed with RoboCycler Gradient 96 Hot Top Lid (#400885) in 50 pi reaction volume and 96-well plates and thin-wall tube strips (#410082/92). The TouchDown programming was performed using RoboCycler link-programs menu. Magnesium HotBeads #MG150/50, which provided a final concentration 1.5 mM Mg in 50 ul PCR reaction, were purchased from LUMITEKK, Salt Lake City, Utah 84103. The following pb primer was used: #775 GGC CGA TTC ATT MT GCA GCT GGC-3' (position 973 in pCR-Script cat#211188, GenBank Accession #U46017). The conditions used are set forth below in Table 13.

The result showed that the above three conditions appear to work synergistically and can exterminate all mispriming polymerization events. Additionally, the significance of this observation was supported by a similar and independent result reported in Ault et al., "Type-specific amplification of viral DNA using touchdown and hot start PCR," *Journal of Virological Methods*, 46:145–156(1994). See Table 13 for the actual conditions used in the present example and reported in Ault et al. The conditions used for specific priming (dNTP concentration, Hot Start, and TouchDown) are called the SYN protocol.

The efficiency of this protocol was also achieved using the longer 24-mer primers shown below in Table 11 where the parameters of the TouchDown profile were changed (Table 13). The linear templates discussed above were also used to test whether terminal instability (breathing) can affect the system. The conditions in Table 13 were also used to test this protocol for clearance of mismatches at the −3 and −4 positions at the 3' end of the PCR primers. For this experiment, the set of primers in Table 14 were synthesized and used.

The complete set of 16 templates (7 circular and 9 linear) displayed significant mispriming at permissive conditions (permissive conditions include, for example, higher dNTP high concentrations, such as about 50 μM or higher) and the mispriming was cleared at restrictive conditions of the SYN protocol (Table 15). (The SYN protocol here refers to the conditions in Table 13 under the heading Stratagene, 97 where Mg-delay had a concentration of 1.5 mM.

TABLE 10

PCR mutagenesis primers 9 x 46mers
for generating linear templates:

909 CC TGC AGG TCA GCC TAA CGT CA CC TCG ACA AGG
TCT GAG TCA GTT C-3'

910 CC TGC AGG TCA GCC TAA CGT CA CG TCG ACA AGG
TCT GAG TCA GTT C-3'

TABLE 10-continued

PCR mutagenesis primers 9 x 46mers
for generating linear templates:

911 CC TGC AGG TCA GCC TAA CGT CA CT TCG ACA AGG
TCT GAG TCA GTT C-3'

912 CC TGC AGG TCA GCC TAA CGT CA GA TCG ACA AGG
TCT GAG TCA GTT C-3'

913 CC TGC AGG TCA GCC TAA CGT CA GC TCG ACA AGG
TCT GAG TCA GTT C-3'

914 CC TGC AGG TCA GCC TAA CGT CA GG TCG ACA AGG
TCT GAG TCA GTT C-3'

915 CC TGC AGG TCA GCC TAA CGT CA GT TCG ACA AGG
TCT GAG TCA GTT C-3'

916 CC TGC AGG TCA GCC TAA CGT CA TC TCG ACA AGG
TCT GAG TCA GTT C-3'

917 CC TGC AGG TCA GCC TAA CGT CA TG TCG ACA AGG
TCT GAG TCA GTT C-3'

TABLE 11

PCR reading primers 16 x 24mers:

858 CC CTG CAG GTC AGC CTA ACG TCA AA-3'

859 CC CTG CAG GTC AGC CTA ACG TCA AC-3'

860 CC CTG CAG GTC AGC CTA ACG TCA AG-3'

861 CC CTG CAG GTC AGC CTA ACG TCA AT-3'

862 CC CTG CAG GTC AGC CTA ACG TCA CA-3'

863 CC CTG CAG GTC AGC CTA ACG TCA CC-3'

864 CC CTG CAG GTC AGC CTA ACG TCA CG-3'

865 CC CTG CAG GTC AGC CTA ACG TCA CT-3'

866 CC CTG CAG GTC AGC CTA ACG TCA GA-3'

867 CC CTG CAG GTC AGC CTA ACG TCA GC-3'

868 CC CTG CAG GTC AGC CTA ACG TCA GG-3'

869 CC CTG CAG GTC AGC CTA ACG TCA GT-3'

870 CC CTG CAG GTC AGC CTA ACG TCA TA-3'

871 CC CTG CAG GTC AGC CTA ACG TCA TC-3'

872 CC CTG CAG GTC AGC CTA ACG TCA TG-3'

873 CC CTG CAG GTC AGC CTA ACG TCA TT-3'

TABLE 12

Table of the residual mispriming without using HotStart Beads and the TouchDown Protocol.

Primers (#384–399)
(-3' end)

| | | | | | | | |
|---|---|---|---|---|---|---|---|
| (—AA) | 3+ | — | 3 | — | 7 | -b | — |
| (-AC) | — | 8+ | — | 1 | — | -b | — |
| (-AG) | — | — | (?) | — | — | — | — |
| (-AT) | — | — | — | (8+) | — | -b | — |
| (-CA) | — | — | — | — | (?) | 3b | — |
| (-CC) | — | 5 | — | — | — | 5 | — |
| (-CG) | — | — | — | — | — | — | — |
| (-CT) | — | — | — | — | — | — | — |
| (-GA) | — | 5 | — | 3 | — | 8b | — |
| (-GC) | — | 5 | — | — | — | 5b | — |
| (-GG) | — | 3 | 5 | — | — | — | — |
| (-GT) | — | 3 | 5 | 3 | 3 | 3b | — |
| (-TA) | — | 3 | — | — | 8 | 6+ | — |
| (-TC) | — | — | — | — | — | b | — |
| (-TG) | — | — | — | — | — | — | — |
| (-TT) | — | — | — | — | — | — | 7+ |

Templates
(-3'-XX-5'-)

| | (-TT-) | (-TG-) | (-TC-) | (-TA-) | (-GT-) | (-AT-) | (-AA-) |

Intensity of the bands expressed by approx. levels up to 8
b - non specific background (usually only two heavier bands)
(+)Perfectmatch underlined (when absent - (?))

TABLE 13

Comparison of two independently achieved SYN protocols.

| | NIH, 94 | Stratagene, 97 |
|---|---|---|
| Enzyme | Taq (PE Cetus) | Pfu (Exo-) |
| pH | TrisHCl 8.3 | PIPES 6.5 |
| Volume | 100 μL | 50–100 μL |
| dNTP | 20 μM | 12–15 μM |
| Hot Start | dNTP-delay | Mg-delay (0.75–1.5 mM) |
| | Taq-delay | |
| Touchdown Profile | | |
| Melting | 94° C./3 min | 95° C./3 min |
| Annealing: | 67° C. (23–24 mers) | 65° C. (17 mers) |
| Onset Tm | | 76' C. (24 mers) |
| Increment | 2° C./cycle | 1° C./cycle |
| Linear Tm | 55° C. (23–24 mers) | 56° C. (17 mers) |
| | | 66° C. (24 mers) |
| Linear Nr | 25 cycles | 30 cycles |
| Extension | 72° C. | 68° C. |
| Timing | 30"/1'/1' | 1'/1'/1' |

TABLE 14

Primers for clearance at -4 (-1 and -2) position at the 3' end of the PCR primers:

```
#937    GTC AGC CTA ACG T TATA-3'    see also template
                         GTAT-5'     #13

#938    GTC AGC CTA ACG T TCTA-3'    see also template
                         GTAT-5'     #13

#939    GTC AGC CTA ACG T TACG-3'    see also template
                         GTGC-5'     #910

#940    GTC AGC CTA ACG T TCCG-3'    see also template
                         GTGC-5'     #910
```

TABLE 15

Clearance of mismatches at -4 (-1 and -2) at the 3' end of the PCR primers using the SYN protocol.

| Primer (- 3') #939 | Concentration of NTP in μM | | |
|---|---|---|---|
| Template [- 5' -] | 50 (-MgHS) | 50 (+MgHS) | 15 (+-MgHS) |
| -TACG | | | |
| -GTTT- | – | – | – |
| -GTTG- | – | – | – |
| -GTTC- | ++ | – | – |
| -GTTA- | + | – | – |
| -GTGT- | ++ | – | – |
| -GTAT- | + | – | – |
| -GTAA- | + | – | – |
| -GTGG- | +++ | – | – |
| -GTGC- | ++++ | + | – |
| -GTGA- | +++ | – | – |
| -GTCT- | + | – | – |
| -GTCG- | + | – | – |
| -GTCC- | ++ | – | – |
| -GTCA- | – | – | – |
| -GTAG- | – | – | – |
| -GTAC- | + | – | – |

Mismatches at -4 (3') were studied under 17 mer reading primers in presence of 15 μM & 50 μM NTP.
+/- Mg Hot start (MgHS)

EXAMPLE 7

Varying Conditions for Primer:Template Pairing

In the protocol in Example 6, a buffer with pH 6.5 (PIPES-HCl) was used. Such a pH may be restrictive for processivity in certain circumstances, since larger fragments may not be amplified. Thus, a buffer with pH 8.0 (Tris-HCl) was tested, and other parameters, such as different polymerases, dNTP concentration, and Mg concentration, were also tested. Specifically, the concentration of [H], [dNTP] and [Mg] ions were varied with the use of DNA Polymerase Pfu (Exo-), DNA Polymerase Taq (Stratagene Catalog #600139), and DNA Polymerase Taq2000 (Stratagene Catalog #600197). The pH 8.0 Tris-HCl buffer was the same as the buffer described in the sixth paragraph of Example 6 except Tris-HCl pH 8.0 was substituted for PIPES pH 6.5.

In these tests, we used the conditions in Table 13 above, under the Stratagene, '97 column, except we used one of the three different polymerases, a pH of 6.5 or 8, a dNTP concentration of 50 $\mu$M or 15 $\mu$M, and a Mg concentration of 1.5 mM or 0.75 mM. In these tests, we used six of the pairs of primers and templates shown in Table 12 above. Specifically, we used five pairs with higher levels of mis-pairing and a positive control with the correct pair. We used the template (-TG-) in the second column of Table 12 in conjunction with the primers having (-CC) and (-GC) at the −3' end, which pairs each had a value of 5 in Table 12. We also used the template (-GT-) in the fifth column of Table 12 in conjunction with the primers having (-AA) and (-TA) at the −3' end, which pairs had a value of 7 and 8, respectively, in Table 12. We also used the template (-AT-) in the sixth column of Table 12 in conjunction with the primer having (-GA) at the −3' end, which pair had a value of 8b in Table 12. Finally, we used the template (-TT-) in the first column of Table 12 in conjunction with the primer having (-AA) at the −3' end, which pair had a value of 3+in Table 12.

A master mix was prepared for 48 samples, each about 50 pi in volume. In a tube of 12 ml (Falcon), 3 ml water was mixed with 48 $\mu$l of primer #775 and 48 $\mu$l of Pfu(Exo-). The resulting volume of 3096 pi was divided evenly into two eppendorf tubes, which then each had a volume of 1548 pi. To the first tube, 3 $\mu$l (25 mM) dNTP was added, and to the second tube 9.2 $\mu$l (2.5 mM) dNTP was added. Thus, the contents of the first tube, after it has been subjected to the protocol and distributed into the wells as descibed below and in FIG. 14, will have a final concentration of 50 $\mu$M dNTP and the contents of the second tube, after it has been subjected to the protocol and distributed into the wells as descibed below and in FIG. 14, will have a final concentration of 15 $\mu$M dNTP.

The contents of each of the two eppendorf tubes was then divided into four tubes, two of which had a volume of 258 $\mu$l and two of which had a volume of 516 $\mu$l. The two tubes having the smaller volume of 258 $\mu$l will ultimately be used for 50 $\mu$l reaction series discussed below and shown in FIG. 14, and the two tubes having the larger volume of 516 $\mu$l will ultimately be used for 100 $\mu$l reaction series discussed below and shown in FIG. 14. Twenty-five 25 $\mu$l, Tris-HCl (pH 8) buffer described above was added to one of the 258 $\mu$l volume tubes, and 52 $\mu$l the Tris-HCl (pH 8) buffer was added to one of the 516 $\mu$l volume tubes. Twenty-five pi of the Tris-HCl (pH 8) buffer with Mg (1.5) (not in the form of wax beads) was added to the other of the 258 $\mu$l volume tubes, and 52 $\mu$l of the Tris-HCl (pH 8) buffer with Mg (0.75) (not in the form of wax beads) was added to the other of the 516 $\mu$l volume tubes.

Each of these 283 $\mu$l volume tubes and the 567 $\mu$l volume tubes were divided into six volumes of 46 $\mu$l and 94 $\mu$l, respectively, into a labeled 96-well PCR plate already loaded with the upstream primers (2 $\mu$l) and their corresponding templates (3 $\mu$l) as shown in FIG. 14, thus creating the 50 $\mu$l reaction series (the 50 $\mu$l reaction series actually had a volume of 51 $\mu$l) and the 100 pi reaction series (the 100 $\mu$l reaction series actually had a volume of 99 $\mu$l). To the wells that did not contain Mg in the buffer, 1.5 mM Mg wax beads were added. The Mg wax beads were Magnesium HotBeads #MG150/50, which provide a final concentration 1.5 mM Mg in 50 $\mu$l PCR reaction, which were purchased from LUMITEKK, Salt Lake City, Utah 84103. Thus, the final concentration of the Mg wax beads for the 50 pi series reactions shown in FIG. 14 was about 1.5 mM, and the final concentration of the Mg wax beads for the 100 $\mu$l, series reactions shown in FIG. 14 was about 0.75 mM.

This format of 48 reaction wells was also repeated, with the only exception that the buffer was changed to the PIPES-HCl (pH 6.5) buffer described above.

This format can be used to optimize conditions by creating sets that include variations in certain conditions or parameters or in the primers and templates. For example, this format was used in Example 8 below with different primers and a particular template.

Figure 15:
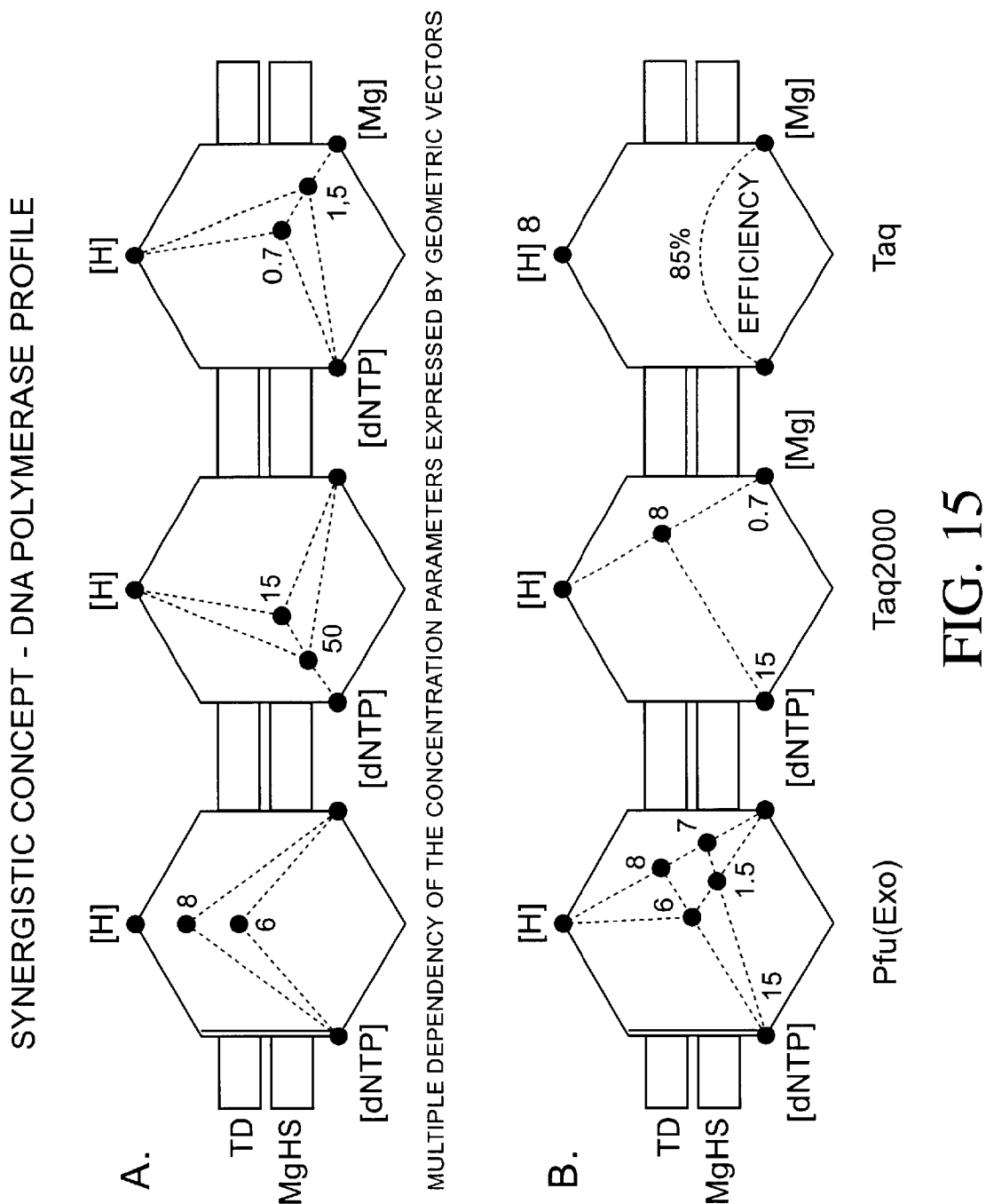
FIG. 15 shows certain possible variations in conditions for primer:template pairing.

Using geometrical vectors, FIG. 15 depicts the conditions that were varied in Part A, and the results of priming specificity are shown in Part B. Specifically, panel A shows that Touchdown and Mg HotStart were used for all tests, a pH of 6.5 and a pH of 8 were tested, dNTP concentrations of 15 $\mu$M and 50 $\mu$M were tested, and Mg concentrations of 0.75 mM and 1.5 mM were tested. Panel B shows that for Pfu(Exo-) and a dNTP concentration of 15 $\mu$M, for the conditions tested, when the pH was 6.5, the Mg HotStart concentration could be 1.5 mM, and when the pH was 8, the Mg HotStart concentration of 0.75 mM would work. (When the pH was 8, the Mg HotStart concentration of 1.5 mM did not work well.) Panel B also shows that for Taq2000 and a dNTP concentration of 15 $\mu$M, for the conditions tested, only a pH of 8 and Mg HotStart concentration of 0.75 mM worked well. Panel B also shows that for Taq and a dNTP concentration of 15 $\mu$M, none of the conditions tested worked well. Use of a dNTP concentration of 50 $\mu$M was too permissive with the conditions tested here.

Favored conditions are evidenced when one observes PCR product (and thus, amplification) in the wells in which there is correct primer:template pairing (e.g., Row C of FIG. 14), and does not observe PCR product (no amplification) in rows in which there are mismatches at the 3' end of the primer.

Thus, the easiest way to achieve priming was using Pfu(Exo-). This enzyme provides flexibility for changing both the pH and Mg concentration without affecting the final specificity. For example, if one decides to use buffer with pH 8, the corresponding relevant Mg HostStart concentration is 0.75 mM. If one decides to use buffer with pH 6.5, the corresponding relevant Mg HotStart concentration is 1.5 mM. Using DNA Polymerase Taq, we could not achieve 100% priming specificity at pH 8. Finally, using cloned DNA Polymerase Pfu (Exo+) (Stratagene catalog #600153), we did not achieve priming specificity, probably because that polymerase is able to remove all mismatched nucleotides at the 3' end of the primer and therefore extend all types of primers (intact and 3'-degraded).

This experiment shows methods for optimizing conditions for the PCR reaction used according to certain embodiments of the present invention. The protocols used here will help one skilled in the art to conduct further screening to optimize various conditions for appropriate specific priming in various settings.

EXAMPLE 8

Specific Amplification (or PCR Selection) Via Ligase Anchored Primer Sites

In the previous experiments, the junction of the public and private regions was not created by ligation. This experiment illustrated PCR selection using a public region ligated to a private region. FIG. 16 is a schematic depiction of the steps used in this experiment.

In order to generate a private region, the plasmid pBC (SK-) (Stratagene) was first cut by NaeI (Stratagene Catalog #500730, GCC/GGC) and ligated to the following adaptor designated Ad-A (Adaptor Ad-A is depicted by (++++++++) in FIG. 16):

5'-TGT AAG CGT GAA GAC GAC AGA AAG GGC GTG GTG CGG
                                            AGG GCG GT-3'

3'-GCC TCC CGC CA-5'

Next, the linearized pBC(SK-), with the adaptor Ad-A, was cut by EcoRV (Stratagene Catalog #500500, GAT/ATC) and ligated to the following adaptor Ad-B (Adaptor Ad-B is depicted by (========) in FIG. 16):

5'-CTC TGG CAT CAA CTC GGA CTA TCT CTT CGT CAT CTC
                                            ACC AAG-3'

3'-A GTA GAG TGG TTC-5'

Thus, two different public regions were terminally attached to a created private region with a size of 584 bp (NaeI position 131 and EcoRV position 715 in pBC (SK-)) that resulted in a fragment of total 670 bp. The ligation conditions used above were typical for blunt end ligation, which included ligation in polyethylene glycol (PEG) at 16° C. overnight. Conditions for ligating can be found in PCR Technology Current Innovations, Griffin et al., Chapter 16, Ligation and Anchored PCR, A. Troutt, CRC Press (1994), which is specifically incorporated herein by reference.

The ligated mixture was then purified over a QIAgen column (QIAgen) and preamplified using the following two primers:

5'-TGT AAG CGT GAA GAC GAC AGA-3'     (+++)

5'-CTC TGG CAT CAA CTC GGA CTA-3'     (===)

The PCR conditions for this preamplification step were 1 minute at 94° C. denaturation, 6 minutes at 68° C. annealing, and 6 minutes at 68° C. extension for 25 cycles in 50 µl reaction volume using cloned Pfu DNA Polymerase and buffer (Stratagene Catalog #200532) with Mg at pH 8.8. The PCR reaction was again purified over a QIAgen column and 1 µl was taken for the PCR selection experiment.

The following four primers for selection were synthesized:

| | |
|---|---|
| 3'-GGT GCG GAG GGC GGT GG-5' | for selection of NaeI private proximity, designated #378 |
| 3'-GGT GCG GAG GGC GGT AT-5' | for selection of EcoRV private proximity, designated #379 |
| 3'-CGT CAT CTC ACC AAG GG-5' | for selection of NaeI private proximity, designated #380 |
| 3'-CGT CAT CTC ACC AAG AT-5' | for selection of EcoRV private proximity, designated #381 |

The primers were grouped into the two couples #378/#381 and #379/#380 for selective PCR using the conditions in Table 13 under the heading Stratagene, 97, with a pH of 6.5 and Mg concentration of 1.5 mM. Only the fragment with size 670 was amplified with the primer couple #378/#381. The primer couple #379/#380 did not result in PCR amplification product. This experiment showed selective PCR amplification using a public region that has been ligated to a private region.

When we conducted this experiment with constructs in which adaptors Ad-A and Ad-B were simultaneously ligated to the private region, specific amplification was not achieved. Such simultaneous ligation probably resulted in constructs that had either Ad-A on both ends or Ad-B on both ends, as well as constructs with Ad-A and Ad-B on either end.

One skilled in the art will be able to produce constructs having an adaptor Ad-A one one end and an adaptor Ad-B on the other. For example, one can attach one end of adaptors to a solid support to prevent ligation to the end of the adaptor attached to the solid support. Subsequent to ligation to the private regions, the solid supports can be removed. As another example, one could use specific cohesive ends for specific ligation of only one end of the adaptors to the private regions.

EXAMPLE 9

Internal Primer Mismatches

A new primer set as shown in Table 16 below was synthesized. The primers were synthesized on Expedite 8909 Moss Unit using P3-cyanoethyl phosphoamidite chemistries and were PAGE purified. The primers are similar to primer # 384 of Table 7 above, but have mismatched nucleotides introduced into them relative to the template # 1 in Table 6. Specifically, primers # 640 to # 646 increase in mismatches with the template from one to six nucleotides (primer # 644 has five mismatches and primer # 645 has four mismatches), and the mismatches are all in the middle region of the primer sequence rather than at the '3 end of the sequence. The mismatched nucleotides are underlined in Table 16. PCR was carried out using the same format and conditions as that described above in Example 7, except primers # 640 to # 646 of Table 16 and template # 1 of Table 6 were used, and only the Tris-HCl pH 8 buffer was used. In other words, only one 48 well format was used with the Tris-HCl pH 8 buffer, and a second 48 well format with the PIPES pH 6.5 buffer was not performed.

The results shown in Table 16 indicate that priming and amplification occurred with the SYN protocol when there were two nucleotide mismatches in the middle region of the primer sequence. In contrast, as shown in Table 15, when there were two nucleotide mismatches at the '3 end of the primer, the SYN protocol prevented amplification. The results in Table 16 also show that three or more nucleotide mismatches in the middle region of the primer sequence prevented amplification, even when there were no 3' end nucleotide mismatches.

These results show that one can optimize conditions for carrying out particular PCR reactions in view of mismatches in the middle region of the primer sequence. For instance, if more permissive SYN conditions are desired, one needs to be careful not to allow amplification of templates when there are mismatches at the '3 end of the primer. To help prevent such improper amplification of mismatches at the '3 end of the primer, one may optimize proper amplification of only templates that have correct matches at the '3 end of the primer by introducing intentional mismatches in the middle region of the primer. Such intentional interior mismatches, will make the primer more sensitive to the SYN protocol when more permissive conditions are employed. Thus, one can achieve specific amplification of only templates with the proper pairing at the '3 end even with more permissive SYN conditions.

Thus, the number of mismatches in the middle region of the primer is yet another parameter that may influence specific PCR amplification. In view of this specification, one skilled in the art will be able to optimize SYN conditions for a desired PCR reaction in view of this additional parameter.

Tween-20 produced very clean results (no background-bands in contrast to certain results with the buffer pH 8 with Triton). However, the buffer with Tween-20 also required more restrictive conditions of 15 pM dNTP and 0.7 mM Mg wax beads in order to prevent completely amplification of templates with mismatches at the 3' end of the primer.

Human genomic DNA was purchased from PROMEGA (Catalog #G1521) (100 μg), and it was PCR titrated to find

TABLE 16

Design of mismatches in the middle of the primer and
SYN application (left three columns)
(the work reported here used Mg in the form of wax beads)

Specific/Nonspecific bands
− = no PCR product
+ to +++ = increasing amounts of PCR product

| Upstream primers: | 50 μl dNTP 1.5 mM Mg | 50 μl dNTP 0.75 mM Mg | 15 μl dNTP 1.5 mM Mg |
|---|---|---|---|
| #640 5'-GTC AGC C<u>GA</u> ACG TCA AA | +/− | +/− | +/− |
| #641 5'-GTC AGC C<u>GG</u> ACG TCA AA | +/+ | +/+ | +/− |
| #642 5'-GTC AGC <u>AGG</u> ACG TCA AA | +/+++ | +/+++ | −/− |
| #643 5'-GTC AG<u>A AGG</u> ACG TCA AA | −/++ | −/++ | −/− |
| #644 5'-GTC AG<u>A AGG C</u>CG TCA AA | −/++ | −/++ | −/− |
| #645 5'-GTC AG<u>A ATC C</u>CG TCA AA | −/+ | −/+ | −/− |
| #646 5'-GTC C<u>TAATC CA</u>G TCA AA | −/+ | −/+ | −/− |

Downstream primer: #775 (see Example 6)
Plasmid template #1 (see Table 6)

EXAMPLE 10

SYN Protocol on Complex Template (Human Genomic DNA)

The SYN buffer systems (at both pH 6.5 & 8), which had been used previously on plasmid templates (lower complexity) as discussed above, produced no amplification using a highly heterogeneous (complex) template such as on human genomic DNA. Thus, optimization of the buffer system was performed.

As a target loci, the human gene for a leukocyte antigen (HLA-DPβ) was selected. It has a significant allelic polymorphism that could be used for primer design and PCR allelic selection (Bugawan et al., J. Immunol., 141:4024–4030 (1988)). Based on the allelic sequence polymorphism, the following two upstream primers were designed to distinguish alleles DPβ2, 4, 5, 7, 8 from alleles DPβ1, 3, 6, 9, 10, and 11: (#823: 5'-AG MT TAC GTG TAC CAG GG; and #674: 5'-G AAT TAC GTG TAC CAG TT (the 3' end of both of these primers match position 34 in the second exon of the gene)) and one downstream primer (#677: 5'-TGC AGG GTC ATG GGC CCG C (the 3' end of this primer matches position 256 in the second exon of the gene, but in the antisense position)). The primers were synthesized on Expedite 8909 Moss Unit using β-cyanoethyl phosphoamidite chemistries and were PAGE purified.

The SYN protocol (see the format in Example 7) was first tested with a buffer composed of 40 mM KCl, 70 mM TrisHCl pH 8, and 0.1% Tween-20 detergent (SIGMA; catalog no. P1379), using Pfu (Exo-) on the five plasmid templates. In other words, the same 48 well PCR reactions described in Example 7 were performed, with the only exception being the use of only the buffer described above with the detergent Tween-20. The buffer with the detergent Tween-20 produced very clean results (no background-bands in contrast to certain results with the buffer pH 8 with Triton). However, the buffer with Tween-20 also required more restrictive conditions of 15 pM dNTP and 0.7 mM Mg wax beads in order to prevent completely amplification of templates with mismatches at the 3' end of the primer.

the optimum amount of template per well to use (optimal results were obtained with 50 ng template per well) using a buffer composed of 40 mM KCl, 70 mM TrisHCl pH 8, and 0.1% Tween-20. Using the buffer with Tween-20, a selective PCR involving the HLA-DPβ loci was performed using the # 823 and # 674 primers and the # 677 template. This PCR reaction was performed using Pfu(Exo-), the buffer including Tween-20 as described above, 30 μM dNTP, the Mg wax beads described in Example 7 (1.5 mM), and the human genomic DNA described above (50 ng per well). The remainder of the reaction conditions were the same as those described in Table 13, under the Stratagene, ' 97 column.

The results of this work showed that the couple #823/#677 (with -GG at the 3' end) resulted in the bands (showing the presence of PCR amplification product), and the couple #674/#677 (with -TT at the 3' end) did not result in bands (showing the lack of PCR amplification product). These results indicated that DPβ alleles 1, 3, 6, 9, 10, 11 were present in the sample, and the alleles 2, 4, 5, 7, 8 were not present in the sample.

These results show that yet another parameter that may be changed to optimize SYN conditions for a particular embodiment of the invention is the type of detergent used in the buffer. By running optimization tests, such as those described in this specification, one skilled in the art will be able to test other buffers to determine whether they provide optimal conditions. For example one may want to achieve conditions which are the most permissive without sacrificing the specificity of amplification of correctly matched nucleotides at the '3 end of the primers.

The specific embodiments described herein do not limit the scope of this invention. They are representative of embodiments of the claimed invention.

What is claimed is:

1. A composition comprising a mixture of different species of molecules, wherein at least some of said molecules are derived from a combinatorial synthesis process, wherein at least some of the species are linked to a tag comprising linked information encoding elements wherein the combination of elements imparts a physical property that is not characteristic of any one element alone and wherein at least some of said tags have a unique physical property when compared to other tags, wherein the physical property of the combination of elements identifies the species of molecule without determining the physical property of each element of said tag, and wherein said tags do not consist solely of nucleotides.

2. The composition in claim 1 wherein the mixture contains at least 10 species of molecules.

3. The composition in claim 1 wherein each tag has a uniquely identifiable molecular weight.

4. The composition in claim 1 wherein each tag comprises a reporter subunit and a base subunit that associate with one another, such that the reporter subunit dissociates from the base subunit under uniquely identifiable dissociation conditions.

5. The composition in claim 4 wherein a reporter subunit comprises a protein, nucleic acid, or other affinity reagent that recognizes the base subunit.

6. The composition in claim 5 wherein the reporter subunit comprises an oligonucleotide.

7. The composition in claim 6 wherein the reporter subunit is immobilized.

8. The composition in claim 4 wherein the base subunit comprises an oligonucleotide.

9. The composition in claim 8 wherein the base subunit is immobilized.

10. The composition in claim 8 wherein the reporter subunit comprises an oligonucleotide and wherein the reporter and base subunits are perfectly complementary.

11. The composition in claim 8 wherein the reporter subunit comprises an oligonucleotide and wherein the reporter and base subunits are not perfectly complementary.

12. The composition in claim 4 wherein the reporter subunit is a hydrocarbon.

13. The composition in claim 12 wherein the reporter subunits are hydrocarbons of varying chain length and/or hydrophobicity.

14. The composition in claim 4 wherein the reporter subunit is an amino acid residue.

15. The composition in claim 4 wherein the reporter subunits are amino acid residues of varying numbers of residues and/or isoelectric points.

16. The composition in claim 4 wherein temperature is used to vary the dissociation conditions.

17. The composition in claim 4 wherein the mixture is in a disassociating agent such that the concentration of the disassociating agent is varied directly or indirectly to vary the dissociation conditions.

18. The composition in claim 17 wherein a change in pH is used to vary the dissociation conditions.

19. The composition in claim 17 wherein formamide is used to vary the dissociation conditions.

20. The composition in claim 17 wherein urea is used to vary the dissociation conditions.

21. The composition in claim 4 wherein a field is used to vary the dissociation conditions.

22. The composition in claim 21 wherein the field is an electrical field.

23. The composition in claim 21 wherein the field is a magnetic field.

24. The composition in claim 1 wherein each tag comprises uniquely identifiable information encoding elements, wherein the order of the elements within the tag provides information regarding the identity of the tag.

25. The composition in claim 24 wherein the information encoding elements have uniquely identifiable isotopic emissions.

26. The composition in claim 25 wherein the information encoding elements include radioisotopes.

27. The composition in claim 24 wherein the information encoding elements have uniquely identifiable molecular weights.

28. The composition in claim 24 wherein the information encoding elements have uniquely identifiable physical sizes.

29. The composition in claim 24 wherein the information encoding elements have uniquely identifiable light absorbing or emitting properties.

30. The composition in claim 24 wherein the information encoding elements have uniquely identifiable magnetic properties.

31. The composition of claim 24 wherein the information encoding elements have uniquely identifiable electrical properties.

32. The composition of claim 24 wherein the information encoding elements have uniquely identifiable molecular compositions.

33. The composition of claim 32 wherein the uniquely identifiable molecular compositions can be identified by NMR.

34. The composition of claim 32 wherein the uniquely identifiable molecular compositions can be identified by atomic force microscopy.

35. The composition of claim 24 wherein the information encoding elements have uniquely identifiable molecular structures.

36. The composition of claim 35 wherein the uniquely identifiable molecular structures can be identified by their three dimensional structure.

37. The composition of claim 35 wherein the uniquely identifiable molecular structures can be identified by their affinity for an antibody or an antigen.

38. The composition of claim 35 wherein the uniquely identifiable molecular structures can be identified by their affinity for a ligand.

39. A method for creating a mixture of at least one hundred species of molecules wherein at least some of said molecules are linked to a uniquely identifiable tag comprising information encoding elements comprising:

(I) performing parallel first synthesis reactions in separate reaction vessels, wherein a first information encoding element is linked to a first synthesis product produced in each vessel, wherein at least some of the first encoding elements are unique for the first synthesis product in each separate reaction vessel;

(ii) mixing the first synthesis products;

(iii) placing portions of the mixture from (ii) into new separate reaction vessels and performing parallel second synthesis reactions to modify the first synthesis products to create a second synthesis product in the new separate reaction vessels, wherein a second information encoding element is linked to the first information encoding element that is linked to the second synthesis product in each vessel, wherein at least some of the second information encoding elements are unique for each of the second synthesis reactions in each separate reaction vessel such that the combination of elements imparts a physical property that is unique to at least some of the tags in said mixture, wherein the physical property of the combination of elements identifies the species of molecule without the need to determine a physical property of each element of said tag independently, and wherein the tags do not consist solely of nucleic acid encoding elements.

40. A method of claim 39, further comprising:

(iv) mixing the second synthesis products;

(v) placing portions of the mixture from (iv) into new separate reaction vessels and performing parallel third chemical synthesis reactions to modify the second synthesis products to create third chemical synthesis products in the new separate reaction vessels, wherein a third information encoding element is coupled to the third synthesis product in each vessel, each of the third information encoding elements being unique for each of the third chemical synthesis reactions in each separate reaction vessel such that the order of coupling of such first, second, and third information encoding elements can be determined without first isolating each of the tags.

41. A method for creating a mixture of at least one hundred species of molecules wherein at least some of said molecules are linked to a uniquely identifiable tag comprising information encoding elements comprising:

(i) performing parallel first enzymatic reactions in separate reaction vessels, wherein a first information encoding element is linked to a first enzymatic product produced in each vessel, wherein at least some of the first encoding elements are unique for the first enzymatic product in each separate reaction vessel;

(ii) mixing the first enzymatic products;

(iii) placing portions of the mixture from (ii) into new separate reaction vessels and performing parallel second enzymatic reactions to modify the first enzymatic products to create second enzymatic products in the new separate reaction vessels, wherein a second information encoding element is linked to the first information encoding element that is linked to the second enzymatic product in each vessel, wherein at least some of the second information encoding elements are unique for at least some of the second enzymatic reactions in at least some of the separate reaction vessels such that the order of coupling of the first and second information encoding elements of at least some of the tags can be determined without first isolating each of the tags, and wherein the tags do not consist solely of nucleic acid encoding elements.

42. A method of claim 41, further comprising:

(iv) mixing the second enzymatic products;

(v) placing portions of the mixture from (iv) into new separate reaction vessels and performing parallel third enzymatic reactions to modify the second enzymatic products to create third enzymatic products in the new separate reaction vessels, wherein a third information encoding element is coupled to the third enzymatic product in each vessel, each of the third information encoding elements being unique for each of the third enzymatic reactions in each separate reaction vessel such that the order of coupling of such first, second, and third information encoding elements can be determined without first isolating each of the tags.

43. The method in claim 42 wherein the information encoding elements have uniquely identifiable isotopic emissions.

44. The method in claim 43 wherein the information encoding elements include radioisotopes.

45. The method in claim 42 wherein the information encoding elements have uniquely identifiable molecular weights.

46. The method in claim 42 wherein the information encoding elements have uniquely identifiable physical sizes.

47. The method in claim 42 wherein the information encoding elements have uniquely identifiable light absorbing or emitting properties.

48. The method in claim 42 wherein the information encoding elements have uniquely identifiable magnetic properties.

49. The method of claim 42 wherein the information encoding elements have uniquely identifiable electrical properties.

50. The method of claim 42 wherein the information encoding elements have uniquely identifiable molecular methods.

51. The method of claim 42 wherein the information encoding elements have uniquely identifiable molecular structures.

52. The method in claim 42 wherein the enzymatic reaction is an amplification reaction.

53. The method in claim 52 wherein the enzymatic reactions utilize the polymerase chain reaction.

54. The method in claim 52 wherein the enzymatic reactions utilize the ligase chain reaction.

55. The method in claim 52 wherein the enzymatic reactions amplify certain reaction substrates in preference to other reaction substrates based on the nucleotide sequence of such substrates.

56. The method in claim 42 wherein the tags comprise nucleic acids.

57. A composition comprising a mixture of different species of molecules, wherein at least some of said molecules are derived from a combinatorial synthesis process, wherein at least some of the species are linked to a tag, said tag comprising at least two linked uniquely identifiable information encoding elements that are unique to at least two variable positions on the species wherein the combination of elements imparts a physical property that is not characteristic of any element alone and wherein at least some of the tags have a unique physical property when compared to other tags, wherein the physical property of the combination of elements identifies the species of molecule without determining the physical property of each element of said tag, and wherein the tags do not consist solely of nucleic acid encoding elements.

58. A composition comprising a mixture of different species of molecules, wherein at least some of said molecules are derived from a combinatorial synthesis process, wherein each species is linked to a tag, said tag comprising operatively linked information encoding elements wherein the combination of elements imparts a physical property that is unique to each tag in said mixture, wherein the physical property of the combination of elements identifies the species of molecule without the need to determine a physical property of each element of said tag independently, and wherein each tag comprises a reporter subunit and a base subunit that associate with one another, such that the reporter subunit dissociates from the base subunit under uniquely identifiable dissociation conditions.

59. A method for determining the sequence of a nucleic acid comprising:
shearing the nucleic acid into random fragments;
specifically amplifying the random fragments based on all possible combinations of nucleotides at positions 1 to X at one end of each of the random fragments to create first stage amplification products, wherein X is an integer from 2 to 6;
encoding at least one first stage tag element that specifically corresponds to each possible combination of nucleotides at positions 1 to X at the end of each fragment;
specifically amplifying the first stage amplification products based on all possible combinations of specific nucleotides at positions X+1 or X+1 to Y of each of the first stage amplification products to create second stage products, wherein Y is an integer from 4 to 12;
encoding at least one second stage tag element that specifically corresponds to each possible combination of nucleotides at positions X+1 or X+1 to Y of each first stage product thereby creating a tag that uniquely encodes nucleotides at positions 1 to X+1 or 1 to Y of each fragment;
simultaneously decoding the tags without prior separation of the tags to determine the nucleotides of each fragment at positions 1 to X+1 or 1 to Y; and
determining the nucleic acid sequence by the overlap of the nucleotides identified at positions 1 to X+1 or 1 to Y of the fragments.

60. A method for detecting mutations in a sample nucleic acid sequence comprising:
randomly shearing a wild type nucleic acid sequence into wild type fragments;
creating probes that encode nucleotides at positions 1 to X at one end of each of the wild type fragments, wherein X is an integer from 2 to 6, and each of said probes being complementary to each of said wild type fragments but lacking a complementary sequence for nucleotides at positions 1 to X+1 of each wild type fragment;
randomly shearing the sample nucleic acid sequence into sample fragments;
separately exposing the sample fragments and the wild type fragments to the probes;
performing primer extension with the probes to encode each nucleotide at position X+1 of each sample fragment and each wild type fragment;
simultaneously decoding the probes to determine each nucleotide at position X+1 of each sample fragment and each wild type fragment; and
comparing the decoded results of the sample fragments to the wild type fragments to detect differences between specific positions of the wild type nucleic acid sequence and the sample nucleic acid sequence.

61. A method for detecting mutations in a sample nucleic acid sequence comprising:
randomly shearing the sample nucleic acid sequence into sample fragments;
separately exposing the sample fragments and wild type fragments, obtained from randomly sheared wild type nucleic acid sequence, to the probes, said probes encoding nucleotides at positions 1 to X at one end of each of the wild type fragments, wherein X is an integer from 2 to 6, and each of said probes being complementary to each of said wild type fragments but lacking a complementary sequence for nucleotides at positions 1 to X+1 of each wild type fragment;
performing primer extension with the probes to encode each nucleotide at position X+1 of each sample fragment and each wild type fragment;
simultaneously decoding the probes to determine each nucleotide at position X+1 of each sample fragment and each wild type fragment; and
comparing the decoded results of the sample fragments to the wild type fragments to detect differences between specific positions of the wild type nucleic acid sequence and the sample nucleic acid sequence.

62. A kit for detecting mutations in a sample nucleic acid sequence comprising:
wild type fragments obtained from a randomly sheared wild type nucleic acid sequence; and
probes encoding nucleotides at positions 1 to X at one end of each of the wild type fragments, wherein X is an integer from 2 to 6, and each of said probes being complementary to each of said wild type fragments but lacking a complementary sequence for nucleotides at positions 1 to X+1 of each wild type fragment.

63. A method for detecting the presence or absence of or quantity of particular mRNA in a sample comprising:
creating reference cDNA from a reference mRNA population;

cleaving the reference cDNA with a restriction enzyme that is specific for a specific X consecutive nucleotides, wherein X is an integer from 2 to 6, to create reference cDNA fragments each having the same nucleotides at positions 1 to X at one end;

creating probes that encode nucleotides at positions X+1 to Y of each of the cDNA fragments, wherein Y is an integer from 4 to 12, and each of said probes being complementary to each of said cDNA fragments but lacking a complementary sequence for nucleotides at positions 1 to Y+1 of each cDNA fragment;

creating target cDNA from target mRNA in a sample;

cleaving the target cDNA with the restriction enzyme that is specific for X consecutive nucleotides to create target cDNA fragments;

exposing the target cDNA fragments to the probes;

performing primer extension with the probes to encode each nucleotide at position Y+1 of each target cDNA fragment that is present that corresponds to a reference cDNA fragment;

detecting the presence or absence of or quantity of target cDNA fragments corresponding to reference cDNA fragments to detect the presence or absence of or quantity of target mRNA in the sample.

64. A method for detecting the presence of absence of or quantity of particular mRNA in a sample comprising:

creating target cDNA from target mRNA in the sample;

cleaving the target cDNA with a restriction enzyme that is specific for X consecutive nucleotides to create target cDNA fragments each having the same nucleotides at positions 1 to X, wherein X is an integer from 2 to 6;

exposing the target cDNA fragments to probes, said probes each encoding the same nucleotides at positions 1 to X as the target cDNA fragments, each of said probes also encoding nucleotides at positions X+1 to Y of reference cDNA fragments created from a reference mRNA population and cleaved by the restriction enzyme, wherein Y is an integer from 4 to 12, and each of said probes being complementary to each of said reference cDNA fragments but lacking a complementary sequence for nucleotides at positions 1 to Y+1 of each reference cDNA fragment;

performing primer extension with the probes to encode each nucleotide at position Y+1 of each target cDNA fragment that is present that corresponds to a reference cDNA fragment;

detecting the presence or absence of or quantity of target cDNA fragments corresponding to reference cDNA fragments to detect the presence or absence of or quantity of target mRNA in the sample.

65. A kit for detecting the presence or absence of or quantity of particular mRNA in a sample comprising:

multiple probes each encoding the same nucleotides at positions 1 to X, said positions 1 to X being associated with a given restriction enzyme, wherein X is an integer from 2 to 6, each of said probes also encoding nucleotides at positions X+1 to Y of reference cDNA fragments created from a reference mRNA population and cleaved by the given restriction enzyme, wherein Y is an integer from 4 to 12, and each of said probes being complementary to each of said reference cDNA fragments but lacking a complementary sequence for nucleotides at positions 1 to Y+1 of each reference cDNA fragment.

66. A method for identifying molecular species from a mixture of at least one hundred different molecular species comprising:

performing multiple consecutive sets of parallel different syntheses;

creating a tag for each molecular species generated from the consecutive sets of syntheses using information encoding elements that each specifically correspond to a particular synthesis and that identify the order of syntheses, wherein said tags comprise linked information encoding elements wherein the combination of elements imparts a physical property that is unique for at least some of said tags in said mixture and that can be determined without the need to determine a physical property of each element of said tag; and decoding the tags without determining the physical property of each element of said tags to determine at least some of the molecular species created by the consecutive sets of parallel different syntheses.

67. The composition of claim 1 wherein the combined physical property that is unique to each tag can be determined in a system wherein the different molecular species can diffuse in a liquid phase.

68. A composition comprising a mixture of at least one hundred different species of molecules, wherein at least some of said molecules are derived from a combinatorial synthesis process and wherein each species is linked to a tag, said tag comprising linked elements wherein the order of elements imparts a physical property that is unique to each tag within the mixture.

69. The composition of claim 1 wherein the physical property is molecular mass.

70. The composition of claim 1 wherein said tag can be identified without the need for first isolating each of the tags prior to performing a decoding procedure.

71. A method for identifying tags in a composition comprising a mixture of at least one hundred different species of molecules, wherein at least some of the species are linked to a tag, said tag comprising linked information encoding elements wherein the combination of at least two encoding elements imparts a physical property that is not characteristic of any one element alone and wherein at least some of the tags have a unique physical property when compared to other tags and wherein the physical property of the combination of elements identifies the species of molecule, comprising:

identifying said tags based on said physical property that is unique to said tag and not based on the mere order of said encoding elements.

72. A composition comprising a mixture of at least one hundred different species of molecules, wherein at least some of said molecules are derived from a combinatorial synthesis process, wherein each species is linked to a tag, said tag comprising linked information encoding elements wherein the combination of elements imparts a physical property that is unique to each tag in said mixture and that can be determined without the need to determine the sequence of elements in said tag.

73. The composition of claim 72 wherein said tag can be identified without the need for first isolating each of the tags prior to performing a decoding procedure.

74. A method comprising identifying tagged species present in the composition of claims 1, 68, or 72 by detecting one or more physical properties of the tags in said composition.

75. The method of claim 74 wherein the physical property comprises at least one of: electrophoretic mobility, light absorption, nuclear magnetic resonance, radioisotopic emission, light frequency emission, light intensity emission, radiofrequency emission, mobility in an electric field, mobility in a pH gradient, isoelectric focussing pH, mobility in a magnetic field, gel filtration mobility, molecular size, melting temperature, annealing temperature, binding to a nucleic acid probe, binding energy, dissociation energy, dielectric constant, electrical charge, molecular mass, fluorescent emission, rate of diffusion, color, harmonic frequency, electrical conductivity, electrical resistance, molecular shape, efficiency as a substrate in a ligation reaction, efficiency as a substrate in a polymerization reaction, or efficiency as a substrate in a restriction enzyme digestion reaction.

76. The method in claim 74 wherein the tag is a single stranded nucleic acid and the physical property is the binding to a second nucleic acid.

77. The method in claim 74 wherein the physical property detected is the annealing of the tags to two or more target nucleic acid molecules.

78. The method of claim 74 wherein the tag comprises duplexed nucleic acids.

79. The method of claim 78 wherein the physical property detected is the denaturation of the duplexed nucleic acids.

80. The method of claim 74 wherein each tagged species comprises a uniquely identifiable tag comprising information encoding elements created by a method comprising:

(i) performing parallel first synthesis reactions in separate reaction vessels, wherein a first information encoding element is coupled to a first synthesis product produced in each vessel, each of the first encoding elements being unique for the first synthesis product in each separate reaction vessel;

(ii) mixing the first synthesis products;

(iii) placing portions of the mixture from (ii) into new separate reaction vessels and performing parallel second synthesis reactions to modify the first synthesis products to create a second synthesis product in the new separate reaction vessels, wherein a second information encoding element is coupled to the second synthesis product in each vessel, each of the second information encoding elements being unique for each of the second synthesis reactions in each separate reaction vessel such that the combination of elements imparts a physical property that is unique to each tag in said mixture, and wherein the physical property of the combination of elements identifies the species of molecule without the need to determine a physical property of each element of said tag independently.

81. The method of claim 80, wherein said tagged species creation method further comprises:

(iv) mixing the second synthesis products;

(v) placing portions of the mixture from (iv) into new separate reaction vessels and performing parallel third synthesis reactions to modify the second synthesis products to create third synthesis products in the new separate reaction vessels, wherein a third information encoding element is coupled to the third synthesis product in each vessel, each of the third information encoding elements being unique for each of the third synthesis reactions in each separate reaction vessel such that the combination of elements imparts a physical property that is unique to each tag in said mixture, and wherein the physical property of the combination of elements identifies the species of molecule without the need to determine a physical property of each element of said tag independently.

82. The method of claim 74 wherein each tagged species comprises a uniquely identifiable tag comprising information encoding elements created by a method comprising:

(i) performing parallel first enzymatic reactions in separate reaction vessels, wherein a first information encoding element is coupled to a first enzymatic product produced in each vessel, each of the first encoding elements being unique for the first enzymatic product in each separate reaction vessel;

(ii) mixing the first enzymatic products;

(iii) placing portions of the mixture from (ii) into new separate reaction vessels and performing parallel second enzymatic reactions to modify the first enzymatic products to create second enzymatic products in the new separate reaction vessels, wherein a second information encoding element is coupled to the second enzymatic product in each vessel, each of the second information encoding elements being unique for each of the second enzymatic reactions in each separate reaction vessel such that the combination of elements imparts a physical property that is unique to each tag in said mixture, and wherein the physical property of the combination of elements identifies the species of molecule without the need to determine a physical property of each element of said tag independently.

83. The method of claim 82 wherein said tagged species creation method further comprises:

(iv) mixing the second enzymatic products; and (v) placing portions of the mixture from (iv) into new separate reaction vessels and performing parallel third enzymatic reactions to modify the second enzymatic products to create third enzymatic products in the new separate reaction vessels, wherein a third information encoding element is coupled to the third enzymatic product in each vessel, each of the third information encoding elements being unique for each of the third enzymatic reactions in each separate reaction vessel such that the combination of elements imparts a physical property that is unique to each tag in said mixture, and wherein the physical property of the combination of elements identifies the species of molecule without the need to determine a physical property of each element of said tag independently.

84. The composition of claims 1, 68, or 72 wherein the physical property comprises at least one of: electrophoretic mobility, light absorption, nuclear magnetic resonance, radioisotopic emission, light frequency emission, light intensity emission, radiofrequency emission, mobility in an electric field, mobility in a pH gradient, isoelectric focussing pH, mobility in a magnetic field, gel filtration mobility, molecular size, melting temperature, annealing temperature, binding to a nucleic acid probe, binding energy, dissociation energy, dielectric constant, electrical charge, molecular mass, fluorescent emission, rate of diffusion, color, electrical conductivity, electrical resistance, molecular shape, efficiency as a substrate in a ligation reaction, efficiency as a substrate in a polymerization reaction, or efficiency as a substrate in a restriction enzyme digestion reaction.

85. The composition of claim 1, wherein the mixture of different species comprises at least one hundred species.

86. The composition of claim 68, wherein the tags can be identified without the need for first isolating each of the tags prior to performing a decoding step.

87. A composition comprising a mixture of at least one hundred different species of molecules, wherein at least some of said molecules are derived from a combinatorial synthesis process, wherein each species is linked to a tag, said tag comprising linked information encoding elements wherein the combination of elements imparts a physical property that is unique to each tag in said mixture and wherein said tag does not consist solely of nucleotides.

88. The method of claim 74, wherein said detection is simultaneous.

* * * * *